(12) United States Patent
Reid et al.

(10) Patent No.: US 11,959,906 B2
(45) Date of Patent: Apr. 16, 2024

(54) ANALYSIS OF MEASUREMENTS OF A POLYMER

(71) Applicant: Oxford Nanopore Technologies PLC, Oxford (GB)

(72) Inventors: Stuart William Reid, Oxford (GB); James Anthony Clarke, Oxford (GB); James White, Oxford (GB); Gavin Harper, Sonning (GB)

(73) Assignee: Oxford Nanopore Technologies PLC, Oxford (GB)

( * ) Notice: Subject to any disclaimer, the term of this patent is extended or adjusted under 35 U.S.C. 154(b) by 511 days.

(21) Appl. No.: 16/245,306

(22) Filed: Jan. 11, 2019

(65) Prior Publication Data
US 2019/0154655 A1 May 23, 2019

Related U.S. Application Data

(63) Continuation of application No. 14/379,242, filed as application No. PCT/GB2013/050381 on Feb. 18, 2013, now abandoned.
(Continued)

(51) Int. Cl.
*G01N 33/48* (2006.01)
*B82Y 15/00* (2011.01)
(Continued)

(52) U.S. Cl.
CPC ........ *G01N 33/48792* (2013.01); *B82Y 15/00* (2013.01); *C12Q 1/6858* (2013.01);
(Continued)

(58) Field of Classification Search
CPC ............. G01N 33/48792; G01N 27/02; G01N 33/6803; G01N 33/6875; G01N 33/48721;
(Continued)

(56) References Cited

U.S. PATENT DOCUMENTS

| 5,795,782 A | 8/1998 | Church et al. |
| 6,128,587 A | 10/2000 | Sjolander |

(Continued)

FOREIGN PATENT DOCUMENTS

| EP | 1351183 A2 | 10/2003 |
| EP | 1544310 A2 | 6/2005 |

(Continued)

OTHER PUBLICATIONS

Chu et al. Real-time monitoring of DNA polymerase function and stepwise single-nucleotide DNA translocation through a protein nanopore. Angew. Chem. Int. Ed. vol. 49, pp. 10106-10109. (Year: 2010).*

(Continued)

*Primary Examiner* — Russell S Negin

(74) *Attorney, Agent, or Firm* — Wolf, Greenfield & Sacks, P.C.

(57) ABSTRACT

A time-ordered series of measurements of a polymer made during translocation of the polymer through a Nanopore are analysed. The measurements are dependent on the identity of k-mers in the Nanopore, a k-mer bring k polymer units of the polymer, where k is a positive integer. The method involves deriving, from the series of measurements, a feature vector of time-ordered features representing characteristics of the measurements; and determining similarity between the derived feature vector and at least one other feature vector.

25 Claims, 17 Drawing Sheets

Specification includes a Sequence Listing.

Related U.S. Application Data

(60) Provisional application No. 61/599,573, filed on Feb. 16, 2012.

(51) Int. Cl.

| | | |
|---|---|---|
| *C12Q 1/6858* | (2018.01) | |
| *C12Q 1/6869* | (2018.01) | |
| *G01N 27/02* | (2006.01) | |
| *G01N 33/487* | (2006.01) | |
| *G01N 33/50* | (2006.01) | |
| *G01N 33/68* | (2006.01) | |
| *G16B 30/10* | (2019.01) | |
| *G16B 30/00* | (2019.01) | |

(52) U.S. Cl.
CPC .......... *C12Q 1/6869* (2013.01); *G01N 27/02* (2013.01); *G01N 33/48721* (2013.01); *G01N 33/6803* (2013.01); *G01N 33/6875* (2013.01); *G16B 30/10* (2019.02); *G16B 30/00* (2019.02)

(58) Field of Classification Search
CPC ........ G16B 30/10; G16B 30/00; B82Y 15/00; C12Q 1/6858; C12Q 1/6869
See application file for complete search history.

(56) References Cited

U.S. PATENT DOCUMENTS

| | | | |
|---|---|---|---|
| 7,625,706 | B2 | 12/2009 | Akeson et al. |
| 7,731,826 | B2 | 6/2010 | Hibbs et al. |
| 8,324,914 | B2 | 12/2012 | Chen et al. |
| 8,452,546 | B1 | 5/2013 | Lathrop |
| 9,057,102 | B2 | 6/2015 | Turner et al. |
| 9,121,064 | B2 | 9/2015 | Turner et al. |
| 9,127,313 | B2 | 9/2015 | Brown et al. |
| 9,546,400 | B2 | 1/2017 | Turner et al. |
| 9,556,480 | B2 | 1/2017 | Turner et al. |
| 9,678,056 | B2 | 6/2017 | Turner et al. |
| 9,738,929 | B2 | 8/2017 | Turner et al. |
| 10,131,943 | B2 | 11/2018 | Reid et al. |
| 10,689,697 | B2 | 6/2020 | Reid et al. |
| 11,085,077 | B2 | 8/2021 | Reid et al. |
| 11,401,549 | B2 | 8/2022 | Reid et al. |
| 2002/0197618 | A1 | 12/2002 | Sampson |
| 2003/0099951 | A1 | 5/2003 | Akeson et al. |
| 2005/0159898 | A1 | 7/2005 | Yasuda et al. |
| 2005/0202444 | A1 | 9/2005 | Zhu |
| 2005/0272923 | A1 | 12/2005 | Zhang et al. |
| 2006/0019259 | A1 | 1/2006 | Joyce |
| 2006/0086626 | A1 | 4/2006 | Joyce |
| 2007/0161028 | A1 | 7/2007 | Schwartz et al. |
| 2010/0331194 | A1 | 12/2010 | Turner et al. |
| 2011/0121840 | A1 | 5/2011 | Sanghera et al. |
| 2011/0226623 | A1 | 9/2011 | Timp et al. |
| 2013/0023423 | A1 | 1/2013 | Kavanagh et al. |
| 2013/0071837 | A1 | 3/2013 | Winters-Hilt et al. |
| 2013/0146456 | A1 | 6/2013 | Gundlach et al. |
| 2014/0255918 | A1 | 9/2014 | Olasagasti et al. |
| 2015/0057948 | A1 | 2/2015 | Reid et al. |
| 2015/0152492 | A1 | 6/2015 | Brown et al. |
| 2015/0152495 | A1 | 6/2015 | Stava et al. |
| 2015/0344944 | A1 | 12/2015 | Reid et al. |
| 2016/0162634 | A1 | 6/2016 | Reid et al. |
| 2017/0091427 | A1 | 3/2017 | Massingham |
| 2017/0096703 | A1 | 4/2017 | Dolan et al. |
| 2017/0219557 | A1 | 8/2017 | Reid et al. |
| 2017/0233804 | A1 | 8/2017 | Reid et al. |
| 2019/0203286 | A1 | 7/2019 | Reid et al. |
| 2019/0310242 | A1 | 10/2019 | Reid et al. |
| 2021/0079460 | A1 | 3/2021 | Reid et al. |
| 2022/0064724 | A1 | 3/2022 | Reid et al. |

FOREIGN PATENT DOCUMENTS

| | | | |
|---|---|---|---|
| JP | H11-178575 | 7/1999 | |
| JP | 2002-325581 | 11/2002 | |
| JP | 2005-257687 A | 9/2005 | |
| JP | 2006-119140 A | 5/2006 | |
| JP | 2010-524436 A | 7/2010 | |
| JP | 2010-539966 | 12/2010 | |
| JP | 2014-531901 A | 12/2014 | |
| WO | WO 2000/028312 | 5/2000 | |
| WO | WO 2000/039333 A1 | 7/2000 | |
| WO | WO 2000/079257 A1 | 12/2000 | |
| WO | WO 2002/42496 | 5/2002 | |
| WO | WO 2005/124888 | 12/2005 | |
| WO | WO 2006-028503 A2 | 3/2006 | |
| WO | WO 2006/100484 | 9/2006 | |
| WO | WO 2007/117832 A2 | 10/2007 | |
| WO | WO 2007/137225 A2 | 11/2007 | |
| WO | WO 2008/092760 A1 | 8/2008 | |
| WO | WO 2008/102120 A1 | 8/2008 | |
| WO | WO 2008/102121 | 8/2008 | |
| WO | WO 2008/124107 | 10/2008 | |
| WO | WO 2009/035647 | 3/2009 | |
| WO | WO 2009/077734 A2 | 6/2009 | |
| WO | WO 2010/004265 | 1/2010 | |
| WO | WO 2010/004273 | 1/2010 | |
| WO | WO 2010/034018 A2 | 3/2010 | |
| WO | WO 2010/053820 A1 | 5/2010 | |
| WO | WO-2010055307 A1 * | 5/2010 | ........... C07K 14/245 |
| WO | WO 2010/086603 | 8/2010 | |
| WO | WO 2010/086622 | 8/2010 | |
| WO | WO 2010/109197 | 9/2010 | |
| WO | WO 2010/117470 A2 | 10/2010 | |
| WO | WO 2010/122293 | 10/2010 | |
| WO | WO 2011/046706 A1 | 4/2011 | |
| WO | WO 2011/067559 | 6/2011 | |
| WO | WO 2012/005857 A1 | 1/2012 | |
| WO | WO 2012/021149 A1 | 2/2012 | |
| WO | WO 2012/033524 A2 | 3/2012 | |
| WO | WO 2012/107778 A2 | 8/2012 | |
| WO | WO 2012/109483 A2 | 8/2012 | |
| WO | WO 2012/135658 A2 | 10/2012 | |
| WO | WO 2012/138357 | 10/2012 | |
| WO | WO 2012/164270 A1 | 12/2012 | |
| WO | WO 2013/014451 | 1/2013 | |
| WO | WO 2013/041878 A1 | 3/2013 | |
| WO | WO 2013/057495 A2 | 4/2013 | |
| WO | WO 2013/098561 A1 | 7/2013 | |
| WO | WO 2013/098562 A2 | 7/2013 | |
| WO | WO 2013/109970 | 7/2013 | |
| WO | WO 2013/121224 | 8/2013 | |
| WO | WO 2013/123379 | 8/2013 | |
| WO | WO 2013/153359 | 10/2013 | |
| WO | WO 2013/159042 | 10/2013 | |
| WO | WO 2013/185137 A1 | 12/2013 | |
| WO | WO 2014/013259 | 1/2014 | |
| WO | WO 2014/013260 | 1/2014 | |
| WO | WO 2014/013262 | 1/2014 | |
| WO | WO 2014/064443 | 5/2014 | |
| WO | WO 2014/064444 | 5/2014 | |
| WO | WO 2014/096830 A1 | 6/2014 | |

OTHER PUBLICATIONS

Alcock et al., Time-series Similarity Queries Employing a Feature-Based Approach. Proceedings of the 7th Hellenic Conference on Informatics (HCI '99); University of Ioannina, Greece, pp. 1-9, Aug. 26-29, 1999.

Altschul et al., Basic local alignment search tool. J Mol Biol. Oct. 5, 1990;215(3):403-10.

Altschul, A protein alignment scoring system sensitive at all evolutionary distances. J Mol Evol. Mar. 1993;36(3):290-300.

Ashkenasy et al., Recognizing a single base in an individual DNA strand: a step toward DNA sequencing in nanopores. Angew Chem Int Ed Engl. Feb. 18, 2005;44(9):1401-4.

Batzoglou, Algorithmic challenges in mammalian whole-genome sequence assembly. In: Encyclopedia of genomics, proteomics and bioinformatics. John Wiley and Sons, New York. 2005.

(56) References Cited

OTHER PUBLICATIONS

Bell et al., DNA origami nanopores. Nano Lett. Jan. 11, 2012;12(1):512-7. doi: 10.1021/nl204098n. Epub Dec. 29, 2011.

Bokhari et al., A parallel graph decomposition algorithm for DNA sequencing with nanopores. Bioinformatics. Apr. 1, 2005;21(7):889-96. Epub Nov. 11, 2004.

Boufounos et al., Basecalling using hidden Markov models. Journal of the Franklin Institute, vol. 341 :23-36 (2004).

Braha et al., Designed protein pores as components for biosensors. Chem Biol. Jul. 1997;4(7):497-505.

Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.

Case 1:17-cv-00275-LPS Document 18. Notice of subsequent events relating to Oxford's motion to dismiss (D.I. 9). Oct. 18, 2017.

Case 1:17-cv-00275-LPS Document 19. Oxford Nanopore Technologies, Inc.'s response to Pacific Biosciences of California, Inc.'s notice of subsequent events. Oct. 24, 2017.

Case 1:17-cv-00275-RGA Document 10. Oxford's opening brief in support of its motion to dismiss PacBio's complaint for patent infringement. May 8, 2017.

Case 1:17-cv-00275-RGA Document 14. PacBio's response to Oxford's motion to dismiss. Jun. 5, 2017.

Case 1:17-cv-00275-RGA Document 16. Oxford's reply brief in support of its motion to dismiss PacBio's complaint for patent infringement. Jun. 26, 2017.

Case 1:17-cv-01353-LPS Document 13. First Amended Complaint for Patent Infringement. Nov. 30, 2017.

Case 1:17-cv-01353-LPS Document 15. Plaintiff's response to Oxford Nanopore Techologies, Inc.'s Motion to Dismiss and Request for Scheduling Conference. Nov. 30, 2017.

Case 1:17-cv-01353-RGA Document 10. Oxford's opening brief in support of its motion to partially dismiss Pacbio's complaint for patent infringement. Nov. 16, 2017.

Chao et al., Constrained sequence alignment. Bull Math Biol. May 1993;55(3):503-24.

Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.

Dahl et al., Direct observation of translocation in individual DNA polymerase complexes. J Biol Chem. Apr. 13, 2012;287(16):13407-21. doi:10.1074/jbc.M111.338418. Epub Feb. 29, 2012.

Derrington et al., Nanopore DNA sequencing with MspA. Proc Natl Acad Sci U S A. Sep. 14, 2010;107(37):16060-5. doi: 10.1073/pnas.1001831107.

Devereux et al., A comprehensive set of sequence analysis programs for the VAX. Nucleic Acids Res. Jan. 11, 1984;12(1 Pt 1):387-95.

Edgar, Muscle: multiple sequence alignment with high accuracy and high throughput. Nucleic Acids Res. Mar. 19, 2004;32(5):1792-7. Print 2004.

EP Communication pursuant to Rule 114(2) EPC for application No. 13706058.8 dated Oct. 19, 2017.

Ervin et al., Simultaneous alternating and direct current readout of protein ion channel blocking events using glass nanopore membranes. Anal Chem. Mar. 15, 2008;80(6):2069-76. doi: 10.1021/ac7021103. Epub Feb. 23, 2008.

Fariselli et al., A new decoding algorithm for hidden Markov models improves the prediction of the topology of all-beta membrane proteins. BMC Bioinformatics. Dec. 1, 2005;6 Suppl 4:S12.

Gonzalez-Perez et al., Biomimetic triblock copolymer membrane arrays: a stable template for functional membrane proteins. Langmuir. Sep. 15, 2009;25(18):10447-50. doi: 10.1021/la902417m.

Gordon, Classification. 2nd edition. Chapman and Hall/CRC. 69-109. 1999.

Hall et al., Hybrid pore formation by directed insertion of α-haemolysin into solid-state nanopores. Nat Nanotechnol. Dec. 2010;5(12):874-7. doi: 10.1038/nnano.2010.237. Epub Nov. 28, 2010.

He et al., Controlling DNA translocation through gate modulation of nanopore wall surface charges. ACS Nano. Jul. 26, 2011;5(7):5509-18. doi: 10.1021/nn201883b. Epub Jun. 17, 2011.

Healy, Nanopore-based single-molecule DNA analysis. Nanomedicine (Lond). Aug. 2007;2(4):459-81.

Hein et al., Statistical alignment:computational properties, homology testing and goodness-of-fit. J Mol Biol. Sep. 8, 2000;302(1):265-79.

Heron et al., Simultaneous measurement of ionic current and fluorescence from single protein pores. J Am Chem Soc. Feb. 11, 2009;131(5):1652-3. doi: 10.1021/ja808128s.

Higgins et al., CLUSTAL: a package for performing multiple sequence alignment on a microcomputer. Gene. Dec. 15, 1988;73(1):237-44.

Ivanov et al., DNA tunneling detector embedded in a nanopore. Nano Lett. Jan. 12, 2011;11(1):279-85. doi: 10.1021/nl103873a. Epub Dec. 6, 2010.

Karp et al., Efficient randomized pattern-matching algorithms. IBM J. Res. Development. 1987;31(2):249-260.

Kasianowicz et al., Nanoscopic porous sensors. Annu Rev Anal Chem (Palo Alto Calif). 2008;1:737-66. doi: 10.1146/annurev.anchem.1.031207.112818.

Kaxiras et al. Multiscale simulations of complex systems: computation meets reality. Sci Model Simul. 2008; 15:59-65.

Kent, BLAT—the BLAST-like alignment tool. Genome Res. Apr. 2002;12(4):656-64.

Khreich et al., A survey of techniques for incremental learning of HMM parameters. J Info Sciences. Aug. 2012;197:105-130.

Kowalczyk et al., Slowing down DNA translocation through a nanopore in lithium chloride. Nano Lett. Feb. 8, 2012;12(2):1038-44. doi: 10.1021/nl204273h. Epub Jan. 27, 2012.

Lam et al., HMMCONVERTER 1.0: a toolbox for hidden Markov models. Nucleic Acids Res. Nov. 2009;37(21):e139. doi: 10.1093/nar/gkp662.

Lathrop et al., Monitoring the escape of DNA from a nanopore using an alternating current signal. J Am Chem Soc. Feb. 17, 2010;132(6):1878-85. doi:10.1021/ja906951g.

Liang et al., Bayesian Basecalling for DNA Sequence Analysis using Hidden Markov Models. Proceedings of 2006 IEEE Conference on Information Sciences and Systems, CISS, pp. 1599-1604 (2006).

Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.

Luan et al., Base-by-base ratcheting of single stranded DNA through a solid-state nanopore. Phys Rev Lett. Jun. 11, 2010;104(23):238103. Epub Jun. 10, 2010.

Luan et al., Control and reversal of the electrophoretic force on DNA in a charged nanopore. J Phys Condens Matter. Nov. 17, 2010;22(45):454123. doi:10.1088/0953-8984/22/45/454123. Epub Oct. 29, 2010.

Manrao et al., Reading DNA at single-nucleotide resolution with a mutant MspA nanopore and phi29 DNA polymerase. Nat Biotechnol. Mar. 25, 2012;30(4):349-53. doi: 10.1038/nbt.2171.

Montal et al., Formation of bimolecular membranes from lipid monolayers and a study of their electrical properties. Proc Natl Acad Sci U S A. Dec. 1972;69(12):3561-6.

Nakane et al. Nanopore sensors for nucleic acid analysis. J. Phys.: Condens. Matter 15 (2003) R1365-R1393.

Olasagasti et al., Replication of individual DNA molecules under electronic control using a protein nanopore. Nat Nanotechnol. Nov. 2010;5(11):798-806. doi: 10.1038/nnano.2010.177. Epub Sep. 26, 2010.

Quinlan et al., C.45: Programs for Machine Learning. Morgan Kaufmann Publishers, ISBN 1-55860-238-0. Ed.:Langley. 1-114. 1993.

Schneider et al., DNA sequencing with nanopores. Nat Biotechnol. Apr. 10, 2012;30(4):326-8. doi: 10.1038/nbt.2181.

Soni et al., Synchronous optical and electrical detection of biomolecules traversing through solid-state nanopores. Rev Sci Instrum. Jan. 2010;81(1):014301. doi: 10.1063/1.3277116.

(56) References Cited

OTHER PUBLICATIONS

Stoddart et al., Multiple base-recognition sites in a biological nanopore: two heads are better than one. Angew Chem Int Ed Engl. 2010;49(3):556-9. doi: 10.1002/anie.200905483.

Stoddart et al., Nucleobase recognition in ssDNA at the central constriction of the alpha-hemolysin pore. Nano Lett. Sep. 8, 2010;10(9):3633-7. doi: 10.1021/nl101955a.

Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.

Suzuki et al., A New Hmnet Construction Algorithm Requiring No Contextual Factors. IEICE. Jun. 1995;E78:662-668.

Takami et al., Automatic Generation of Hidden Markov Networks by a Successive State Splitting Algoritm. IEICE. 1993;J76:2155-2164.

Thompson et al., CLUSTAL W: improving the sensitivity of progressive multiple sequence alignment through sequence weighting, position-specific gap penalties and weight matrix choice. Nucleic Acids Res. Nov. 11, 1994;22(22):4673-80.

Timp et al., DNA base-calling from a nanopore using a Viterbi algorithm. Biophys J. May 16, 2012;102(10):L37-9. doi:10.1016/j.bpj.2012.04.009. Epub May 15, 2012.

United States District Court for the District of Delaware Order. *Pacific Biosciences of California, Inc.* v. *Oxford Nanopore Technolgoies, Inc.* Civil Action No. 17-275-RGA. Nov. 9, 2017.

United States Patent and Trademark Office. *Oxford Nanopore Technologies Inc.* Petition v *Pacific Biosciences of California, Inc.* for U.S. Pat. No. 9,546,400. Inter Partes Review of claims 1-15. 81 pages. Mar. 15, 2018.

Warren et al., Assembling millions of short DNA sequences using SSAKE. Bioinformatics. Feb. 15, 2007;23(4):500-1. Epub Dec. 8, 2006.

Winters-Hilt et al., A novel, fast, HMM—with—Duration implementation—for application with a new, pattern recognition informed, nanopore detector. BMC Bioinformatics. Nov. 1, 2007;8 Suppl 7:S19.

Winters-Hilt et al., Highly accurate classification of Watson-Crick basepairs on termini of single DNA molecules. Biophys J. Feb. 2003;84(2 Pt 1):967-76.

Winters-Hilt, Machine learning methods for channel current cheminformatics, biophysical analysis, and bioinformatics. University of California Santa Cruz. Mar. 2003. Dissertation. 176 pages.

Zeng et al., PyroHMMvar: a sensitive and accurate method to call short indels and SNPs for Ion Torrent and 454 data. Bioinformatics. Nov. 15, 2013;29(22):2859-68. doi: 10.1093/bioinformatics/btt512. Epub Aug. 31, 2013.

Zerbino et al., Velvet: algorithms for de novo short read assembly using de Bruijn graphs. Genome Res. May 2008;18(5):821-9. doi: 10.1101/gr.074492.107. Epub Mar. 18, 2008.

Zhu et al., Bayesian adaptive sequence alignment algorithms. Bioinformatics. 1998;14(1):25-39.

[No Author Listed], Chapter 2: Polymerizer Module from Polymer. 1997. 14 pages. www.esi.umontreal.ca/accelrys/materials/insight400P/polymer/02_Polym.doc.html, Accessed May 17, 2021.

Ainsleigh et al., Hidden Gauss-Markov Models for Signal Classification. IEEE Trans Sig Proc. Jun. 2002;50(6):1355-1367.

Bates et al., Dynamics of DNA molecules in a membrane channel probed by active control techniques. Biophys J. 2003;84(4):2366-2372. doi:10.1016/S0006-3495(03)75042-5.

Cabello-Aguilar et al., Experimental and simulation studies of unusual current blockade induced by translocation of small oxidized PEG through a single nanopore. Phys Chem Chem Phys. Sep. 7, 2014;16(33):17883-92. doi: 10.1039/c4cp01954g.

Churbanov et al., Duration learning for analysis of nanopore ionic current blockades. BMC Bioinformatics. Nov. 1, 2007;8 Suppl 7(Suppl 7):S14. doi: 10.1186/1471-2105-8-S7-S14.

Fennouri et al., Single molecule detection of glycosaminoglycan hyaluronic acid oligosaccharides and depolymerization enzyme activity using a protein nanopore. ACS Nano. Nov. 27, 2012;6(11):9672-8. doi: 10.1021/nn3031047. Epub Oct. 17, 2012.

Jain et al., Improved data analysis for the MinION nanopore sequencer. Nat Methods. Apr. 2015; 12(4): 351-356. EPub Feb. 16, 2015. doi: 10.1038/nmeth.3290. Author Manuscript.

Loose et al., Real-time selective sequencing using nanopore technology. Nat Methods. Sep. 2016; 13(9): 751-754. EPub Jul. 25, 2016. doi: 10.1038/nmeth.3930.

Mikheyev et al., A first look at the Oxford Nanopore MinION sequencer. Mol Ecol Resour. Nov. 2014;14(6):1097-102. doi: 10.1111/1755-0998.12324. Epub Sep. 24, 2014.

Pylkkönen et al., Duration Modeling Techniques for Continuous Speech Recognition. Eighth International Conference on Spoken Language Processing. 2004. 4 pages.

Branton et al., The potential and challenges of nanopore sequencing. Nat Biotechnol. Oct. 2008;26(10):1146-53. doi: 10.1038/nbt.1495.

Hornblower et al., Single-molecule analysis of DNA-protein complexes using nanopores. Nat Methods. Apr. 2007;4(4):315-7. doi: 10.1038/nmeth1021. Epub Mar. 4, 2007.

Muzard et al., DNA translocation and unzipping through a nanopore: some geometrical effects. Biophys J. May 19, 2010;98(10):2170-8. doi: 10.1016/j.bpj.2010.01.041.

Howorka et al., Nanopore analytics: sensing of single molecules. Chem Soc Rev. Aug. 2009;38(8):2360-84. doi: 10.1039/b813796j. Epub Jun. 15, 2009.

Panwar et al., Enzyme-modulated DNA translocation through a nanopore. J Am Chem Soc. Dec. 30, 2009;131(51):18563-70. doi: 10.1021/ja904047q.

\* cited by examiner

Time (s)

ANALYSIS OF MEASUREMENTS OF A POLYMER

This Application is a Continuation under 35 U.S.C. § 120 of U.S. application Ser. No. 14/379,242, filed Aug. 15, 2014, entitled "ANALYSIS OF MEASUREMENTS OF A POLYMER", which is a national stage filing under 35 U.S.C. 371 of International Patent Application Serial No. PCT/GB2013/050381, filed Feb. 18, 2013, entitled "ANALYSIS OF MEASUREMENTS OF A POLYMER", which claims priority to U.S. Application Ser. No. 61/599,573, filed Feb. 16, 2012, entitled "ANALYSIS OF MEASUREMENTS OF A POLYMER". The entire content of each of these applications is incorporated herein by reference in its entirety.

The present invention relates generally to the field of analysing measurements of a polymer comprising polymer units, for example but without limitation a polynucleotide, made during translocation of the polymer through a nanopore.

A nanopore measurement is typically made by restricting the flow of material between two pools of solution using a membrane. An aperture is provided within that membrane to allow the transfer of material from one pool of solution to another. The aperture has at least one dimension on the nanometre scale. As the material is translocated through the pore, measurements are made of that material. The most commonly used setup relies on the application of an applied potential to drive molecular species through the nanopore. An electrode is placed in each solution volume and the solution contains an electrolyte, typically a salt, such as 1 M NaCl. The applied potential across the electrodes also drives the electrolyte through the pore and generates a current. When material passes through the pore it modifies the flow of ions which is directly observed in the current measurement. The degree of current block and the duration the material spends in the nanopore are indicative of its identity.

The original concept of analysing a polymer by passing it through a nanopore was proposed by Branton et al. (U.S. Pat. No. 5,795,782) in 1996. In this case, a DNA molecule is passed through a nanopore embedded in a lipid membrane. An electrode is placed on each side of the membrane and an applied potential is used to drive the DNA molecule from one side of the membrane to the other. During the translocation of the DNA molecule, the trans-membrane current through the pore is measured. It was shown that different sequences of DNA would give rise to different observed currents as the DNA passes through the nanopore.

These early experiments were performed using homopolymers of nucleotides where the polymer freely translocates the nanopore. In these experiments, the rate of polymer translocation is very fast (~5 μs/base) causing the characteristics of individual nucleotides within the polymer to be difficult to determine.

To overcome the limitations of rapid DNA translocation, Branton et al. disclose the use of a polymerase to control the speed of DNA translocation through the nanopore. This elegant solution has been adopted and adapted by many researchers in the field which has led to a number of publications. The basic concept is to provide a ratchet to the motion of the polymer, which could encompass a molecular motor or a molecular brake.

Early work concentrated on the use of polymerases to control the motion of DNA. A number of studies were performed using Klenow fragment, but these experiments were limited by the short duration of the DNA-enzyme complex on top of the nanopore. A number of schemes were developed to compensate for this weak binding (e.g. see Olasagasti et al., Nat Nanotechnol. 2010 November; 5(11): 798-806, Ashkenasy et al., Angew Chem Int Ed Engl. 2005 Feb. 18; 44(9):1401-4).

In 2010, it was disclosed by Akeson et al. that Phi29 DNA polymerase (DNAP) could function on top of a nanopore (e.g. see Lieberman et al., J Am Chem Soc. 2010 Dec. 22; 132(50):17961-72, 61/402,903). The strength of the Phi29 DNAP binding to the template DNA was sufficient to allow multiple enzyme cycles to be performed on top of the nanopore, thus allowing the DNA to be pulled through the nanopore in a ratcheted fashion. The paper also revealed that Phi29 DNAP could be used to control DNA motion through the nanopore under conditions where the enzyme motion was inhibited. In these conditions, the $Mg^{2+}$, which is essential to enzymatic action, is effectively removed through the addition of the metal chelator ethylenediaminetetraacetic acid (EDTA). The applied potential provides the force on the DNA strand and the Phi29 DNAP limited the "unzipping" of the strand through the pore. This work showed that enzymes in nanopore systems could either function as molecular motors or as molecular breaks.

In addition to using polymerases as molecular ratchets, it has been demonstrated that some helicase families can be used to provide controlled movement of polynucleotides through a nanopore (e.g. see U.S. 61/549,998 (N115020), U.S. 61/581,332 (N115505), U.S. 61/581,340 (N115506)). Helicases have a number of properties that make them suitable for a nanopore system.

An alternative method of slowing down translocation of a target single stranded DNA is to hybridise additional sections of ssDNA (hyb-DNA) along the length of the target strand. The target strand of DNA is rapidly fed through the pore under an applied potential. Once a double stranded section of the strand reaches the constriction of the nanopore, the translocation of the strand is halted, allowing the current to be read with the polymer at a fixed position. The hyb-DNA section is un-hybridised by the force of the applied field, and the target DNA strand continues to translocate the nanopore until another hyb-DNA is encountered. In this way, the current signatures for the DNA strand at a number of fixed positions are obtained. By employing complex sample preparation techniques, Derrington et al. propose a method of sequencing a strand of DNA using this approach.

The data generated from these approaches shares key features; the translocation of DNA occurs in discreet stages where each stage represents a position of the polymer in the nanopore and each polymer position has a characteristic current level. The current levels can sometimes exhibit fluctuations, termed variance. These features result in signals that take the form of "noisy step waves".

More generally some property of the system depends on the polymer units in the nanopore, and measurements of that property are taken. For example, a measurement system may be created by placing a nanopore in an insulating membrane and measuring voltage-driven ionic transport through the nanopore in the presence of analyte molecules. The controlled movement of polymer through a nanopore results in a number of distinct levels of measurement that are indicative of the polymer sequence.

In previous developments, the focus has been on determining the underlying sequence of the polymer. Generally in these approaches, each of the states within the signal have been analysed independently by comparing the current levels of these states to known current levels from reference data. This process converts the current signal into an estimate of polymer sequence. An alternative way of saying this is that the process converts the information from signal space to sequence space. However, there are practical difficulties in developing a measurement system that can reliably determine the sequence.

It is typical of many types of measurement system, including the majority of currently known nanopores, for the value of each measurement to be dependent on a group of k polymer units, where k is a plural integer, hereinafter referred to as a 'k-mer'. This is because more than one polymer unit contributes to the observed ion current and might be thought of conceptually as the measurement system having a "blunt reader head" that is bigger than the polymer unit being measured. In such a situation, the number of different k-mers to be resolved increases to the power of k. For example, if there are n possible polymer units, the number of different k-mers to be resolved is $n^k$. While it is desirable to have clear separation between measurements for different k-mers, it is common for some of these measurements to overlap. Especially with high numbers of k-mers, it can become difficult to resolve the measurements produced by different k-mers, to the detriment of deriving information about the polymer, for example an estimate of the underlying sequence of polymer units.

Much research has aimed at design of a measurement system that provides resolvable measurements that are dependent on a single polymer unit. However, this has proved difficult in practice, for example due to variation in measurements that can arise to varying extents from inherent variation in the underlying physical or biological system and/or measurement noise that is inevitable due to the small magnitude of the properties being measured. Other work has accepted measurements that are dependent on k-mers, but has aimed at design of a measurement system in which the measurements from different k-mers are resolvable from each other. However practical limitations mean again that this is very difficult. Distributions of signals produced by some different k-mers can often overlap.

According to the present invention, there is provided a method of analyzing a time-ordered series of measurements of a polymer made during translocation of the polymer through a nanopore, wherein the measurements are dependent on the identity of k-mers in the nanopore, a k-mer being k polymer units of the polymer, where k is a positive integer, the method comprising:

deriving, from the series of measurements, a feature vector of time-ordered features representing characteristics of the measurements; and determining similarity between the derived feature vector and at least one other feature vector.

Although previous research has tried to derive the exact sequence from the measurements, the present invention makes use of an appreciation that many applications do not require the exact polymer sequence to be assigned. These include a significant number of diagnostic, clinical, scientific, genetic applications where the desired result can be obtained cheaply, quickly, and to a higher degree of accuracy without resorting to sequence information. In particular the present invention involves derivation of a feature vector of time-ordered features representing characteristics of the measurements. Similarity between the derived feature vector and at least one other feature vector is then determined which provides information that is useful in many applications.

Consequently, the present invention does not require the assignment of polymer sequence, i.e. there is not necessarily a conversion of the measurement signal into sequence space. This provides useful analysis of the polymer in many applications, but reduces the burden on operation of the measurement system, because it is not necessary to resolve every single polymer unit in the sequence. This reduction on the constraints of the measurement system also increases the range of measurements systems. This may allow the use of a measurement system that is easier to design or operate, or may allow the use of a measurement system that is specifically adapted to analyse a particular characteristic of the polymer, even without being able to provide complete sequence information.

An underlying feature of the invention is the conversion of the raw signal, that is the time-ordered series of measurements into a feature vector of time-ordered features. The series of measurements are derived as the polymer translocates through the nanopore and so provide information on the overall sequence, even if this is not complete. The derivation of the feature vector provides a representation which is also time-ordered but with a reduced data set. This feature vector may be thought of as a "signature" of the polymer. The feature vector is then compared to at least one other feature vector to determine the similarity. The at least one other feature vector may be, for example, a feature vector stored in a memory or another feature vector derived in the same manner. Based on the similarity, characteristics of the polymer may be derived.

With some signals, there is sufficient resolution of each k-mer that groups of consecutive measurements are dependent on a respective k-mer that is different for each group. In this case, the step of deriving a feature vector may comprise identifying groups of consecutive measurements, and, in respect of each group, deriving values of one or more features that represent characteristics of the measurements of the group. For example, the features may comprise: an average of the group of measurements; the period of the group of measurements; a variance of the group of measurements; the distribution of the group of measurements; or any combination thereof.

The present invention is also applicable to signals with a lesser resolution, such that some k-mers may provide only a single measurement or no measurement at all.

As mentioned above, in some cases the derived feature vector may be compared with at least one other feature vector stored in a memory in respect of at least one class. In this case the similarity may be determined between between the entirety or part of the derived feature vector and the entirety of the at least one other feature vector stored in the memory, or alternatively between the entirety or part of the derived feature vector and a part of the at least one other feature vector stored in the memory.

The method may further comprise classifying the polymer from which the derived feature vector is derived as belonging to a said class on the basis of the determined similarity. This provides for identification of the polymer under investigation.

The at least one other feature vector stored in the memory may be selected depending upon the polymer to be measured, or alternatively a library of plural other feature vectors stored in the memory may be used.

In some applications, a combined feature vector may be obtained from two or more feature vectors having overlapping regions wherein the similarity of the derived feature vector is determined between the combined feature vector. A non-overlapping region of the combined feature vector may be used to determine similarity between the derived feature vector, for example to identify a particular localised region of the derived feature vector.

Thus the method may be used to determine similarity between continuous or non-continuous regions of a derived feature vector and one or more feature vectors.

In some applications, plural parts of the derived feature vector may be compared all, parts or plural parts of stored feature vectors.

As mentioned above, in other cases the derived feature vector may be compared with at least one other feature vector that is a feature vector derived using the same method. This provides for identification of characteristics of plural polymers that are under investigation, relative to each other. In this case, the method may further comprise identifying clusters of similar feature vectors as a class and classifying the polymers from which the feature vectors are derived as belonging to an identified class.

In one example, where there are plural other feature vectors derived using the same method, the method may further comprise identifying feature vectors that are derived from polymers that are fragments of a common polymer on the basis of similarity in overlapping parts of the feature vectors.

Where polymers are classified, the method may further comprise counting the numbers of feature vectors belonging to different classes. This provides for analysis of a population of polymers under investigation.

Where polymers are classified, the method may further comprise identifying localized regions where the derived feature vector is dissimilar to a feature vector in respect of the class in which the polymer is classified as belonging.

In a similar technique where the polymer has an expected identity, the derived feature vector may be compared to a feature vector stored in a memory and the determination of similarity comprises determining localized regions where the derived feature vector is dissimilar to the at least one other feature vector stored in the memory.

Such identification of localized regions where the derived feature vector is dissimilar to what is expected provides an analysis technique that is very powerful in many applications where change in relatively small regions of long sequences of polymers is significant. One example of such a technique is to identify mutations in a polymer that is a polynucleotide.

The method may be performed on a series of measurements that has been previously made. Alternatively, the method may further comprise: translocating the polymer through a nanopore; and making the continuous series of measurements of the polymer.

The method of analysing the series of measurements may be used in a method of estimating the presence, absence or amount of a target polymer based on the analysis.

In that case, the polymer may comprise a mixture of two or more polymers and the relative amounts of one or more polymers may be determined.

The method of estimating the presence, absence or amount of a target polymer may be applied to a polymer analyte in a method comprising: fragmenting the polymer analyte into polymers; and performing the method of estimating on the fragmented polymers. Where the polymer is a polynucleotide, and the polymer units are nucleotides, the polymer analyte may be fragmented by a restriction enzyme.

The method of analysing the series of measurements may be applied in a method of determining an alteration in a polymer, comprising: translocating a polymer through a nanopore repeatedly over a period of time; during each translocation, making a continuous series of measurements of the polymer; analysing each series of measurements. In this case, the step of determining similarity between the derived feature vector and at least one other feature vector may comprise either (a) determining similarity between the derived feature vector derived from each series of measurements and the same at least one other feature vector or (b) determining similarity between all the derived feature vectors derived from the series of measurements.

Where the polymer is a polynucleotide, and the polymer units are nucleotides, the method may be used to determine the presence of a modified base or a point mutation.

Generally, the methods may be used to guide a therapy or diagnosis or to identify an individual.

The present invention has numerous applications. Some non-limitative examples or applications are as follows.

This invention can be applied to single molecule label free detection systems for analysis of polymers, for example a nanopore system. It is common for such systems to comprise a recognition element that is influenced by more than one monomer units at a given polymer position. In these systems, extracting the relationship between measurement and polymer sequence may be challenging or resource demanding.

This invention can be applied to any polymer analysis system where a polymer signature is indicative of a characteristic of that polymer and where the exact polymer sequence does not have to be known to determine said characteristic. Examples include but are not limited to: detection of single nucleotide polymorphisms (SNPs), presence or absence of specific sequences, grouping and counting of polymer sequences, design of labels and biomarkers, and identification of modified or damaged DNA.

The method may be used for example to determine the presence, absence or amount of a target polymer analyte in a sample. The method may be used to measure an amount with respect to a threshold. The method may be used to determine the relative amounts of one or more target polymers in a mixture of polymers.

The method may be used to guide a therapy or diagnosis based upon analysis of a single sample. Alternatively the method may be carried out plural times over a period for example to monitor progression of a disease or improvement of an individual. The method may be used to monitor an efficacy of treatment, for example where used as a theranostic.

The method may be used in forensic applications for example to detect SNPs in mitochondrial DNA for DNA profiling of individuals, for genetic fingerprinting of individuals, for example by determining the presence of short tandem repeats, variable tandem repeats and the like.

All the methods may be performed without estimating the sequence of polymer units of the polymer.

To allow better understanding, embodiments of the present invention will now be described by way of non-limitative example with reference to the accompanying drawings, in which.

Figure 1:
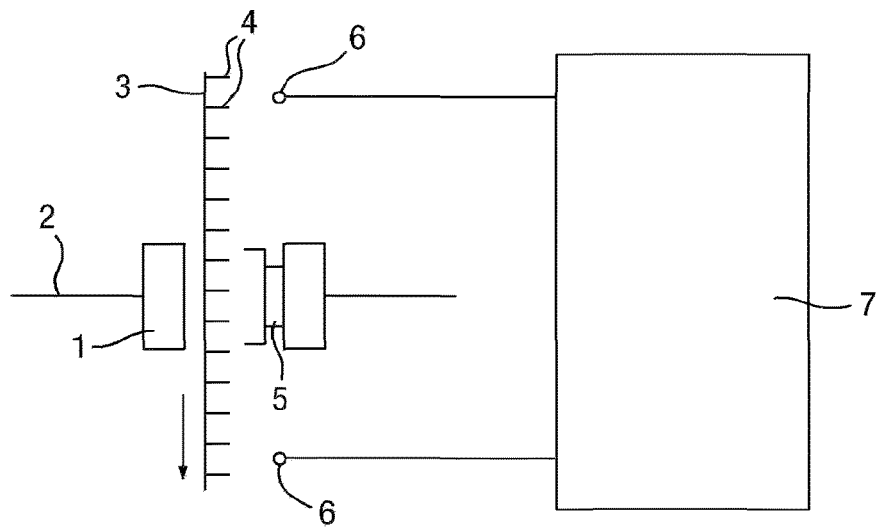
FIG. 1 is a schematic diagram of a measurement system comprising a nanopore.

Polymers that may be applied are as follows.

The polymer may be a biological polymer. The polymer may be natural or synthetic. The polymer may be a polynucleotide (or nucleic acid), a polypeptide such as a protein, a polysaccharide, or any other polymer. In the case of a polypeptide, the polymer units may be amino acids that are naturally occurring or synthetic. In the case of a polysaccharide, the polymer units may be monosaccharides.

Polynucleotides that may be applied are as follows.

A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the target polynucleotide can be oxidized or methylated. One or more nucleotides in the target polynucleotide may be damaged. One or more nucleotides in the target polynucleotide may be modified, for instance with a label or a tag. The target polynucleotide may comprise one or more spacers.

A nucleotide typically contains a nucleobase, a sugar and at least one phosphate group. The nucleobase is typically heterocyclic. Nucleobases include, but are not limited to, purines and pyrimidines and more specifically adenine, guanine, thymine, uracil and cytosine. The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), 5-methylcytidine monophosphate, 5-methylcytidine diphosphate, 5-methylcytidine triphosphate, 5-hydroxymethylcytidine monophosphate, 5-hydroxymethylcytidine diphosphate, 5-hydroxymethylcytidine triphosphate, cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP), 5-methyl-2'-deoxycytidine monophosphate, 5-methyl-2'-deoxycytidine diphosphate, 5-methyl-2'-deoxycytidine triphosphate, 5-hydroxymethyl-2'-deoxycytidine monophosphate, 5-hydroxymethyl-2'-deoxycytidine diphosphate and 5-hydroxymethyl-2'-deoxycytidine triphosphate. The nucleotides are preferably selected from AMP, TMP, GMP, UMP, dAMP, dTMP, dGMP or dCMP. The nucleotides may be abasic (i.e. lack a nucleobase). The nucleotides may contain additional modifications. In particular, suitable modified nucleotides include, but are not limited to, 2'amino pyrimidines (such as 2'-amino cytidine and 2'-amino uridine), 2'-hydroxyl purines (such as, 2'-fluoro pyrimidines (such as 2'-fluorocytidine and 2'fluoro uridine), hydroxyl pyrimidines (such as 5'-α-P-borano uridine), 2'-O-methyl nucleotides (such as 2'-O-methyl adenosine, 2'-O-methyl guanosine, 2'-O-methyl cytidine and 2'-O-methyl uridine), 4'-thio pyrimidines (such as 4'-thio uridine and 4'-thio cytidine) and nucleotides have modifications of the nucleobase (such as 5-pentynyl-2'-deoxy uridine, 5-(3-aminopropyl)-uridine and 1,6-diaminohexyl-N-5-carbamoylmethyl uridine).

A nucleotide may be abasic (i.e. lack a nucleobase).

The polynucleotide may be single stranded or double stranded. The polynucleotide may comprise one or more double stranded regions and one or more single regions. The polynucleotide can be a nucleic acid, such as deoxyribonucleic acid (DNA) or ribonucleic acid (RNA). The target polynucleotide can comprise one strand of RNA hybridized to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains.

The whole or only part of the target polynucleotide may be characterised using this method. The target polynucleotide can be any length. For example, the polynucleotide can be at least 10, at least 50, at least 100, at least 150, at least 200, at least 250, at least 300, at least 400 or at least 500 nucleotide pairs in length. The polynucleotide can be 1000 or more nucleotide pairs, 5000 or more nucleotide pairs in length or 100000 or more nucleotide pairs in length.

The target polynucleotide is present in any suitable sample. The invention is typically carried out on a sample that is known to contain or suspected to contain the target polynucleotide. Alternatively, the invention may be carried out on a sample to confirm the identity of one or more target polynucleotides whose presence in the sample is known or expected.

Samples that may be studied are as follows.

The sample may be a biological sample. The invention may be carried out in vitro on a sample obtained from or extracted from any organism or microorganism. The organism or microorganism is typically archaean, prokaryotic or eukaryotic and typically belongs to one the five kingdoms: plantae, animalia, fungi, monera and protista. The invention may be carried out in vitro on a sample obtained from or extracted from any virus. The sample is preferably a fluid sample. The sample may be solid or semi-solid in origin which is subsequently treated to provide a fluid sample. Examples of such are faecal, skin, tissue, hair, bone and muscle. The sample typically comprises a body fluid of the patient. The sample may be chosen for example from urine, blood, plasma, serum, lymph, saliva, interstitial fluid, tears, mucus or amniotic fluid. Typically, the sample is human in origin, but alternatively it may be from another mammal animal such as from commercially farmed animals such as horses, cattle, sheep or pigs or may alternatively be pets such as cats or dogs. Alternatively a sample of plant origin is typically obtained from a commercial crop, such as a cereal, legume, fruit or vegetable, for example wheat, barley, oats, canola, maize, soya, rice, bananas, apples, tomatoes, potatoes, grapes, tobacco, beans, lentils, sugar cane, cocoa, cotton.

The sample may be a non-biological sample. The non-biological sample is preferably a fluid sample. Examples of a non-biological sample include surgical fluids, water such as drinking water, sea water or river water, and industrial samples such as reagents for laboratory tests, samples obtained from the synthesis of a polymer reagent.

The sample is typically processed prior to being assayed, for example by centrifugation or by passage through a membrane that filters out unwanted molecules or cells, such as red blood cells. The sample may be measured immediately upon being taken. The sample may also be typically stored prior to assay, preferably below −70° C.

The sample may also be subject to any of the processes, designs, or modifications presented in U.S. 61/490,860.

Membranes that may be used in a measurement system are as follows.

Any membrane may be used in accordance with the invention. Suitable membranes are well-known in the art. The membrane is preferably an amphiphilic layer. An amphiphilic layer is a layer formed from amphiphilic molecules, such as phospholipids, which have both hydrophilic and lipophilic properties. The amphiphilic layer may be a monolayer or a bilayer. The membrane may be a co-block polymer such as disclosed by (Gonzalez-Perez et al., Langmuir, 2009, 25, 10447-10450).

The membrane may be a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. Suitable amphiphilic layers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Methods for forming lipid bilayers are known in the art. Suitable methods are disclosed in the Example. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

In a preferred embodiment, the amphiphilic layer is formed as described in International Application No. PCT/GB08/004127 (published as WO 2009/077734).

In another preferred embodiment, the membrane is a solid state layer. A solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from monatomic layers, such as graphene, or layers that are only a few atoms thick. Suitable graphene layers are disclosed in International Application No. PCT/US2008/010637 (published as WO 2009/035647). The solid state membrane can also support a nanopore derived from biological material, non-limiting examples have been disclosed by Hall et al. (Nat Nanotechnol. 2010 December; 5(12):874-7) and Bell et al. (Nano Lett. 2012 Jan. 11; 12(1):512-7), and International Application No. PCT/US2011/039621 (published as WO/2012/005857).

The method is typically carried out using (i) an artificial amphiphilic layer comprising a pore, (ii) an isolated, naturally-occurring amphiphilic layer comprising a pore, or (iii) a cell having a pore inserted therein. The method is preferably carried out using an artificial amphiphilic layer. The bilayer may comprise other transmembrane and/or intramembrane proteins as well as other molecules in addition to the pore. Suitable apparatus and conditions are discussed below. The method of the invention is typically carried out in vitro.

Nanopores that may be applied are as follows.

The measurement system comprises a nanopore. The measurements are taken during translocation of the polymer through the nanopore. The translocation of the polymer through the nanopore generates a characteristic signal in the measured property that may be observed, and may be referred to overall as an "event".

The nanopore is a pore, typically having a size broadly speaking of the order of nanometres, that allows the passage of polymers therethrough. Herein, references to a "pore" mean a nanopore in this sense.

The nanopore may be a biological pore or a solid state pore.

A solid state pore, is typically an aperture in a solid state layer. A solid state pore may be used in combination with additional components which provide an alternative or additional measurement of the polymer such as tunnelling electrodes (Ivanov A P et al., Nano Lett. 2011 Jan. 12; 11(1): 279-85), or a field effect transistor (FET) device (International Application WO 2005/124888). Solid state pores may be formed by known processes including for example those described in WO 00/79257.

The nanopore is preferably a transmembrane protein pore. A transmembrane protein pore is a polypeptide or a collection of polypeptides that permits hydrated ions to flow from one side of a membrane to the other side of the membrane. In the present invention, the transmembrane protein pore is capable of forming a pore that permits hydrated ions driven by an applied potential to flow from one side of the membrane to the other. The transmembrane protein pore allows a polymer, such as DNA or RNA, to be moved through the pore.

The transmembrane protein pore may be a monomer or an oligomer. The pore is preferably made up of several repeating subunits, such as 6, 7 or 8 subunits. The pore is more preferably a heptameric or octameric pore.

The transmembrane protein pore typically comprises a barrel or channel through which the ions may flow. The subunits of the pore typically surround a central axis and contribute strands to a transmembrane β-barrel or channel or a transmembrane α-helix bundle or channel.

The barrel or channel of the transmembrane protein pore typically comprises amino acids that facilitate interaction with analyte, such as polymers, nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and polymers, nucleotides, polynucleotides or nucleic acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, α-toxins, such as α-hemolysin, anthrax toxin and leukocidins, and outer membrane proteins/porins of bacteria, such as *Mycobacterium smegmatis* porin (Msp), for example MspA, outer membrane porin F (OmpF), outer membrane porin G (OmpG), outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and outer membrane proteins, such as WZA and ClyA toxin. The transmembrane pore may be derived from Msp or from α-hemolysin (α-HL).

The transmembrane protein pore is preferably derived from Msp, preferably from MspA. Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Msp comprising at least one monomer that differs from the others. Preferably the pore is derived from MspA or a homolog or paralog thereof.

A monomer derived from Msp comprises the sequence shown in SEQ ID NO: 2 or a variant thereof. SEQ ID NO: 2 is the MS-(B1)8 mutant of the MspA monomer. It includes the following mutations: D90N, D91N, D93N, D118R, D134R and E139K. A variant of SEQ ID NO: 2 is a polypeptide that has an amino acid sequence which varies from that of SEQ ID NO: 2 and which retains its ability to form a pore. The ability of a variant to form a pore can be assayed using any method known in the art. For instance, the variant may be inserted into a lipid bilayer along with other appropriate subunits and its ability to oligomerise to form a pore may be determined. Methods are known in the art for inserting subunits into membranes, such as lipid bilayers. For example, subunits may be suspended in a purified form in a solution containing a lipid bilayer such that it diffuses to the lipid bilayer and is inserted by binding to the lipid bilayer and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

Over the entire length of the amino acid sequence of SEQ ID NO: 2, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et al (1984) Nucleic Acids Research 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (http://www.ncbi.nlm.nih.gov/).

SEQ ID NO: 2 is the MS-(B1)8 mutant of the MspA monomer. The variant may comprise any of the mutations in the MspB, C or D monomers compared with MspA. The mature forms of MspB, C and D are shown in SEQ ID NOs: 15 to 17. In particular, the variant may comprise the following substitution present in MspB: A138P. The variant may comprise one or more of the following substitutions present in MspC: A96G, N102E and A138P. The variant may comprise one or more of the following mutations present in MspD: Deletion of G1, L2V, E5Q, L8V, D13G, W21A, D22E, K47T, 149H, 168V, D91G, A96Q, N102D, S103T, V104I, S136K and G141A. The variant may comprise combinations of one or more of the mutations and substitutions from Msp B, C and D. The variant may comprise the mutation L88N. The variant of SEQ ID NO: 2 has the mutation L88N in addition to all the mutations of MS-B1 and is called MS-B2. The pore used in the invention may be MS-(B2)8 or MS-(B2C)8.

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 2 below. Where amino acids have similar polarity, this can also be determined by reference to the hydropathy scale for amino acid side chains in Table 3.

TABLE 2

Chemical properties of amino acids:

| | | | |
|---|---|---|---|
| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged(+) | Trp | aromatic, hydrophobic, neutral |
| Leu | aliphatic, hydrophobic, neutral | Tyr | aromatic, polar, hydrophobic |

TABLE 3

Hydropathy scale:

| Side Chain | Hydropathy |
|---|---|
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may include fragments of SEQ ID NO: 2. Such fragments retain pore forming activity. Fragments may be at least 50, 100, 150 or 200 amino acids in length. Such fragments may be used to produce the pores. A fragment preferably comprises the pore forming domain of SEQ ID NO: 2. Fragments must include one of residues 88, 90, 91, 105, 118 and 134 of SEQ ID NO: 2. Typically, fragments include all of residues 88, 90, 91, 105, 118 and 134 of SEQ ID NO: 2.

One or more amino acids may be alternatively or additionally added to the polypeptides described above. An extension may be provided at the amino terminal or carboxy terminal of the amino acid sequence of SEQ ID NO: 2 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below.

As discussed above, a variant is a polypeptide that has an amino acid sequence which varies from that of SEQ ID NO: 2 and which retains its ability to form a pore. A variant typically contains the regions of SEQ ID NO: 2 that are responsible for pore formation. The pore forming ability of Msp, which contains a β-barrel, is provided by β-sheets in each subunit. A variant of SEQ ID NO: 2 typically comprises the regions in SEQ ID NO: 2 that form β-sheets. One or more modifications can be made to the regions of SEQ ID NO: 2 that form 3-sheets as long as the resulting variant retains its ability to form a pore. A variant of SEQ ID NO: 2 preferably includes one or more modifications, such as substitutions, additions or deletions, within its α-helices and/or loop regions.

The monomers derived from Msp may be modified to assist their identification or purification, for example by the addition of histidine residues (a hist tag), aspartic acid residues (an asp tag), a streptavidin tag or a flag tag, or by the addition of a signal sequence to promote their secretion from a cell where the polypeptide does not naturally contain such a sequence. An alternative to introducing a genetic tag is to chemically react a tag onto a native or engineered position on the pore. An example of this would be to react a gel-shift reagent to a cysteine engineered on the outside of the pore. This has been demonstrated as a method for separating hemolysin hetero-oligomers (Chem Biol. 1997 July; 4(7):497-505).

The monomer derived from Msp may be labelled with a revealing label. The revealing label may be any suitable label which allows the pore to be detected. Suitable labels include, but are not limited to, fluorescent molecules, radio-isotopes, e.g. 125I, 35S, enzymes, antibodies, antigens, polynucleotides and ligands such as biotin.

The monomer derived from Msp may also be produced using D-amino acids. For instance, the monomer derived from Msp may comprise a mixture of L-amino acids and D-amino acids. This is conventional in the art for producing such proteins or peptides.

The monomer derived from Msp contains one or more specific modifications to facilitate nucleotide discrimination. The monomer derived from Msp may also contain other non-specific modifications as long as they do not interfere with pore formation. A number of non-specific side chain modifications are known in the art and may be made to the side chains of the monomer derived from Msp. Such modifications include, for example, reductive alkylation of amino acids by reaction with an aldehyde followed by reduction with NaBH$_4$, amidination with methylacetimidate or acylation with acetic anhydride.

The monomer derived from Msp can be produced using standard methods known in the art. The monomer derived from Msp may be made synthetically or by recombinant means. For example, the pore may be synthesized by in vitro translation and transcription (IVTT). Suitable methods for producing pores are discussed in International Application Nos. PCT/GB09/001690 (published as WO 2010/004273), PCT/GB09/001679 (published as WO 2010/004265) or PCT/GB10/000133 (published as WO 2010/086603). Methods for inserting pores into membranes are discussed.

The transmembrane protein pore is also preferably derived from α-hemolysin (α-HL). The wild type α-HL pore is formed of seven identical monomers or subunits (i.e. it is heptameric). The sequence of one monomer or subunit of α-hemolysin-NN is shown in SEQ ID NO: 4. The transmembrane protein pore preferably comprises seven monomers each comprising the sequence shown in SEQ ID NO: 4 or a variant thereof. Amino acids 1, 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274, 287 to 290 and 294 of SEQ ID NO: 4 form loop regions. Residues 113 and 147 of SEQ ID NO: 4 form part of a constriction of the barrel or channel of α-HL.

In such embodiments, a pore comprising seven proteins or monomers each comprising the sequence shown in SEQ ID NO: 4 or a variant thereof are preferably used in the method of the invention. The seven proteins may be the same (homoheptamer) or different (heteroheptamer).

A variant of SEQ ID NO: 4 is a protein that has an amino acid sequence which varies from that of SEQ ID NO: 4 and which retains its pore forming ability. The ability of a variant to form a pore can be assayed using any method known in the art. For instance, the variant may be inserted into a lipid bilayer along with other appropriate subunits and its ability to oligomerise to form a pore may be determined. Methods are known in the art for inserting subunits into membranes, such as lipid bilayers. Suitable methods are discussed above.

The variant may include modifications that facilitate covalent attachment to or interaction with the helicase. The variant preferably comprises one or more reactive cysteine residues that facilitate attachment to the helicase. For instance, the variant may include a cysteine at one or more of positions 8, 9, 17, 18, 19, 44, 45, 50, 51, 237, 239 and 287 and/or on the amino or carboxy terminus of SEQ ID NO: 4. Preferred variants comprise a substitution of the residue at position 8, 9, 17, 237, 239 and 287 of SEQ ID NO: 4 with cysteine (A8C, T9C, N17C, K237C, S239C or E287C). The variant is preferably any one of the variants described in International Application No. PCT/GB09/001690 (published as WO 2010/004273), PCT/GB09/001679 (published as WO 2010/004265) or PCT/GB10/000133 (published as WO 2010/086603).

The variant may also include modifications that facilitate any interaction with nucleotides.

The variant may be a naturally occurring variant which is expressed naturally by an organism, for instance by a *Staphylococcus* bacterium. Alternatively, the variant may be expressed in vitro or recombinantly by a bacterium such as *Escherichia coli*. Variants also include non-naturally occurring variants produced by recombinant technology. Over the entire length of the amino acid sequence of SEQ ID NO: 4, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 4 over the entire sequence. There may be at least 80%, for example at least 85%, 90% or 95%, amino acid identity over a stretch of 200 or more, for example 230, 250, 270 or 280 or more, contiguous amino acids ("hard homology"). Homology can be determined as discussed above.

Amino acid substitutions may be made to the amino acid sequence of SEQ ID NO: 4 in addition to those discussed above, for example up to 1, 2, 3, 4, 5, 10, 20 or 30 substitutions. Conservative substitutions may be made as discussed above.

One or more amino acid residues of the amino acid sequence of SEQ ID NO: 4 may additionally be deleted from the polypeptides described above. Up to 1, 2, 3, 4, 5, 10, 20 or 30 residues may be deleted, or more.

Variants may be fragments of SEQ ID NO: 4. Such fragments retain pore-forming activity. Fragments may be at least 50, 100, 200 or 250 amino acids in length. A fragment preferably comprises the pore-forming domain of SEQ ID NO: 4. Fragments typically include residues 119, 121, 135, 113 and 139 of SEQ ID NO: 4.

One or more amino acids may be alternatively or additionally added to the polypeptides described above. An extension may be provided at the amino terminus or carboxy terminus of the amino acid sequence of SEQ ID NO: 4 or a variant or fragment thereof. The extension may be quite short, for example from 1 to 10 amino acids in length. Alternatively, the extension may be longer, for example up to 50 or 100 amino acids. A carrier protein may be fused to a pore or variant.

As discussed above, a variant of SEQ ID NO: 4 is a subunit that has an amino acid sequence which varies from that of SEQ ID NO: 4 and which retains its ability to form a pore. A variant typically contains the regions of SEQ ID NO: 4 that are responsible for pore formation. The pore forming ability of α-HL, which contains a β-barrel, is provided by β-strands in each subunit. A variant of SEQ ID NO: 4 typically comprises the regions in SEQ ID NO: 4 that form β-strands. The amino acids of SEQ ID NO: 4 that form 1-strands are discussed above. One or more modifications can be made to the regions of SEQ ID NO: 4 that form β-strands as long as the resulting variant retains its ability to form a pore. Specific modifications that can be made to the β-strand regions of SEQ ID NO: 4 are discussed above.

A variant of SEQ ID NO: 4 preferably includes one or more modifications, such as substitutions, additions or deletions, within its α-helices and/or loop regions. Amino acids that form α-helices and loops are discussed above.

The variant may be modified to assist its identification or purification as discussed above.

Pores derived from α-HL can be made as discussed above with reference to pores derived from Msp.

In some embodiments, the transmembrane protein pore is chemically modified. The pore can be chemically modified in any way and at any site. The transmembrane protein pore is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. The transmembrane protein pore may be chemically modified by the attachment of any molecule.

For instance, the pore may be chemically modified by attachment of a dye or a fluorophore.

Any number of the monomers in the pore may be chemically modified. One or more, such as 2, 3, 4, 5, 6, 7, 8, 9 or 10, of the monomers is preferably chemically modified as discussed above.

The molecule (with which the pore is chemically modified) may be attached directly to the pore or attached via a linker as disclosed in International Application Nos.

PCT/GB09/001690 (published as WO 2010/004273), PCT/GB09/001679 (published as WO 2010/004265) or PCT/GB10/000133 (published as WO 2010/086603).

Ratchets that may be used are as follows.

The translocation of the polymer through the nanopore may be performed in a ratcheted manner. In this case successive k-mers of the polymer are registered with the nanopore. In this manner each measurement is dependent on a particular k-mer. If the registration is held for sufficient time, then a group of plural measurements will be dependent on a particular k-mer. Depending on the nature of the translocation, the period of registration can be unpredictable and may vary in length. Depending on the period of registration, relative to the measurement sampling rate, it might be that there are not plural measurements, or even a signal measurement, that are dependent on every k-mer in the sequence.

The translocation of the polymer may be controlled by a molecular ratchet that controls the movement of the polymer through the pore. The molecular ratchet may be a polymer binding protein. For polynucleotides, the polynucleotide binding protein is preferably a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the target polynucleotide and controlling its movement through the pore. For instance, the enzyme may be modified to remove its enzymatic activity or may be used under conditions which prevent it from acting as an enzyme. Such conditions are discussed in more detail below.

The polynucleotide handling enzyme may be derived from a nucleolytic enzyme. The polynucleotide handling enzyme used in the construct of the enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in International Application No. PCT/GB10/000133 (published as WO 2010/086603).

Preferred enzymes are polymerases, exonucleases, helicases and topoisomerases, such as gyrases. Suitable enzymes include, but are not limited to, exonuclease I from *E. coli* (SEQ ID NO: 8), exonuclease III enzyme from *E. coli* (SEQ ID NO: 10), RecJ from *T. thermophilus* (SEQ ID NO: 12) and bacteriophage lambda exonuclease (SEQ ID NO: 14) and variants thereof. Three subunits comprising the sequence shown in SEQ ID NO: 14 or a variant thereof interact to form a trimer exonuclease. The enzyme is preferably derived from a Phi29 DNA polymerase. An enzyme derived from Phi29 polymerase comprises the sequence shown in SEQ ID NO: 6 or a variant thereof.

A variant of SEQ ID NOs: 6, 8, 10, 12 or 14 is an enzyme that has an amino acid sequence which varies from that of SEQ ID NO: 6, 8, 10, 12 or 14 and which retains polynucleotide binding ability. The variant may include modifications that facilitate binding of the polynucleotide and/or facilitate its activity at high salt concentrations and/or room temperature.

Over the entire length of the amino acid sequence of SEQ ID NO: 6, 8, 10, 12 or 14, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 6, 8, 10, 12 or 14 over the entire sequence. There may be at least 80%, for example at least 85%, 90% or 95%, amino acid identity over a stretch of 200 or more, for example 230, 250, 270 or 280 or more, contiguous amino acids ("hard homology").

Homology is determined as described above. The variant may differ from the wild-type sequence in any of the ways discussed above with reference to SEQ ID NO: 2. The enzyme may be covalently attached to the pore as discussed above.

The two strategies for single strand DNA sequencing are the translocation of the DNA through the nanopore, both cis to trans and trans to cis, either with or against an applied potential. The most advantageous mechanism for strand sequencing is the controlled translocation of single strand DNA through the nanopore under an applied potential.

Exonucleases that act progressively or processively on double stranded DNA can be used on the cis side of the pore to feed the remaining single strand through under an applied potential or the trans side under a reverse potential. Likewise, a helicase that unwinds the double stranded DNA can also be used in a similar manner. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential. Alternatively, the single strand DNA dependent polymerases can act as molecular brake slowing down the movement of a polynucleotide through the pore.

In a preferred embodiment, strand sequencing is carried out using a pore derived from Msp and a Phi29 DNA polymerase. The method comprises (a) adding the polynucleotide to the solution; (b) allowing the target polynucleotide to interact with a detector in the membrane, which detector comprises a pore derived from Msp and a Phi29 DNA polymerase, such that the polymerase controls the movement of the target polynucleotide through the pore and a proportion of the nucleotides in the target polynucleotide interacts with the pore; and (c) measuring the current passing through the pore during each interaction and thereby determining the sequence of the target polynucleotide, wherein steps (b) and (c) are carried out with a voltage applied across the pore. When the target polynucleotide is contacted with a Phi29 DNA polymerase and a pore derived from Msp, the target polynucleotide firstly forms a complex with the Phi29 DNA polymerase. When the voltage is applied across the pore, the target polynucleotide/Phi29 DNA polymerase complex forms a complex with the pore and controls the movement of the target polynucleotide through the pore.

Wild-type Phi29 DNA polymerase has polymerase and exonuclease activity. It may also unzip double stranded polynucleotides under the correct conditions. Hence, the enzyme may work in three modes. This is discussed in more detail below.

The Phi29 DNA polymerase may comprise the sequence shown in SEQ ID NO: 6 or a variant thereof. A variant of SEQ ID NO: 6 is an enzyme that has an amino acid sequence which varies from that of SEQ ID NO: 6 and which retains polynucleotide binding activity. The variant must work in at least one of the three modes discussed below. Preferably, the variant works in all three modes. The variant may include modifications that facilitate handling of the polynucleotide and/or facilitate its activity at high salt concentrations and/or room temperature.

Over the entire length of the amino acid sequence of SEQ ID NO: 6, a variant will preferably be at least 40% homologous to that sequence based on amino acid identity. More preferably, the variant polypeptide may be at least 50%, at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 6 over the entire sequence. There may be at least 80%, for example at least 85%, 90% or 95%, amino acid identity over a stretch of 200 or more, for example 230, 250, 270 or 280 or more, contiguous amino acids ("hard homology").

Homology is determined as described above. The variant may differ from the wild-type sequence in any of the ways discussed above with reference to SEQ ID NO: 2.

Any of the systems, apparatus or conditions discussed above may be used in accordance with this preferred embodiment. The salt concentration is typically from 0.15M to 0.6M. The salt is preferably KCl.

The method may be carried out in one of three preferred ways based on the three modes of the Phi29 DNA polymerase. Each way includes a method of proof-reading the sequence. First, the method is preferably carried out using the Phi29 DNA polymerase as a polymerase. In this embodiment, steps (b) and (c) are carried out in the presence of free nucleotides and an enzyme cofactor such that the polymerase moves the target polynucleotide through the pore against the field resulting from the applied voltage. The target polynucleotide moves in the 5' to 3' direction. The free nucleotides may be one or more of any of the individual nucleotides discussed above. The enzyme cofactor is a factor that allows the Phi29 DNA polymerase to function either as a polymerase or an exonuclease. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$. The method preferably further comprises (d) removing the free nucleotides such that the polymerase moves the target polynucleotide through the pore with the field resulting from the applied voltage (i.e. in the 3' and 5' direction) and a proportion of the nucleotides in the target polynucleotide interacts with the pore and (e) measuring the current passing through the pore during each interaction and thereby proof reading the sequence of the target polynucleotide obtained in step (c), wherein steps (d) and (e) are also carried out with a voltage applied across the pore.

Second, the method is preferably carried out using the Phi29 DNA polymerase as an exonuclease. In this embodiment, wherein steps (b) and (c) are carried out in the absence of free nucleotides and the presence of an enzyme cofactor such that the polymerase moves the target polynucleotide through the pore with the field resulting from the applied voltage. The target polynucleotide moves in the 3' to 5' direction. The method preferably further comprises (d) adding free nucleotides such that the polymerase moves the target polynucleotide through the pore against the field resulting from the applied voltage (i.e. in the 5' to 3' direction) and a proportion of the nucleotides in the target polynucleotide interacts with the pore and (e) measuring the current passing through the pore during each interaction and thereby proof reading the sequence of the target polynucleotide obtained in step (c), wherein steps (d) and (e) are also carried out with a voltage applied across the pore.

Third, the method is preferably carried out using the Phi29 DNA polymerase in unzipping mode. In this embodiment, steps (b) and (c) are carried out in the absence of free nucleotides and the absence of an enzyme cofactor such that the polymerase controls the movement of the target polynucleotide through the pore with the field resulting from the applied voltage (as it is unzipped). In this embodiment, the polymerase acts like a brake preventing the target polynucleotide from moving through the pore too quickly under the influence of the applied voltage. The method preferably further comprises (d) lowering the voltage applied across the pore such that the target polynucleotide moves through the pore in the opposite direction to that in steps (b) and (c) (i.e. as it re-anneals) and a proportion of the nucleotides in the target polynucleotide interacts with the pore and (e) measuring the current passing through the pore during each interaction and thereby proof reading the sequence of the target polynucleotide obtained in step (c), wherein steps (d) and (e) are also carried out with a voltage applied across the pore.

In another preferred embodiment, a helicase is used as a ratchet for the polynucleotide (for example as disclosed in U.S. 61/549,998 (N115020), U.S. 61/581,332 (N115505), U.S. 61/581,340 that are incorporated herein by reference). It has been shown that helicases have a surprisingly high salt tolerance. Helicases can move the target polynucleotide in two directions, namely with or against the field resulting from the applied voltage. Hence, the method may be carried out in one of two preferred modes. Different signals are obtained depending on the direction the target polynucleotide moves through the pore, i.e. in the direction of or against the field. Helicases typically move the target polynucleotide through the pore one nucleotide at a time. Helicases can therefore function like a single-base ratchet.

This is of course advantageous when sequencing a target polynucleotide because substantially all, if not all, of the nucleotides in the target polynucleotide may be identified using the pore. Helicases are capable of controlling the movement of single stranded polynucleotides and double stranded polynucleotides. Helicases appear very resistant to the field resulting from applied voltages. Very little movement of the polynucleotide under an "unzipping" condition was observed. This is important because it means that there are no complications from unwanted "backwards" movements when moving polynucleotides against the field resulting from an applied voltage.

The method comprises: (a) contacting the target polynucleotide with a transmembrane pore and a helicase such that the helicase controls the movement of the target polynucleotide through the pore and nucleotides in the target polynucleotide interact with the pore; and (b) measuring the current passing through the pore during one or more interactions to measure one or more characteristics of the target polynucleotide and thereby characterising the target polynucleotide.

As discussed above, helicases may work in two modes with respect to the nanopore. For a helicase that translocates in the 3' to 5' direction, the two modes are as follows. First, the method is preferably carried out using the helicase such that it moves the target sequence through the pore with the field resulting from the applied voltage. In this mode the 3' end of the DNA is first captured in the nanopore, and the enzyme moves the DNA into the nanopore such that the target sequence is passed through the nanopore with the field until it finally translocates through to the trans side of the bilayer. Alternatively, the method is preferably carried out such that the enzyme moves the target sequence through the pore against the field resulting from the applied voltage. In this mode the 5' end of the DNA is first captured in the nanopore, and the enzyme moves the DNA through the nanopore such that the target sequence is pulled out of the nanopore against the applied field until finally ejected back to the cis side of the bilayer.

For a helicase that translocates in the 5' to 3' direction, the two modes are as follows. First, the method is preferably carried out using the helicase such that it moves the target sequence through the pore with the field resulting from the applied voltage. For In this mode the 5' end of the DNA is first captured in the nanopore, and the enzyme moves the DNA into the nanopore such that the target sequence is passed through the nanopore with the field until it finally translocates through to the trans side of the bilayer. Alternatively, the method is preferably carried out such that the enzyme moves the target sequence through the pore against the field resulting from the applied voltage. In this mode the 3' end of the DNA is first captured in the nanopore, and the enzyme moves the DNA through the nanopore such that the target sequence is pulled out of the nanopore against the applied field until finally ejected back to the cis side of the bilayer.

Measurement systems that may be used are as follows.

The methods may be carried out using any apparatus that is suitable for investigating a membrane/pore system in which a pore is inserted into a membrane. The method may be carried out using any apparatus that is suitable for transmembrane pore sensing. For example, the apparatus comprises a chamber comprising an aqueous solution and a barrier that separates the chamber into two sections. The barrier has an aperture in which the membrane containing the pore is formed.

The methods may be carried out using the apparatus described in International Application No. PCT/GB08/000562 (WO 2008/102120).

The methods may involve measuring the current passing through the pore during one or more interactions with the nucleotide(s). Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods of the invention may involve the measuring of a current passing through the pore during one or more interactions with the nucleotide. Suitable conditions for measuring ionic currents through transmembrane protein pores are known in the art and disclosed in the Example. The method is typically carried out with a voltage applied across the membrane and pore. The voltage used is typically from +2 V to −2 V, typically −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl) or caesium chloride (CsCl) is typically used. NaCl is preferred. The salt concentration may be at saturation. The salt concentration may be 3M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a polymer to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is HEPES. Another suitable buffer is Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

The method is typically carried out in the presence of free nucleotides or free nucleotide analogues and an enzyme cofactor that facilitate the action of the molecular ratchet or enzyme. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the enzyme to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

The target polymer may be contacted with the molecular ratchet and the pore in any order. In is preferred that, when the target polymer is contacted with the molecular ratchet and the pore, the target polymer firstly forms a complex with the molecular ratchet. When the voltage is applied across the pore, the target polymer/molecular ratchet complex then forms a complex with the pore and controls the movement of the polymer through the pore.

The nature of the measurements may be as follows.

A property that depends on the polymer units translocating through the pore may be measured. The property may be associated with an interaction between the polymer and the pore. Interaction of the polymer may occur at a constricted region of the pore. The measurement system measures the property, producing a measurement that is dependent on the polymer units of the polymer.

A variety of different types of measurements may be made. This includes without limitation: electrical measurements and optical measurements. Possible electrical measurements include: ion current flow measurements, impedance measurements, tunnelling measurements (Ivanov A P et al., Nano Lett. 2011 Jan. 12; 11(1):279-85), and FET measurements (International Application WO 2005/124888). Optical measurements may be combined with electrical measurements (Soni G V et al., Rev Sci Instrum. 2010 January; 81(1):014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO-2000/28312. Alternatively, electrical measurements may be made using a multi-channel system, for example as described in International Application WO-2009/077734 and International Application WO-2011/067559.

It is possible to use measurements of more than one property. For example, one possibility is to use measurements of ion current flow together with measurements of at least one additional property besides ion current flow, for example comprising FET measurements, optical measurements, or both.

The measurement system may comprise a plurality of pores. The apparatus preferably further comprise a plurality of a polymer ratchets. The apparatus preferably further comprises instructions for carrying out the method of the invention. The apparatus may be any conventional apparatus for polymer analysis, such as an array or a chip. Any of the embodiments discussed above with reference to the methods of the invention are equally applicable to the apparatus of the invention.

The apparatus is preferably set up to carry out the method of the invention.

The apparatus may comprises: a sensor device that is capable of supporting the membrane and plurality of pores and being operable to perform polymer characterising using the pores; at least one reservoir for holding material for performing the characterising; a fluidics system configured to controllably supply material from the at least one reservoir to the sensor device; and a plurality of containers for receiving respective samples, the fluidics system being configured to supply the samples selectively from the containers to the sensor device. The apparatus may be any of those described in International Application No. PCT/GB08/004127 (published as WO 2009/077734), PCT/GB10/000789 (published as WO 2010/122293), International Application No. PCT/GB10/002206 (not yet published) or International Application No. PCT/US99/25679 (published as WO 00/28312), all of which are incorporated herein by reference.

The apparatus may be a diagnostic device. The diagnostic device may be a benchtop or handheld device. The device may be operated in conjunction with a cartridge, the cartridge comprising the nanopore assay components and for receiving the fluid sample. The cartridge may be housed in the device or otherwise operably connectable with the device. The cartridge may be subsequently removed or disconnected from the device in order to clean the cartridge for re-use, or for disposal. Thereafter an unused or cleaned cartridge may be used with the device. The cartridge may be an integral part of the device wherein the device is disposable after use. The cartridge will typically have a sample application region for receiving a fluid sample. The sample application region may be a microfluidic channel or a porous sample pad for example to directly receive a urine sample. The size of sample would typically range from 0.25 uL to 10 mL. The sample application region may serve to directly receive a sample from a patient, for example a sample of blood obtained with a fingerstick. The cartridge may comprise a red blood cell filter for filtering red blood cells. The cartridge may comprise dried reagents such as a salt, an anticoagulant, or a buffer. The device will typically comprise data input and output ports and a memory for sending or receiving and storing data, such as information in relation to feature vectors, patient ID, and measurement results. The device may have wireless connectivity for communicating with a remote server or medical professional. Typically the device and cartridge are not restricted to measurement of a particular analyte and may capable of measuring any particular analyte and feature vectors relating to a particular analyte of interest may be uploaded and stored in the memory.

Although ideally the measurements would be dependent on a single polymer unit (which may thought of as a k-mer comprising k polymer units where k=1), with many typical measurement systems, the measurement is dependent on a k-mer comprising k polymer units where k is a plural integer. That is, each measurement is dependent on the sequence of each of the polymer units in a k-mer. Typically the measurements are of a property that is associated with an interaction between the polymer and the measurement system.

In some embodiments of the present invention it is preferred to use measurements that are dependent on small groups of polymer units, for example doublets or triplets of polymer units (i.e. in which k=2 or k=3). In other embodiments, it is preferred to use measurements that are dependent on larger groups of polymer units, i.e. with a "broad" resolution. Such broad resolution may be particularly useful for examining homopolymer regions.

Where measurements are dependent on a k-mer, it is desirable that the measurements are resolvable (i.e. separated) for as many as possible of the possible k-mers. Typically this can be achieved if the measurements produced by different k-mers are well spread over the measurement range and/or have a narrow distribution. This may be achieved to varying extents by different measurement systems. However, it is a particular advantage of the present invention, that it is not essential for the measurements produced by different k-mers to be resolvable.

FIG. 1 schematically illustrates an example of a measurement system 8 comprising a nanopore that is a biological pore 1 inserted in a biological membrane 2 such as a lipid bilayer. A polymer 3 comprising a series of polymer units 4 is translocated through the biological pore 1 as shown by the arrows. The polymer 3 may be a polynucleotide in which the polymer units 4 are nucleotides. The polymer 3 interacts with an active part 5 of the biological pore 1 causing an electrical property such as the trans-membrane current to vary in dependence on a k-mer inside the biological pore 1. In this example, the active part 5 is illustrated as interacting with a k-mer of three polymer units 4, but this is not limitative.

Electrodes 6 arranged on each side of the biological membrane 2 are connected to a measurement circuit 7 that measures the electrical property. Thus the measurements are dependent on the k-mer inside the biological pore 1.

Figure 2:
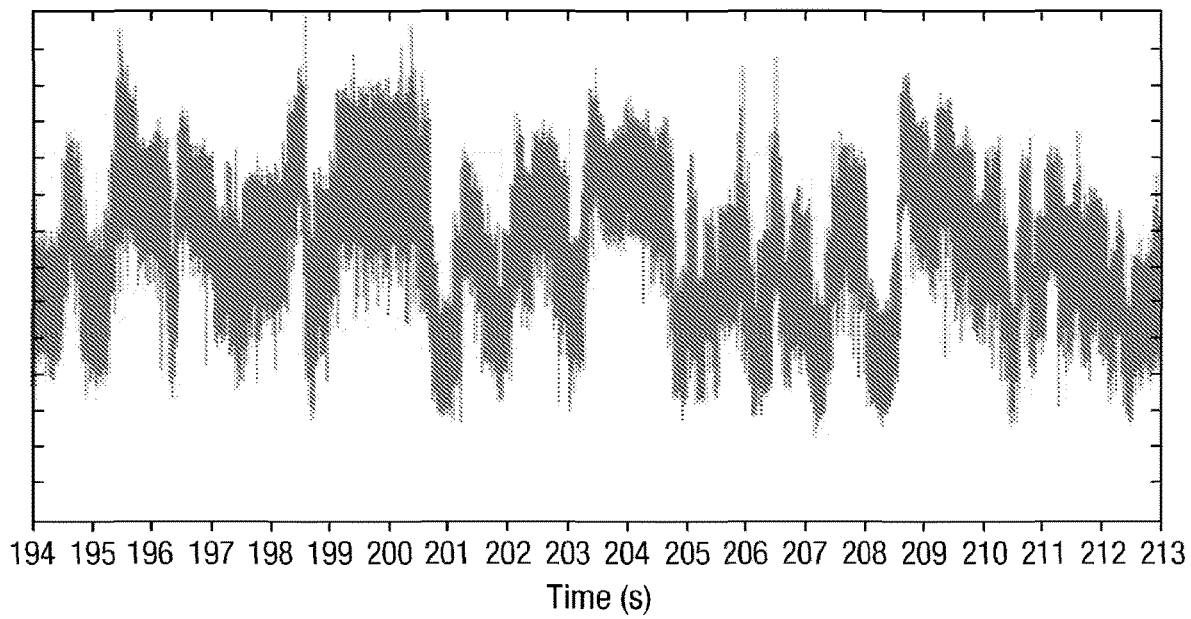
FIG. 2 is a plot of a signal of an event measured over time by a measurement system.

A typical type of signal output by a measurement system and which is an input signal to be analysed in accordance with the present invention is a "noisy step wave", although without limitation to this signal type. An example of an input signal having this form is shown in FIG. 2 for the case of an ion current measurement obtained using a measurement system comprising a nanopore.

This type of input signal comprises an input series of measurements in which successive groups of plural measurements are dependent on the same k-mer. The plural measurements in each group are constant, subject to some variance discussed below, and therefore form a "level" in the signal, corresponding to a state of the measurement system. The signal moves between a set of levels, which may be a large set. Given the sampling rate of the instrumentation and the noise on the signal, the transitions between levels can be considered instantaneous, thus the signal can be approximated by an idealised step trace.

The measurements corresponding to each state are constant over the time scale of the event, but for most measurement systems will be subject to variance over a short time scale. Variance can result from measurement noise, for example arising from the electrical circuits and signal processing, notably from the amplifier in the particular case of electrophysiology. Such measurement noise is inevitable due the small magnitude of the properties being measured. Variance can also result from inherent variation or spread in the underlying physical or biological system of the measurement system. Most measurement systems will experience such inherent variation to greater or lesser extents, even in the idealised case that measurement noise is avoided. For any given measurement system, both sources of variation may contribute or one of these noise sources may be dominant.

In addition, typically there is no a priori knowledge of number of measurements in the group, which varies unpredictably.

These two factors of variance and lack of knowledge of the number of measurements can make it hard to distinguish some of the groups, for example where the group is short and/or the levels of the measurements of two successive groups are close to one another.

The signal takes this form as a result of the physical or biological processes occurring in the measurement system. Thus, each group of measurements may be referred to as a "state".

For example, in some measurement systems comprising a nanopore, the event consisting of translocation of the polymer through the nanopore may occur in a ratcheted manner. During each step of the ratcheted movement, the ion current flowing through the nanopore at a given voltage across the nanopore is constant, subject to the variance discussed above. Thus, each group of measurements is associated with a step of the ratcheted movement. Each step corresponds to a state in which the polymer is in a respective position relative to the nanopore. Although there may be some variation in the precise position during the period of a state, there are large scale movements of the polymer between states. Depending on the nature of the measurement system, the states may occur as a result of a binding event in the nanopore.

There may be other information available either as part of the measurement or from additional sources that provides registration information. This other information may enable states to be identified.

Alternatively, the signal may take an arbitrary form. In these cases, the measurements corresponding to k-mers may also be described in terms of a set of emissions and transitions. For example, a measurement that is dependent on a particular k-mer may comprise of a series of measurements occurring in a fashion amenable to description by these methods.

The extent to which a given measurement system provides measurements that are dependent on k-mers and the size of the k-mers may be examined experimentally. For example, known polymers may be synthesized and held at predetermined locations relative to the measurement system to investigate from the resultant measurements how the measurements depend on the identity of k-mers that interact with the measurement system.

One possible approach is to use a set of polymers having identical sequences except for a k-mer at a predetermined position that varies for each polymer of the set. The size and identity of the k-mers can be varied to investigate the effect on the measurements.

Figure 3:
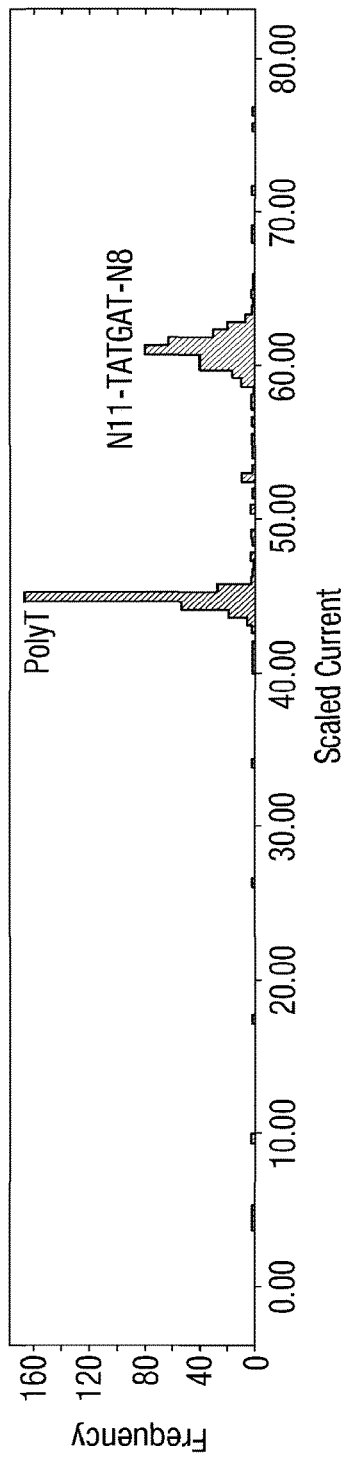
FIG. 3 is a graph of the frequency distributions of measurements of two different polynucleotides in a measurement system comprising a nanopore.

Another possible approach is to use a set of polymers in which the polymer units outside a k-mer under investigation at a predetermined position vary for each polymer of the set. As an example of such an approach, FIG. 3 is a frequency distribution of current measurements of two polynucleotides in a measurement system comprising a nanopore. In one of the polynucleotides (labelled polyT), every base in the region of the nanopore is a T (labelled polyT), and in the other of the polynucleotides (labelled N11-TATGAT-N8), 11 bases to the left and 8 to the right of a specific fixed 6-mer (having the sequence TATGAT) are allowed to vary. The example of FIG. 3 shows excellent separation of the two strands in terms of the current measurement. The range of values seen by the N11-TATGAT-N8 strand is also only slightly broader than that seen by the polyT. In this way and measuring polymers with other sequences also, it can be ascertained that, for the particular measurement system in question, measurements are dependent on 6-mers to a good approximation.

This approach, or similar, can be generalised for any measurement system enabling the location and a minimal k-mer description to be determined.

Similar methodology may be used to identify location and width of well-approximating k-mers in a general measurement system. In the example of FIG. 3, this is achieved by changing the position of the 6-mer relative to the pore (e.g. by varying the number of Ns before and after) to detect location of the best approximating k-mer and increasing and decreasing the number of fixed bases from 6. The value of k can be minimal subject to the spread of values being sufficiently narrow. The location of the k-mer can be chosen to minimise peak width.

For typical measurement systems, it is usually the case that measurements that are dependent on different k-mers are not all uniquely resolvable. For example, in the measurement system to which FIG. 3 relates, it is observed that the range of the measurements produced by DNA strands with a fixed 6-mer is of the order of 2 pA and the approximate measurement range of this system is between 30 pA and 70 pA. For a 6-mer, there are 4096 possible k-mers. Given that each of these has a similar variation of 2 pA, it is clear that in a 40 pA measurement range these signals will not be uniquely resolvable. Even where measurements of some k-mers are resolvable, it is typically observed that measurements of many other k-mers are not.

For many actual measurement systems, it is not possible to identify a function that transforms k measurements, that each depend in part on the same polymer unit, to obtain a single value that is resolved at the level of a polymer unit, or more generally the k-mer measurement is not describable by a set of parameters smaller than the number of k-mers.

Figure 4:
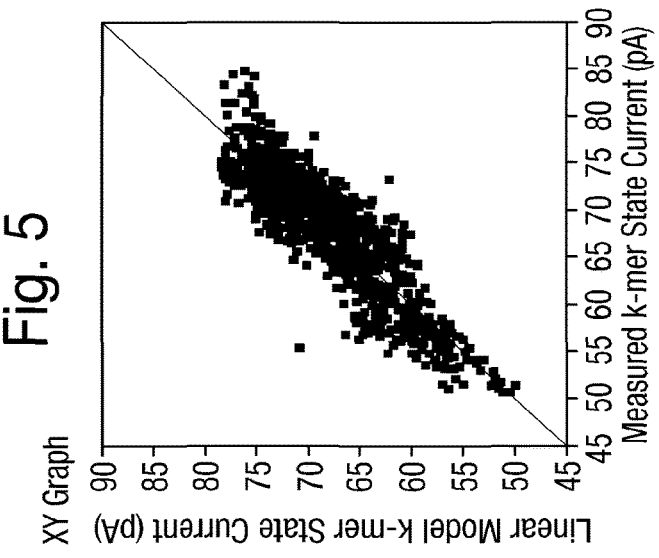
FIGS. 4 and 5 are plots of 64 3-mer coefficients and 1024 5-mer coefficients, respectively, against predicted values from a first order linear model applied to sets of experimentally derived current measurements.
Figure 5:
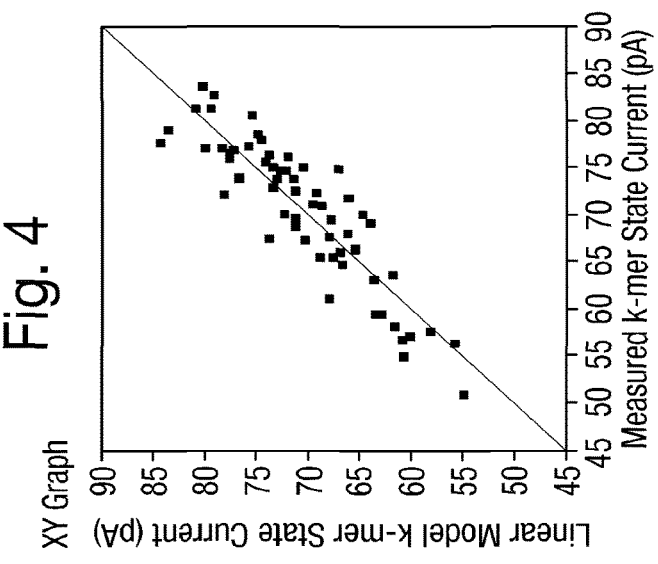

By way of example, it will now be demonstrated for a particular measurement system comprising a nanopore experimentally derived ion current measurements of polynucleotides are not accurately describable by a simple first order linear model. This is demonstrated for the two training sets described in more detail below. The simple first order linear model used for this demonstration is:

$$\text{Current} = \text{Sum}[fn(Bn)] + E$$

where fn are coefficients for each base Bn occurring at each position n in the measurement system and E represents the random error due to experimental variability. The data are fit to this model by a least squares method, although any one of many methods known in the art could alternatively be used. FIGS. 4 and 5 are plots of the best model fit against the current measurements. If the data was well described by this model, then the points should closely follow the diagonal line within a typical experimental error (for example 2 pA). This is not the case showing that the data is not well described by this linear model for either set of coefficients.

There will now be described a specific method of analysing a time-ordered sequence of measurements.

Figure 6:
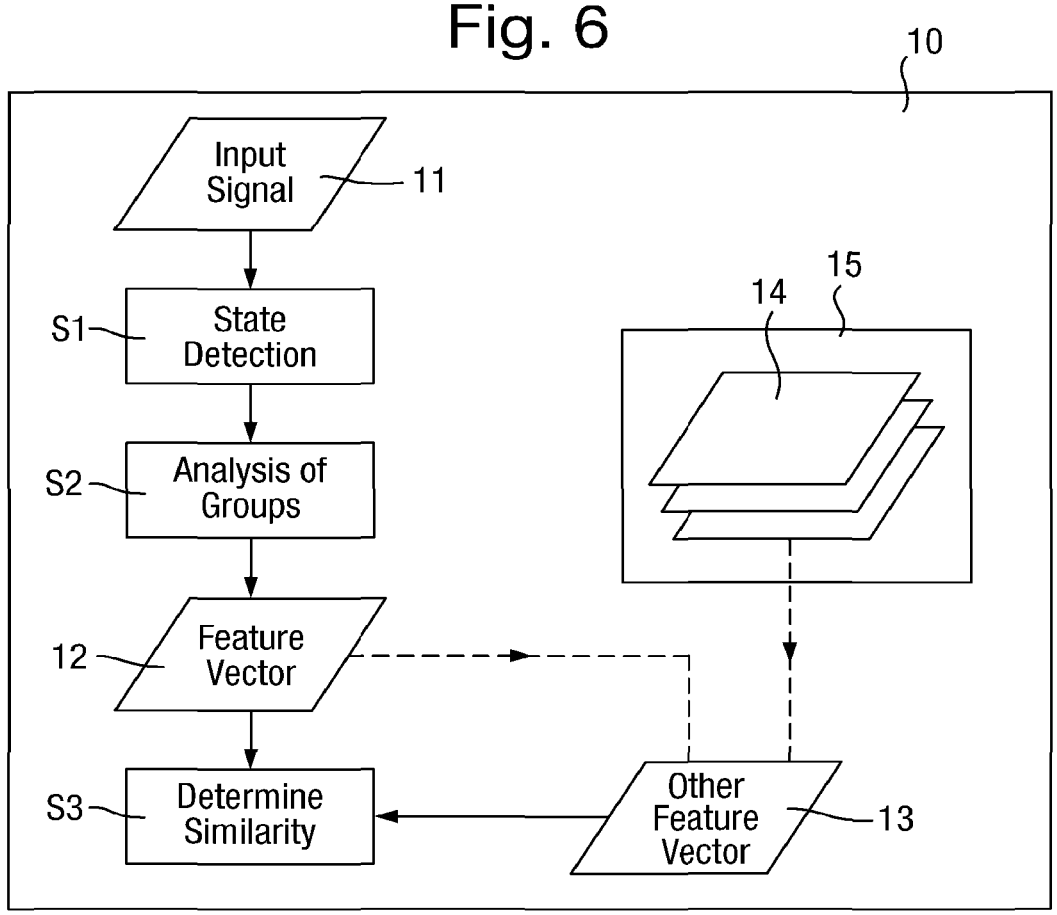
FIG. 6 is a flowchart of a method of analyzing an input signal comprising measurements of a polymer.

The method is illustrated in FIG. 6 and may be computer-implemented in an analysis device 10 illustrated schematically in FIG. 6. The analysis device 10 may be implemented by a computer program executed in a computer apparatus or may be implemented by a dedicated hardware device, or any combination thereof. In either case, the data used by the method is stored in a memory in the analysis device 10. The computer apparatus, where used, may be any type of computer system but is typically of conventional construction. The computer program may be written in any suitable programming language. The computer program may be stored on a computer-readable storage medium (i.e. a non-transitory medium), which may be of any type, for example: a recording medium which is insertable into a drive of the computing system and which may store information magnetically, optically or opto-magnetically; a fixed recording medium of the computer system such as a hard drive; or a computer memory.

There is first described the method that is performed on an input signal 11 that has sufficient time resolution that it comprises a series of measurements (or more generally any number of series, as described further below) of the type described above in which the measurements are time-ordered and comprise successive groups of plural measurements that are dependent on the same k-mer without a priori knowledge of number of measurements in any group.

An example of such an input signal 11 is shown in FIG. 2 as previously described.

In a state detection step S1, the input signal 11 is processed to identify successive groups of measurements.

Figure 7:
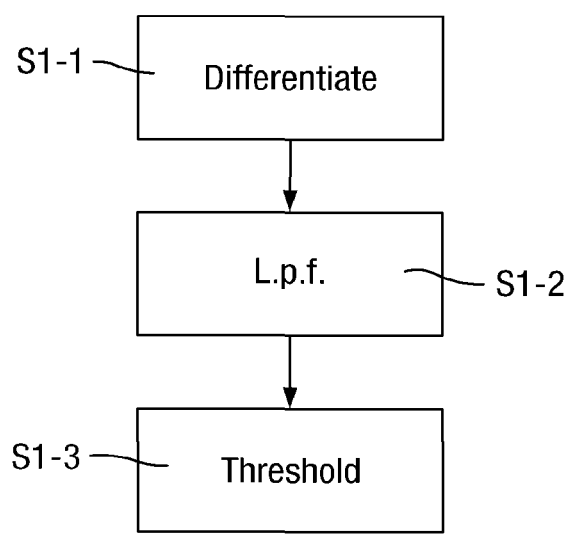
FIG. 7 is a flowchart of a state detection step of FIG. 6.

The state detection step S1 may be performed using the method shown in FIG. 7 that looks for short-term increases in the derivative of the input signal 11 as follows.

In step S1-1, the input signal 11 is differentiated to derive its derivative.

In step S1-2, the derivative from step S1-1 is subjected to low-pass filtering to suppress high-frequency noise (which the differentiation tends to amplify).

In step S1-3, the filtered derivative from step S1-2 is thresholded to detect transition points between the groups of measurements, and thereby identify the groups of data.

In step S2, the measurements in each identified group are to derive values of one or more features that represent characteristics in respect of each group. In the simplest approach, a single value is derived, for example the mean, but plural values of features that represent the same or different characteristics may be used to increase the information content. Examples of features that may be used include: an average (a mean or a median or other average) of the group of measurements; the period of the group of measurements; a variance of the group of measurements; the distribution of the group of measurements, asymmetry information; the confidence of the measurements; or any combination thereof.

The values of the features output from step S2 form a feature vector 12 in which the values are time-ordered in the same order as the groups from which they are derived.

Step S2 has the result of providing a representation of the input signal 11 in which the amount of information is reduced, but in which the significant characteristics of the signal are maintained.

In general, other methods may alternatively be used in place of steps S1 an/or S2 to derive the feature vector 12 of values of one or more features that represent characteristics of the input signal 11, time-ordered in the same order as the input signal 11.

In particular, it is not necessary to specifically identify the groups, and as such the methods may be applied to input signals where the time resolution is lower to the extent that some k-mers may provide only a single measurement or no measurement at all.

A possible simplification of the state detection step is to use a sliding window analysis whereby one compares the means of two adjacent windows of data. A threshold can then be either put directly on the difference in mean, or can be set based on the variance of the data points in the two windows (for example, by calculating Student's t-statistic).

A particular advantage of these methods is that they can be applied without imposing many assumptions on the data.

Figure 8:
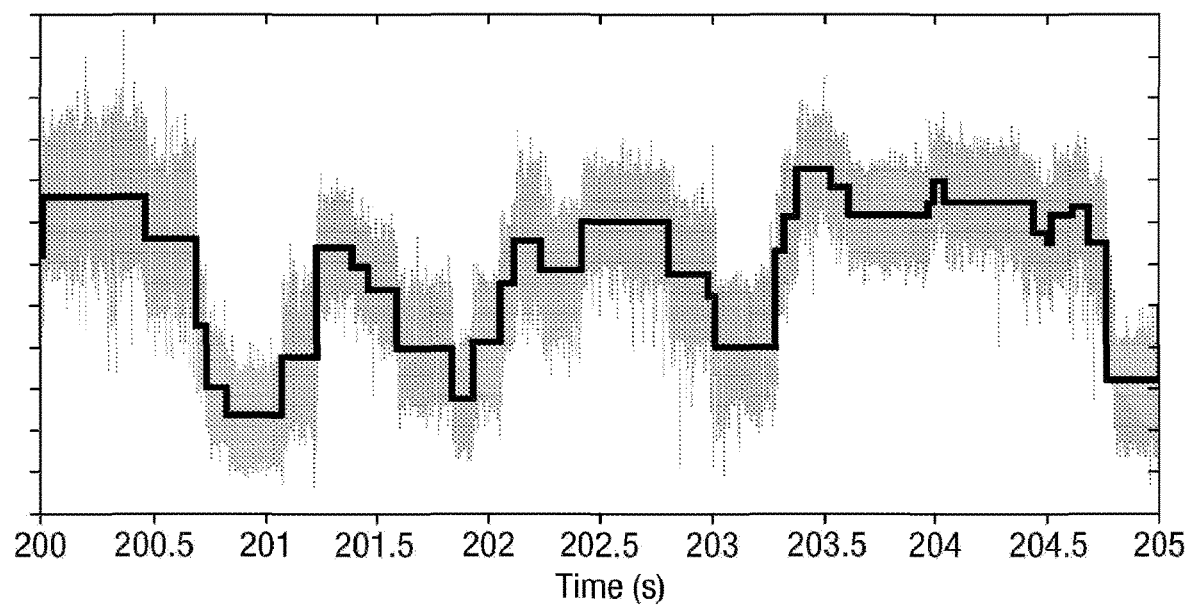
FIGS. 8 and 9 are plots, respectively, of an input signal subject to the state detection step and of the resultant series of measurements.
Figure 9:
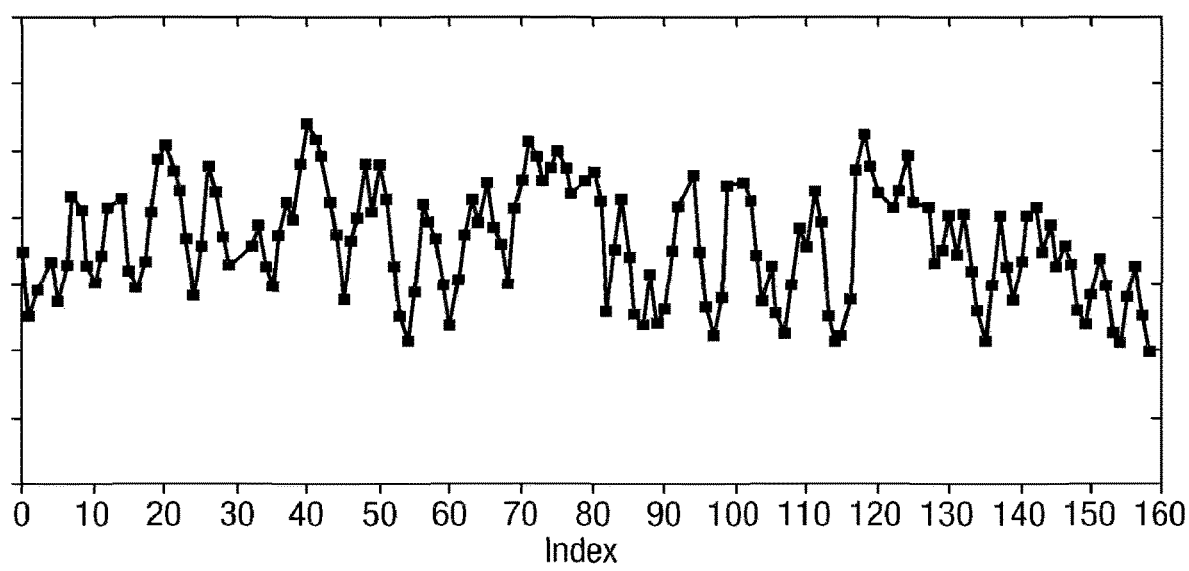

By way of example, FIG. 8 illustrates an experimentally determined input signal 11 reduced by a moving window t-test. In particular, FIG. 8 shows the input signal 11 as the light line. Levels following state detection are shown overlayed as the dark line. FIG. 9 shows the values derived for the entire trace, calculating the level of each state from the mean value between transitions.

In step S3, the feature vector 12 derived in step S2 is compared with at least one other feature vector 13 to determine the similarity there between. As shown by the dotted lines, that other feature vector 13 may be one or more feature vectors 14 stored in memory 15 of the analysis device 10, or alternatively may be one or more feature vectors 12 derived using steps S1 and S2 from input signals 11 that are series of measurements of other polymers.

Step S3 may be implemented in a variety of manners to derive useful information about the polymer under investigation. Some non-limitative examples of step S3 are as follows.

Figure 10:
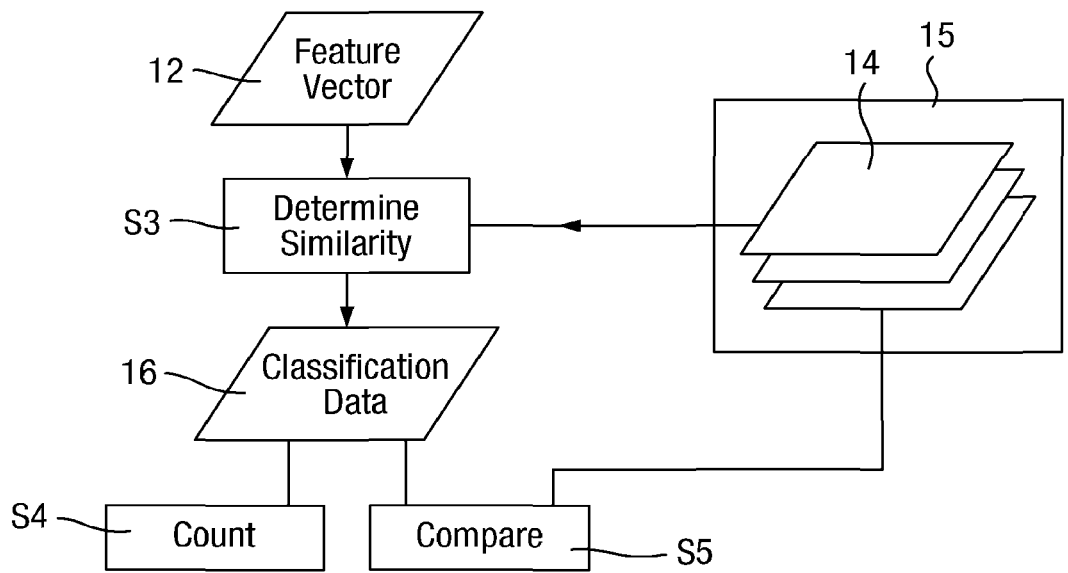
FIGS. 10 and 11 are flowcharts of examples of the similarity determination step of FIG. 6.

In a first example of step S3 shown in FIG. 10, the feature vector 12 derived in step S2 is compared with the other feature vector that is one or more of plural feature vectors 14 stored in a memory 15 of the analysis device 10 in respect of at least one class, as a library. In this case, in step S3 produces classification data 16 that classifies the polymer from which the derived feature vector 12 is derived as belonging to one of the classes on the basis of the determined similarity.

Depending on the nature of the polymers represented by the feature vectors 14 in the memory 15, similarity may be determined between the entirety or part of the derived feature vector 12 and the entirety of the feature vector 14 stored in the memory 15, or between the entirety or part of the derived feature vector 12 and a part of the feature vector 14 stored in the memory 15.

In this case, optionally the method may be repeated on input signals 11 that are series of measurements of other polymers, for example from the same sample. In that case either or both of the following steps S4 and S5 may be performed.

In step S4 the numbers of polymers in each class may be counted. That provides information on the profile of the population of polymers under investigation.

In step S5, the derived feature vector 12 is compared again with the feature vector feature vector 14 stored in a memory 15 of the class within which the polymer of the derived feature vector 12 is classified as belonging. In this comparison, similarity is again determined, but this time to identify localized regions where the derived feature vector 12 is dissimilar to that feature vector 14 in respect of the class. Such identification of localized regions where the derived feature vector is dissimilar to what is expected provides an analysis technique that is very powerful in many applications where change in relatively small regions of long sequences of polymers is significant. One example of such a technique is to identify mutations in a polymer that is a polynucleotide.

In step S3, the feature vector 13 used for the comparison may be selected from the feature vectors 14 stored in the memory 15 depending upon the polymer to be measured.

The feature vectors 14 stored in the memory 15 may comprise two or more feature vectors having overlapping regions. In that case, the similarity may be determined in step S3 with the non-overlapping regions of the feature vectors 14 are used in the determination of similarity with the derived feature vector 12.

Figure 11:
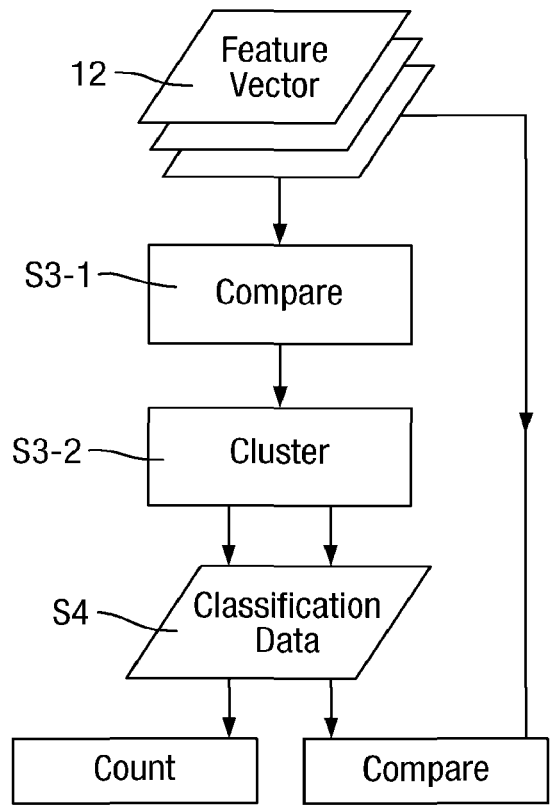

In a second example shown in FIG. 11, step S3 is performed in respect of plural feature vectors 12 derived by performing steps S1 and S2 on plural polymers, for example polymers from the same sample or polymers that are fragments of a common polymer.

In this second example, step S3 comprises the following steps.

In step S3-1, the plural derived feature vectors 12 are compared with each other and the similarity therebetween is determined.

In step S3-2, the plural derived feature vectors 12 are clustered on the basis of their similarity. In particular, clusters of similar feature vectors 12 are identified as a class. Step S3-2 produces classification data 16 that classifies the polymers from which each derived feature vector 12 is derived as belonging to one of the classes.

The classification data 16 may be processed by steps S4 and/or S5 as described above.

In a third example, step S3 is performed in respect of plural feature vectors 12 derived by performing steps S1 and S2 on plural polymers that are fragments of a common polymer. In this case, in step S3, the plural derived feature vectors 12 are compared with each other and the similarity therebetween is determined in overlapping parts of the feature vectors 12. This allows information on the common polymer to be built up from the input signals of the fragments.

A fourth example of step S3 is similar to step S5, but involves comparison of the derived feature vector 12 a feature vector 14 stored in a memory 15. In this comparison, similarity is determined to identify localized regions where the derived feature vector 12 is dissimilar to that feature vector 14 in the memory. This fourth example has similar advantages to step S5 above, but is applicable where the expected type of the polymer is known in advance and so the comparison can be made with a feature vector 14 in respect of that expected type, without needing to classify the derived feature vector 12 first.

There will now be discussed some of the mathematical techniques that may be applied in steps S3 and S5 to determine similarity.

One approach is to modify existing pairwise dynamic programming sequence alignment algorithms e.g. the Needleman-Wunsch algorithm for global alignment or the Smith-Waterman algorithm for local alignment.

The modifications may include replacing the substitution matrix with a distance measure operating on the feature vector. For example the distance measure may be a measurement of the absolute difference in current between the data points. The distance function could also consider multiple measurements at each position e.g. mean and variance of a current measurement.

Modification may also be made to the to the gap scoring mechanism as are known in the art, for example constant gap penalties, linear gap penalties or affine gap penalties.

These algorithms output an alignment score that is a function of the two feature vectors, the distance function and the gap penalties. The alignment score can be used to determine similarity.

These modified alignment algorithms can be used for clustering, consensus building, and pattern matching although other methods can also be used to achieve these tasks.

Multiple alignment algorithms may also be modified in similar ways to those described for pairwise alignments.

Rather than match feature vectors by using gapped alignment techniques as described above, an alternative approach is to represent the feature vector in terms of shorter sub-vectors, typically comprising consecutive entries in the feature vector. For example, if the feature vector was (1,2,3,4,5) then we could represent it by length 3 sub-vectors to give the new representation {(1,2,3), (2,3,4), (3,4,5)}. For our application the sub-vectors are frequently considerably longer (>10) so maintaining much of the time-ordering information.

Similarity of feature vectors on the basis of sub-vectors is then defined on the basis of how closely the set of sub-vectors match. This has the potential to be a more efficient means of comparison than gapped alignment type algorithms, since we may compare sub-vectors directly without allowing for gaps.

If the feature sub-vectors are suitably discretized (for example by rounding each number to the nearest 0.1) then exact or partial matches of sub-vectors may be used, and similarity calculated in terms of what proportion of sub-vectors match or partially match. Discretisation also enables integer arithmetic to be used for comparison. Alternatively hash functions may be applied to sub-vectors to give fixed length "fingerprints" (see for instance Karp, R., Rabin, M. (1987) "Efficient randomized pattern matching algorithms"/ IBM J. Res. Development 31:249-260.) denoting presence or absence of sub-vectors which can be rapidly compared.

Similar ideas in terms of matching sub-strings are used by algorithms like BLAST (Altschul, S. F., Gish, W., Miller, W., Myers, E. W. & Lipman, D. J. (1990) "Basic local alignment search tool." J. Mol. Biol. 215:403-410.) that split data into short fragments and match these against a large library.

An alternative approach is to use an HMM (Hidden Markov Model) Viterbi path as follows.

In general, alignment-based and sub-vector based measures of pairwise similarity treat the pair of feature vectors that are being compared in the same way. The result is that given a pair of feature vectors A and B, the similarity of A to B is equal to the similarity of B to A.

However, where one of the feature vectors to be compared is a library feature vector, it is natural to treat the problem as if that feature vector were the "model" or "training sequence". In this case, an alignment can be performed using HMM methods with models constructed in a similar manner to the "forced path" training models described previously (U.S. 61/538,721, GB1117574.2). Algorithms other than Viterbi that are known in the art may also be applied, for example the Forwards-Backwards algorithm. As in the case of alignment algorithms, there is an output score that can be used as the measure of similarity. In the case of Viterbi this is the total likelihood of the path. The total likelihood is not guaranteed to be equal if we swapped the roles of the two feature vectors, however for classification problems in particular, this is not generally an issue.

For clustering, the following approaches may be applied.

Clustering is performed on input signals 11 from a measured population of polymers, and involves determining the number and/or types of polymer present according to some similarity criteria.

Given a matrix of distances (or similarities/dissimilarities), methods for hierarchical clustering are well known and covered in standard monographs (for example Gordon, A. D. (1999) Classification, $2^{nd}$ edition. Chapman and Hall/CRC). Hierarchical agglomerative methods are also used for sequence alignment in packages such as CLUSTAL (Higgins, D. G. and Sharp, P. M. (1988). CLUSTAL: a package for performing multiple sequence alignment on a microcomputer. Gene, 73, 237-244.)

Using global or local alignment algorithms, all feature vectors are pairwise aligned with each other such that we have a measure of similarity (or in some cases distance) between each pair of feature vectors. These similarity values can be written down as a similarity matrix with the (m,n)th entry containing the similarity of the m'th to the n'th feature vector. A clustering technique is then used (typically hierarchical agglomerative clustering) based on that similarity matrix.

Two extremes of agglomerative clustering are single-link (score a pair of clusters during the agglomerative step on the basis of the most similar feature vector pair) and complete-link (score a pair of clusters based on the most dissimilar feature vector pair) clustering. The best combination of algorithm to determine similarity and clustering technique is dependent on the nature of the clusters expected for a given application.

For example, if clusters are expected to be made up of feature vectors with overlapping fragments of pairs of feature vectors showing high similarity, local alignment scores and single-link agglomerative clustering would be one appropriate choice. An example of this is shown in Worked Example 2, where sequences 1 and 2 overlap as do sequences 2 and 3. If in our clustering task we wished to identify these as a single cluster amid some other feature vectors, we would be most likely to be successful using a local alignment score to correctly identify the short overlapping regions. Single-link clustering would join the sequences into the same cluster because 1 has an overlap with 2 and 2 has an overlap with 3, however complete-link agglomerative clustering would be a poor choice since sequences 1 and 3 have no actual overlap in sequence space and hence are likely to have low similarity in terms of feature vectors.

Where clusters are expected to be near-identical across the entire feature vector (for example, where feature vectors have already been identified to begin and end in approximately the same place relative to a known reference, and we are looking to discover classes that vary subtly from that reference) global alignment scores and complete-link agglomerative clustering would be more appropriate.

In many contexts, it is useful to be able to generate a single reference feature vector to represent a group/cluster/class of similar and overlapping feature vectors. The following is an outline of an iterative algorithm that can be used to achieve this.

1. Generate a long initial feature vector. We call this the landmark vector.
2. Align each feature vector to the landmark vector.
3. Generate a new, empty, landmark vector.
4. Moving from start to finish along the aligned feature vectors from step 2, whenever a proportion p of the aligned feature vectors lie within a range r, add the mean value at that position to the landmark vector.
5. Repeat 2-4 until the landmark vector produced at step 4 is identical for consecutive iterations, or a maximum number of iterations is reached.

Alternatively, the landmark vector can be updated based on many or all possible alignments.

The landmark vector produced as a result of this process with the feature vectors aligned to it produces a "consensus" of the feature vectors.

In step 1, all pairs of feature vectors may be aligned and the aligned pair with the most states picked, subject to some minimum level of similarity, taking the mean at each position where the states align to generate the initial feature vector. Alternatives are possible, for instance just picking the longest feature vector.

The pairwise alignment algorithms used in step 2 are described above.

In step 4, p and r can be varied according to the particular situation, mean may be replaced by some other measure of location, and r may be replaced by some other measure of spread.

This consensus building process provides a multiple alignment algorithm in terms of feature vectors. The landmark-aligned states give a fixed length vector representing each feature vector.

Some approaches to classification are as follows.

The task for classification is to assign a "query" feature vector to one of m classes for integer m>1. There is a library of "target" feature vectors 14 in the memory 15 belonging to these m classes.

Method of solution is dependent on whether the target feature vectors are heterogeneous (mutually dissimilar at a global level) or are homogeneous (all globally similar to each other, with some relatively subtle differences, typically localized, differences), although clearly there are cases that lie between these extremes where mixtures of methods are appropriate.

In the heterogeneous case, the simplest method for class determination is to calculate similarity between the query feature vector and the target feature vectors by one of the methods described above and to assign the query feature vector to the class with the target feature vector of maximum similarity.

If there are multiple target feature vectors per class, then a summary target feature vector may be derived for each class, containing for instance the mean value across target feature vectors in that class, and proceed as before. For alignment-based similarity measures, it is needed first to perform a multiple alignment of the feature vectors using, for example, the "Consensus Building" process described above.

Alternatively each target feature vector may be treated independently. For instance, in the simplest case, the query feature vector is assigned to the class of the closest target feature vector. For this approach to be as successful as possible, a re-weighting of statistics to account for the different number of target feature vectors per class is frequently desirable.

Although an alignment of all target feature vectors across all classes is not generally possible in the heterogeneous case, we can nonetheless use learning algorithms to derive classifiers. The vector of distances or dissimilarities to target feature vectors can be used as the input to multivariate learning techniques such as multi-class linear discriminant analysis to produce an improved classifier. Alternatively, a fixed length vector may be produced from sub-vectors using standard hashing algorithms as described earlier and this used as the input to learning algorithms. More about learning algorithms in the homogeneous case follows.

It is generally possible for many methods to output not just a most likely class, but a probability of the classification being correct.

In the homogeneous case, the same or similar methods may be applied as in the heterogeneous case, however random variation across the feature vector may well mask the systematic local variations that are of primary interest and provide the key information to correctly discriminate between classes.

Hence it is frequently more efficient to learn what the key differences between the target feature vectors are; or more generally, given a training set of feature vectors with known classes, to learn rules for correct classification that allow us to predict the class of feature vectors.

Unlike the heterogeneous case, feature vectors may initially be aligned to a common reference feature vector (for instance the landmarks from consensus alignment of the target feature vectors), similarly to the "Consensus Building" case above, and the states aligning to landmarks fed as a fixed length input vector to learning algorithms.

Given a training set of feature vectors of known class, standard statistical and machine-learning classification techniques may be used to predict the class of a new feature vector. For instance, a decision tree classifier (for example, but not limited, to C4.5. Quinlan, J. R. (1993) C4.5: Programs for Machine Learning. Morgan Kaufmann Publishers) can learn that particular positions of the reference-aligned feature vector are above a particular value for one class only. So-called black box methods such as neural networks, random forests and support vector machines may be used to make predictions of class membership, while not necessarily generating interpretable rules. In an alternative method, Bayesian networks may be implemented, where expert knowledge may also be incorporated.

It may be of particular interest where classes vary around the same position after alignment to the reference (for instance corresponding to less conserved regions of the genome). In this case, given an alignment, one can look directly for one-or-more consecutive positions with high between-class variation compared to within-class variation.

It is generally beneficial to use standard techniques such as cross-validation and hold-out sets with these methods to avoid over-fitting and gain an idea of generalizability.

Rather than begin with an alignment step, we also use sub-vectors as inputs to learning algorithms. A fixed length vector may be produced from sub-vectors using standard hashing algorithms as discussed earlier and this used as the input to learning algorithms. Alternatively, the sub-vectors themselves may be used directly—for instance with an algorithm searching for sub-vectors that only have near neighbours within-class.

Problems that do not obviously fall into the homogeneous or heterogeneous cases may be treated using a mixture of methods from the two cases, in particular by first subdividing the problem space into homogeneous groups of classes using clustering (similarly to "Clustering" described above).

There will now be described approaches to determination of localized regions where the derived feature vector 12 is dissimilar to another feature vector, e.g. in step S5 or the fourth example of step S3.

Generally, an alignment to the target feature vector is performed and then positions that vary between the query feature vector and the target feature vector are identified.

Where there is more than one target feature vector from a single class, a reference feature vector is generated (for example the landmarks described in the "Consensus Building" above) from the target feature vectors, and the target feature vectors are aligned to the reference feature vector to gain an idea of location and variability at each position in the reference (for example by calculating the mean and standard deviation of the aligned target feature vectors at that position). Localised regions where the query feature vector shows a pattern of values unlikely to be produced in the target class may then be identified, for example by looking at the total likelihood across a number of consecutive reference-aligned states if we assume each distribution to be Gaussian with mean and standard deviation estimated from the target feature vectors.

The methods may be extended to look at differences between classes of feature vectors as discussed in the homogenous case of classification above. These classes may be pre-defined, for example they may be DNA samples from patients with and without a particular disease. Alternatively, they may be derived by clustering in the first instance.

Equally, many of the statistical and machine learning techniques (such as decision trees) discussed above in the context of homogeneous classification methods are also used to discover localized regions that differ between pairs or classes of feature vector.

There will now be described approaches to assembly of large feature vectors from fragments of feature vectors, e.g. in the third example of step S3 above.

The majority of existing assembly algorithms can be modified to use the feature vectors of the present type. The consensus methods described above may be appropriate for some assembly applications. Generally the following method may be used.

Feature vectors are first "discretised". A transformation is applied to each series of measurments may include any one or combination of the following:
1. Representing the feature vector as a series of deltas.
2. Representing the feature vector as a series of classes based on current level.
3. Representing the feature vector as a series of milestone (well characterised) features.

Once the trace is discretised, standard assembly algorithms may be used. For example seed sequences maybe extracted, and used in overlapping. The overlapper will then orientate the reads using the feature vector space transformation.

Existing assembly algorithms that may be applied include Zerbino & Birney, "Velvet: Algorithms for de novo short read assembly using de Bruijn graphs", Genome Res. 2008. 18: 821-829 and Batzoglou, S. "Algorithmic challenges in mammalian genome sequence assembly", (2005) Encyclopaedia of genomics, proteomics and bioinformatics, ed Dunn, M., et al. (John Wiley and Sons, New York) Some specific applications of the present invention are now set out by way of non-limitative example.

A first application is in counting molecules against a known library or panel of molecules, which may use a method involving the first example of step S3.

The library comprises the feature vectors 14 stored in the memory 15. Such libraries may be generated for later use, using either supervised or un-supervised learning, based on individual experiments for each molecule or for sets of molecules to learn the feature vectors.

For example one may have a set of DNA/RNA sequences of known disease. The fingerprints of these molecules may be known in advance, either from measurements or generated from a model. Given a measurement of a molecule, this can be compared against the known library and the similarity of the molecule to the library members measured. This allows identification of each molecule measured (this identification could be "other") and quantification of the relative numbers of each type of molecule measured.

Examples of things that can be counted with reference to a library or reference panel are as follows:

Expression profiles: comparing abundance of mRNA transcripts by matching feature vectors. This can be used to measure changes in expression levels. Such gene expression might change during development, disease, treatment for the disease, between one organ and another.

Abundance of biomarker miRNAs: these are, typically, 20-25-mer RNA oligonucleotides that circulate in blood, and changes in the expression level of groups of these is associated with certain diseases, particularly cancers. One could compare to a defined panel, so there would be a relatively small search space for pattern matching.

Foetal copy number variation in circulating blood: fragmented foetal DNA circulates in maternal blood. If the foetus has an aneuploidy, e.g. an additional copy of chromosome 21, 18, 11 (the main ones that are not immediately fatal) it would be possible to design capture probes to, for example, exons of the chromosomes of interest, so as to enrich them for pore analysis, and to then compare these to reference feature vectors and to count. The main limitation of current methods for this is the inability to distinguish between maternal and foetal chromosomes. There are differences in methylation status between foetal and maternal DNA that are not visible to next gen sequencing that uses PCR, but which would be visible as differences in feature vectors.

Comparative genomic hybridization (CGH): changes in copy number of various genomic regions can be altered in tumour cells (and also in foetuses, as described above). For a while, this was identified by comparative genome hybridisation, i.e. where patient/sample is compared to reference by hybridising fragmented genomic DNA to a set of probes on an array. As with foetal testing, feature vector space can be used to profile these copy number changes.

Viral or bacterial load: a measure of the severity of infection. Possibly in conjunction with some form of enrichment, the number of pathogen RNA or DNA copies per ml of blood is measured. It would not have to be done on the whole pathogen genome. Early stage and late stage measurements may be carried out to identify antigenic drift and/or antigenic variation.

The method may be applications in epidemiology, for example in identification (strain typing) and how a disease is spreading or evolving. The method may be used for example to monitor the efficacy of a particular drug therapy or monitor the spread of disease from one area of the body to another or spread of disease between patients.

Probes: There is provided a small population of probes (eg. aptamers to a biomarker panel), some of which attach to a target molecule. Those that didn't bind are separated from those that did, and molecules are counted in the unbound population or in the bound population to quantify the target molecules.

The identity of organisms could be determined, e.g. in food or in cultures.

A second application is in quantification of major population(s) and measurement of "other" present in a sample.

As an example, one can consider synthesis of a DNA oligomer. Current quality control methods typically involve Polyacrylamide Gel Electrophoresis (PAGE), High-performance liquid chromatography (HPLC) and mass spectrometry. One could measure a sample of the synthesised DNA and determine the signature of the major population present. It is then possible to count the number of molecules in the sample that are different from the major population, possibly indicating errors in synthesis. In particular if the differences occur at particular positions in the feature vectors it may be due to a systematic error that can be rectified by adjusting the synthesis conditions. Any improvements could then be verified by repeating the nanopore measurement.

A third application is in measurement of modifications/differences at positions and quantification of those modifications/differences within a population of molecules.

One example is calling of single-nucleotide polymorphisms (SNP). Known positions compared to the four (or more) allowed nucleotides at that position. The presence and/or absence of a SNP at a known location compared to the "wild-type". This may enable identification of new loci. Similarly it may enable identification of paralog-specific variants in non-allelic homologous recombination (NAHR) as discussed later.

Another example concerns methylation. Measurements can be made at known methylation sites. The method allows identification of the presence, absence and/or quantification of methylation at those sites. The method also allows identification of unknown sites. The method allows estimation of "bulk" methylation state of individual molecules, for example whether 100% of the population is 50% modified or 50% of the population is 100% modified, e.g. for use in foetal screening as described above. The methylation state of certain genes can be used as a biomarker for cancer Another example is identification of splice variants and/or translocation breakpoints. This is similar to the examples described earlier, but one identifies the position where feature vectors stop matching, or where one half of a feature vector maps to one locus and the other half maps elsewhere.

A fourth application is in identification of the presence and/or absence to a desired confidence of a particular known molecule.

This is similar to comparison to the first application, but here there may be interest in one particular molecule.

This method may be used to identify populations of molecules that are related, but not identical to the known molecule to a particular degree of confidence (similar to measurements of homology of DNA or protein sequences), for example in rapidly mutating diseases.

Another example concerns fusion transcripts, as in splice variants. Detection of specific fusion transcripts is used in cancer diagnosis, e.g. the presence of the Bcl-abl fusion transcript indicates leukaemia.

Another example concerns diagnosis of NAHR. During meiosis, recombination between similar but non-allelic loci results in deletion or duplication of fairly large chunks of genome, with catastrophic consequences for the foetus arising from such a gamete. This will cause a change in copy number of the affected loci (see CGH above), but also results in a fusion of the non-allelic homologs, which would be detectable by looking at PSVs (like SNPs but not the same).

Another example concerns the case where plural parts of the derived feature vector are compared to plural stored feature vectors. For example the DNA sequence for known protein domains may be used to generate the library feature vectors and the DNA that codes for an unknown protein measured. Part of the derived feature vector may be identified with for example a catalytic domain and another part with for example a DNA binding domain. Thus the function of the protein may be deduced.

A fifth application concerns assembly.

From a collection of molecules reading smaller, partially overlapping feature vectors, either randomly split, systematically split, or split by some other mechanism from a larger molecule, one can assemble the complete larger feature vector. Similar algorithms (adapted) to those used for sequence assembly may be used. Alternatively, one may generate a rough template feature vector from known properties of the molecule (e.g. if the DNA sequence is known) and the small fragments mapped to that template feature vector. In the case where the template was approximate, the template can be refined throughout the process.

Libraries may be derived experimentally or be generated informatically.

Examples of the type of library used may include without limitation feature vectors constructed from known DNA sequences using a model, from known protein sequences, from known polymers, feature vectors derived experimentally, feature vectors assembled from overlapping derived feature vectors, feature vectors derived from the consensus of clustered measurements. Libraries may comprise plural related feature vectors, plural unrelated feature vectors, heterogeneous or homogeneous sizes of feature vectors, similar feature vectors with localised differences.

An example where libraries of feature vectors corresponding to DNA fragments are derived experimentally may use fragments produced systematically, for example by enzymatic fragmentation, or fragments produced randomly, for example by mechanical shearing or through non-selective enzyme action. Randomly fragmented derived feature vectors may preferentially be assembled into larger derived feature vectors for use in a library. Systematically fragmented libraries may preferentially be used as library feature vectors covering similar regions to the fragmentation pattern.

An example where a library of feature vectors is derived informatically may utilise available databases, for example the NIH Genbank database (Nucleic Acids Research, 2011 January; 39(Database issue):D32-7) which contains publically available DNA sequences. To derive, for example, the feature vectors for mean current corresponding to those sequence, a model may be used derived from a training process such as that used previously (U.S. 61/538,721, GB 1117574.2, N114722). The library may be reduced to those sequences that are of interest for the particular application, for example the library may be reduced to coding regions of the human genome.

There will now be described some examples of use of the present invention.

Example 1 concerns data acquisition in a typical nanopore experiment with the following experimental conditions:

Buffered solution: 1 M NaCl, 100 mM Hepes pH 8.0, 1 mM ATP, 1 mM $MgCl_2$, 1 mM DTT, 10 mM Potassium Ferrocyanide (II), 10 mM Potassium Ferricyanide (III), Pt electrodes.

Nanopore: MS(B2C)8 MspA MS-(G75 S/G77S/L88N/D90N/D91N/D93N/D118R/Q 126R/D134R/E139K)8

Enzyme: Helicase 100 nM

Electrical measurements were acquired from single MspA nanopores inserted in 1,2-diphytanoyl-glycero-3-phosphocholine lipid (Avanti Polar Lipids) bilayers. Bilayers were formed across ~100 μm diameter apertures in 20 μm thick PTFE films (in custom Delrin chambers) via the Montal-Mueller technique, separating two 1 mL buffered solutions. All experiments were carried out in the stated buffered solution. Single-channel currents were measured on Axopatch 200B amplifiers (Molecular Devices) equipped with 1440A digitizers. Pt electrodes were connected to the buffered solutions so that the cis compartment (to which both nanopore and enzyme/DNA are added) is connected to the ground of the Axopatch headstage, and the trans compartment is connected to the active electrode of the headstage.

After achieving a single pore in the bilayer, DNA polynucleotide and helicase were added to 100 μL of buffer and pre-incubated for 5 mins (DNA=1.5 nM, Enzyme=1 μM). This pre-incubation mix was added to 900 μL of buffer in the cis compartment of the electrophysiology chamber to initiate capture of the helicase-DNA complexes in the MspA nanopore (to give final concentrations of DNA=0.15 nM, Enzyme=0.1 μM). Helicase ATPase activity was initiated as required by the addition of divalent metal (1 mM $MgCl_2$) and NTP (1 mM ATP) to the cis compartment. Experiments were carried out at a constant potential of +120 mV.

The analyte DNA samples used in this study are shown as ANA ID NO. 1-19.

Example 2 concerns identification and quantification of particular DNA molecules from a panel of DNA molecules. This example describes the process of identification of DNA molecules in a solution from a pre-determined library of feature vectors.

Library Construction was performed as follows. The library was constructed by taking 18 approximately 400 mer sequences (ANA ID NO 1 to 18), each overlapping the previous sequence by approximately 100 bases from a 5 kilobase genome (PhiX174). For example, ANA ID NO 2 will share 100 bases with ANA ID NO 1 and 100 bases with ANA ID NO 3). These sequences contain a sequence at the beginning and a sequence at the end, common to all strands and not part of the larger genome. The overlapping sequences allow a demonstration of identification of different molecules, even in the presence of large similar regions. The library feature vectors are constructed for the mean current by considering a model of the current associated with each 5 mer position (1024 values). The determination of this type of model has been disclosed previously (for example in U.S. 61/538,721, GB 1117574.2, N114722).

Figure 12:
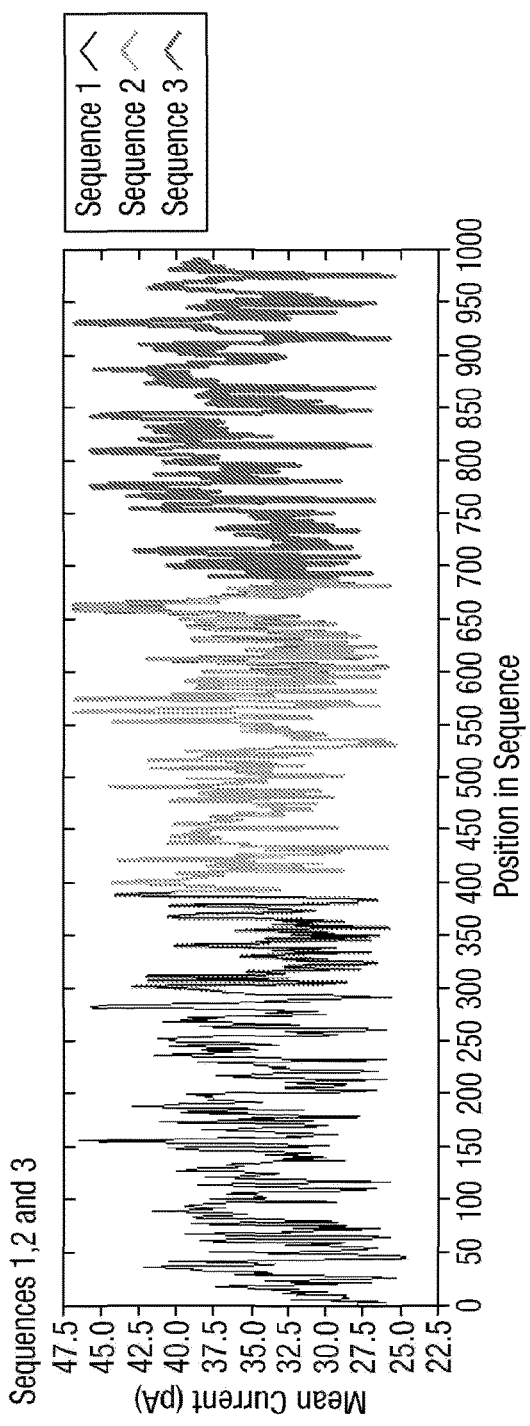
FIG. 12 is plot of feature vectors for three fragments of a sequence identified by their overlap, for Example 2 of the method.

Feature Vectors for sequences 1, 2 and 3 are shown in FIG. 12, which illustrates overlapping sections. Common ends (as described above) of each sequence have been removed for this illustration.

Candidate molecule feature vectors were obtained as follows. Candidate molecules were acquired using the experimental methods describe above and in Example 1. Candidates are reduced to feature vectors consisting of the mean current between identified transitions as described previously.

An example candidate belonging to one of the sequences (ANA ID NO 1 to 18) was considered. This molecule was compared against the library (ANA ID NO 1 to 18) using an alignment algorithm as described above. The output score from the alignment is used as a measurement of similarity to each of the library members.

Figure 13:
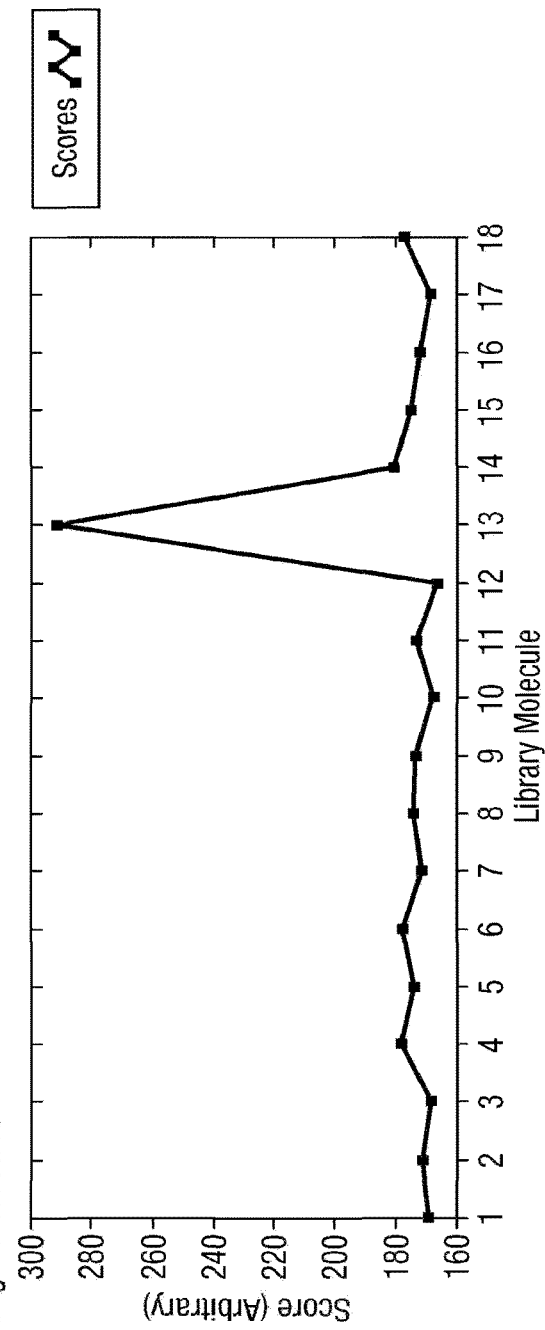
FIG. 13 is a plot of similarity scores for candidate molecule as compared to all library sequences in Example 2.

Comparison by alignment was performed. The output scores from the library comparison are shown in FIG. 13. One can see that the score for one of the library members is much higher than those for all the other library members. This is true across a range of reasonable parameterisations of the alignment. Here a gap penalty of −1 and a scoring function of reciprocal absolute difference is shown (i.e. closer matches are higher scores).

Figure 14:
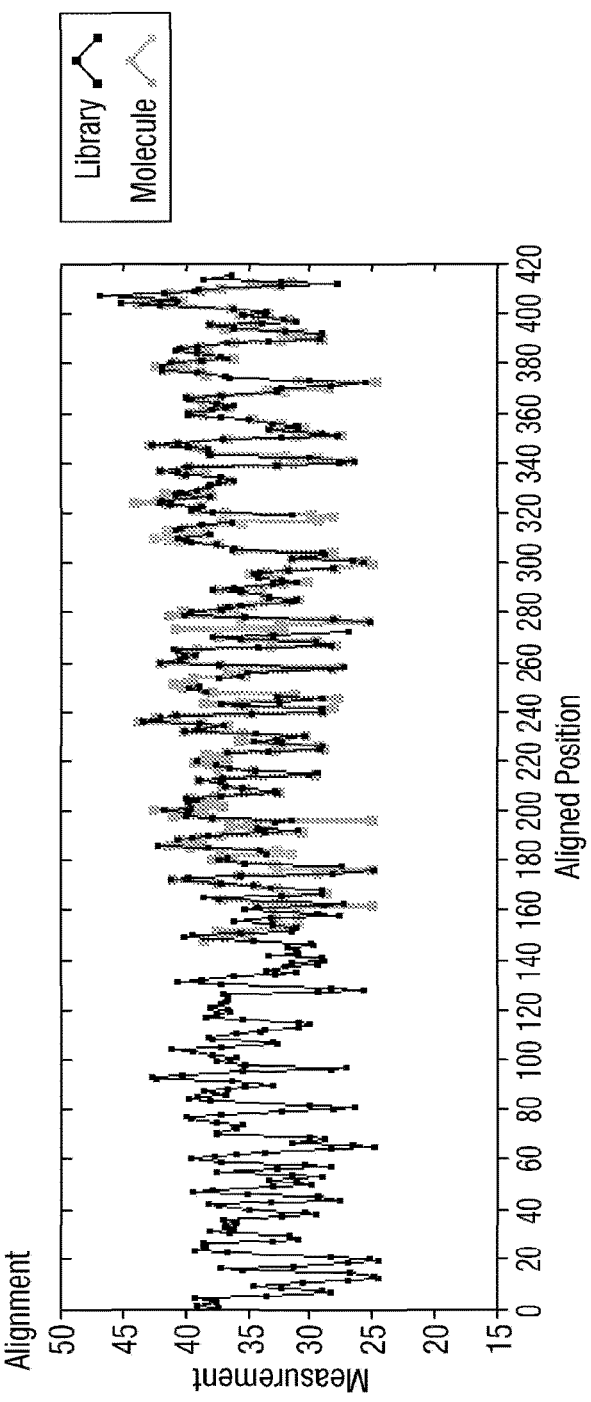
FIG. 14 is a plot of a candidate molecule aligned with best match library molecule in Example 2.

Closer inspection of the alignment with library molecule 13 (ANA ID NO 13) shows that a close match is indeed present, as shown in FIG. 14.

Figure 15:
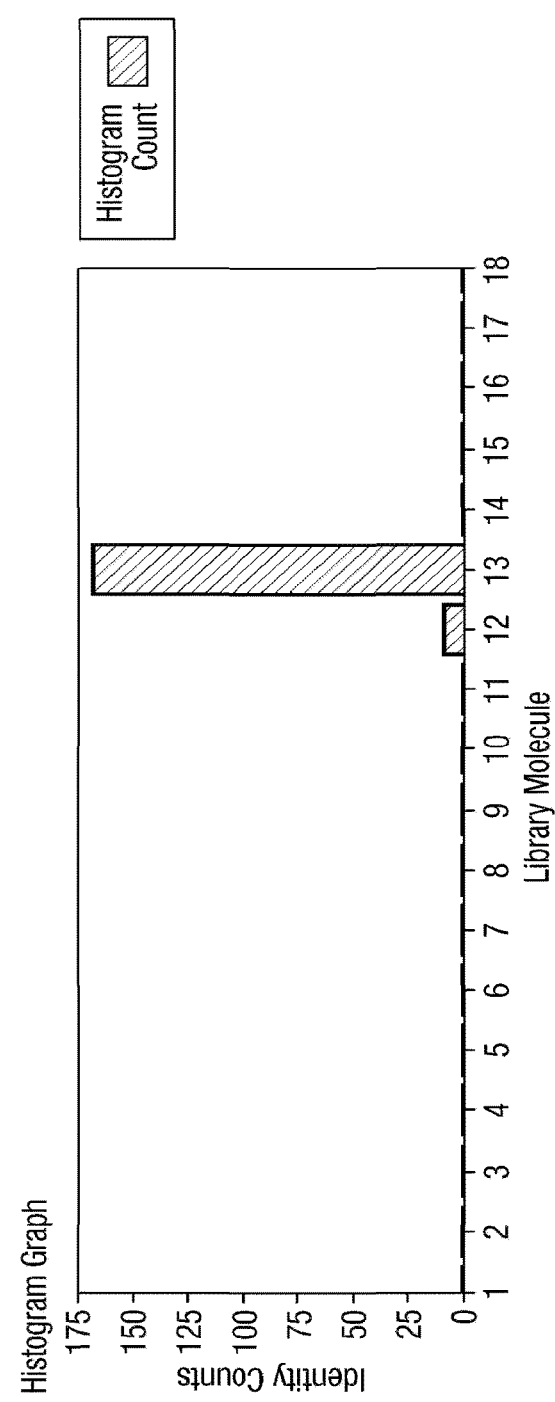
FIG. 15 is a histogram of classification for 176 candidate molecules in Example 2.

This was run for all the candidate molecules in this experiment (all molecule 13) and one can see that in most cases the molecule was correctly identified as molecule 13. In cases where the molecule was not correctly identified, these are mis-identified as molecule 12 (ANA ID NO 12). These are typically partial reads of the molecule, containing mostly the shared overlapping sequence. A histogram of identifications is shown in FIG. 15. We count 168 instances of molecule 13, correctly identified in this experiment.

Example 3 concerns measurement of single-nucleotide polymorphisms (SNPs) in a DNA fragment.

Figure 16:
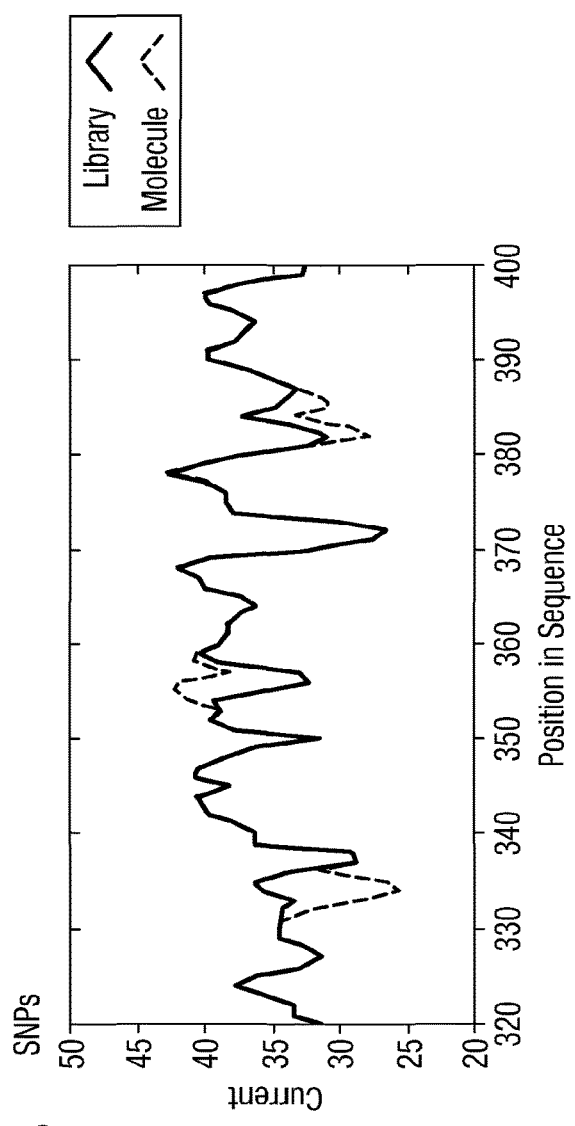
FIG. 16 is a graph of the feature vector in Example 3 of the method, illustrating the effect of SNPs on molecule 13.

Library construction and feature vectors were generated using methods as presented above, however in the library feature vector for molecule 13 (ANA ID NO 13), there were made three changes to the sequence [old][position][new], T335A, G357T, C385A (ANA ID NO 19). Any examples of molecule 13 will have changes at these positions relative to the library molecule (i.e. 3 SNPs). The effect of these SNPs on the library feature vector is shown in FIG. 16.

Figure 17:
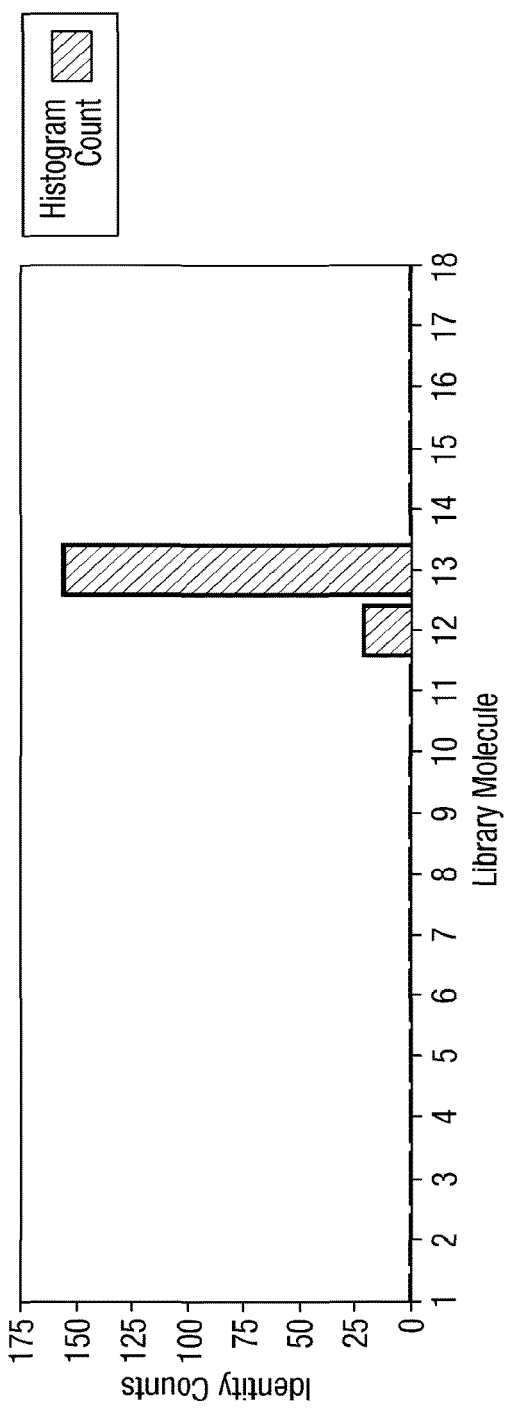
FIG. 17 is a histogram of classification for 176 candidate molecules with three SNPs in molecule 13 in Example 3.

The alignment based identification method of the previous example was repeated, demonstrating that these SNPs do not have a significant impact on the identification of the molecules. The majority of molecules are still correctly identified with a slightly higher tendency to mis-identify given the SNPs. The increased tendency is due to the sequences for ANA ID NO 12 sharing the same sequence but without the SNPs. A histogram of identifications is shown in FIG. 17.

Figure 18:
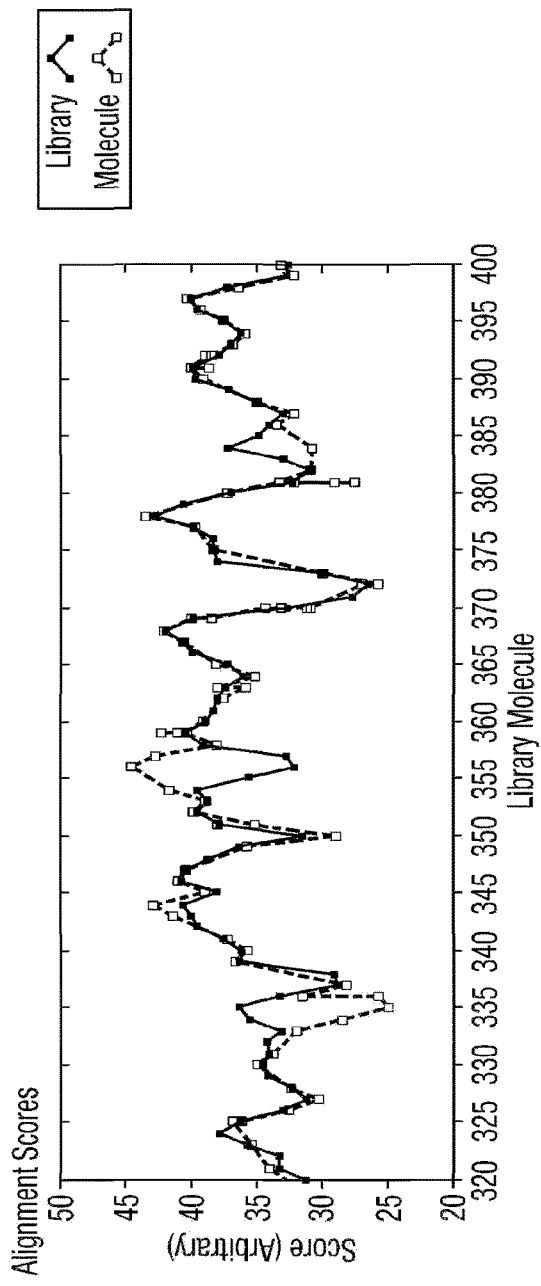
FIG. 18 is a graph of the alignment of a measured molecule with the library feature vector in Example 3.

For SNP calling, an HMM and a Viterbi path was used for alignment since this has a better path constraint (i.e. will align better through the mismatches SNP regions) than e.g. Needleman-Wunsch with parameters used previously. Alignments shown in FIG. 18 compare well with the idealised library mutations shown earlier. The three SNPs are clearly observable in FIG. 18.

Figure 19:
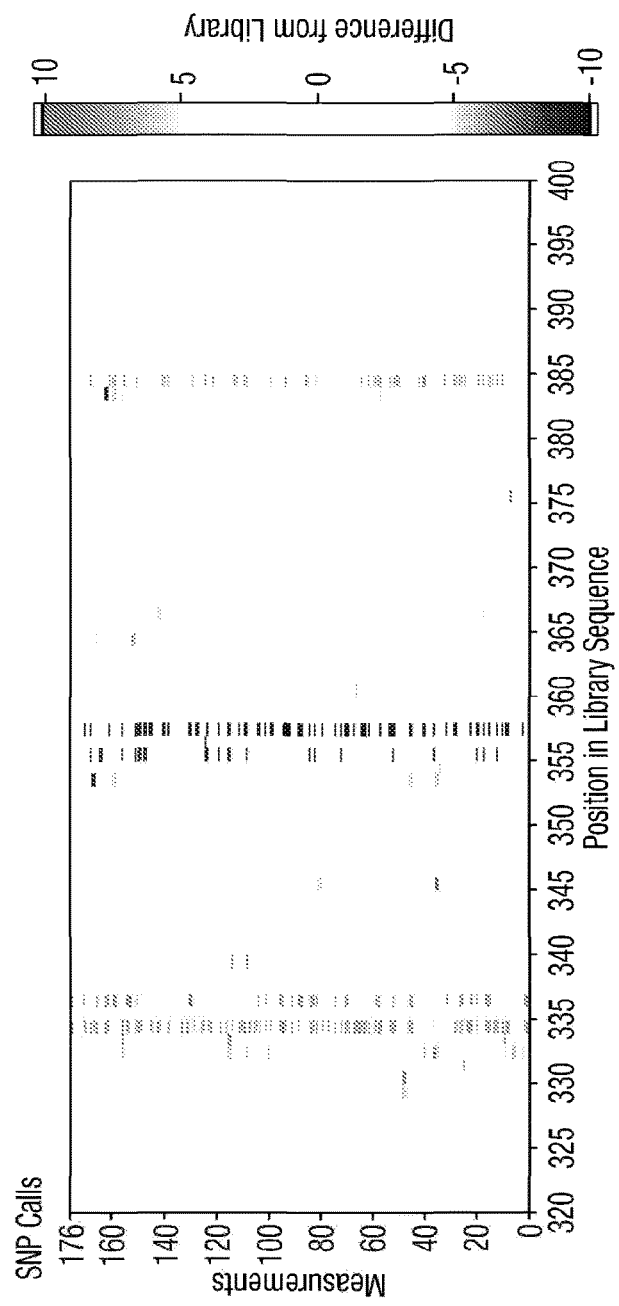
FIG. 19 is a plot of position-resolved differences between measurements and library feature vectors, illustrating position of SNPs, in Example 3.

Looking across a dataset of 176 molecules these SNP positions can be clearly identified. FIG. 19 shows the difference in current between Viterbi aligned library and candidate feature vectors. The three SNPs are visible, in the case of 335 and 357 at several positions as several of the measured features are affected by each single change (i.e. a single change to sequences affects several adjacent kmers).

Figure 20:
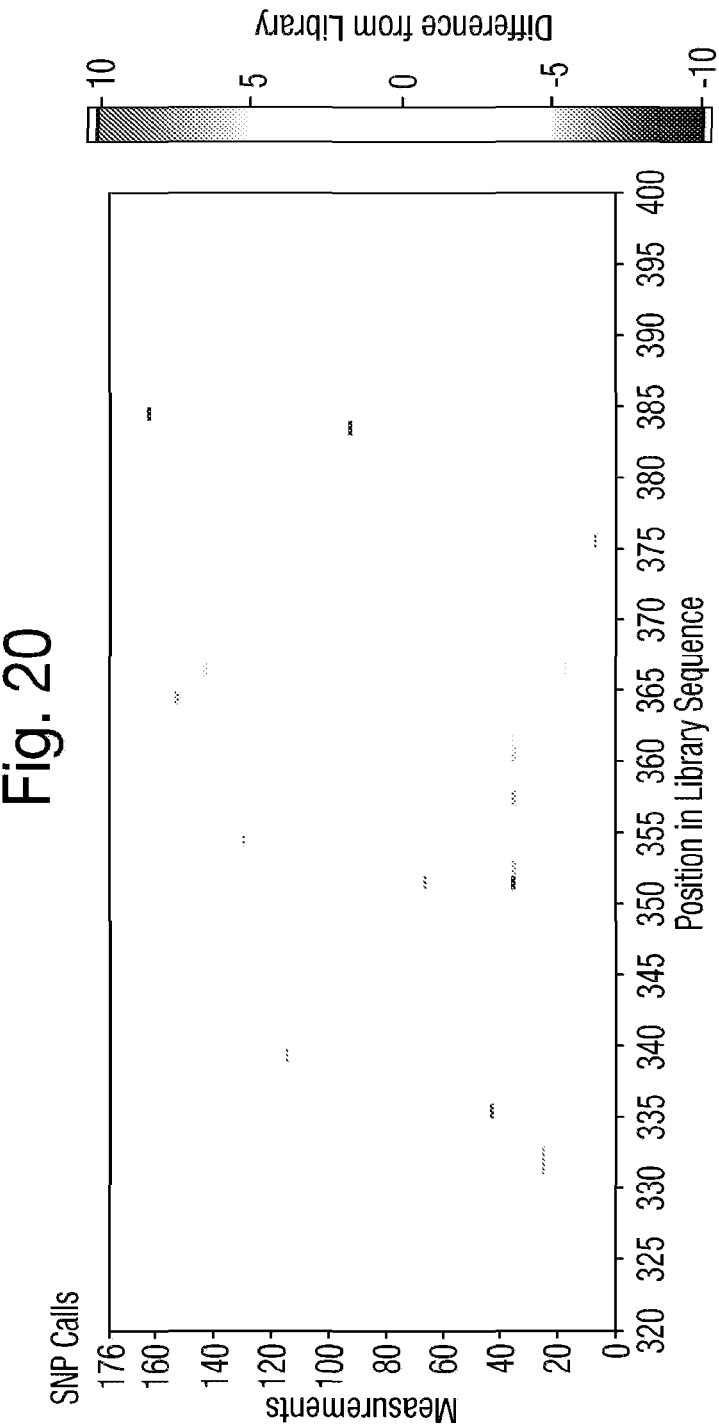
FIG. 20 is a plot of position-resolved differences between measurements and library feature vector without SNPs in Example 3.

The control version of this experiment was run, using the library feature vector for ANA ID NO 13 without the SNPs. In this case no consistent difference is identified from the library, as shown in FIG. 20 wherein no positions display a consistent deviation.

Example 4 concerns identification of a major population and measurement of a sub-population that is similar but different.

This example is worked through with simulated data. A set of 60 feature vectors (of mean current) is simulated of ANA ID NO 13. Ten of the simulations also contain a SNP. Gaussian noise with standard deviation of 1 pA is added to each value and 5% of values within each vector are deleted at random. Apart from simulating the data, no more knowledge of the sequence is used.

Figure 21:
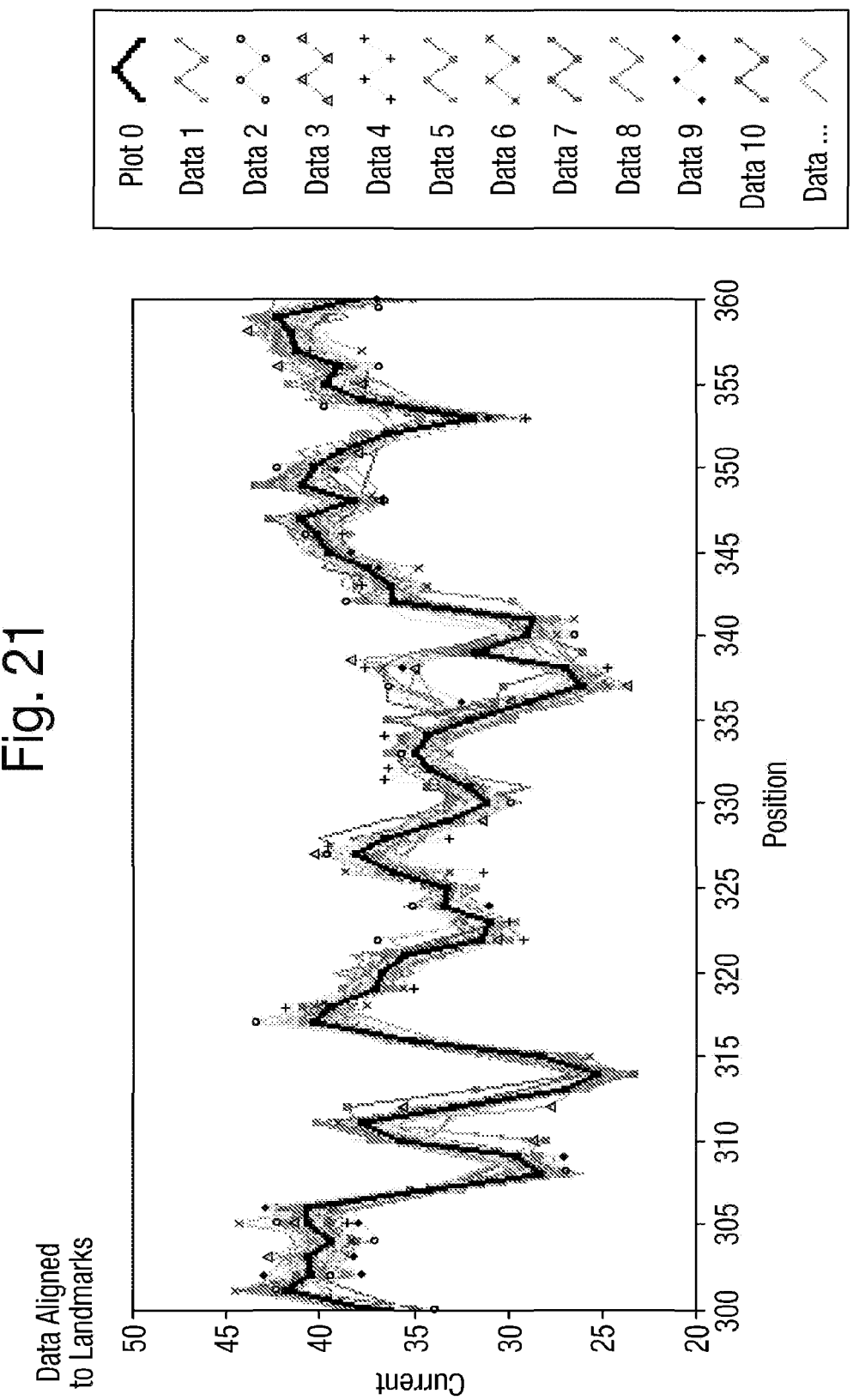
FIG. 21 is a plot of the final alignment of data with consensus landmarks in Example 4 of the method.

Using this dataset (and no knowledge of the sequence) a consensus is constructed via the landmark process described previously. FIG. 21 shows the final output of this process with all the data aligned to the consensus. We clearly see the region where the SNP is contained at approx. position 337.

Figure 22:
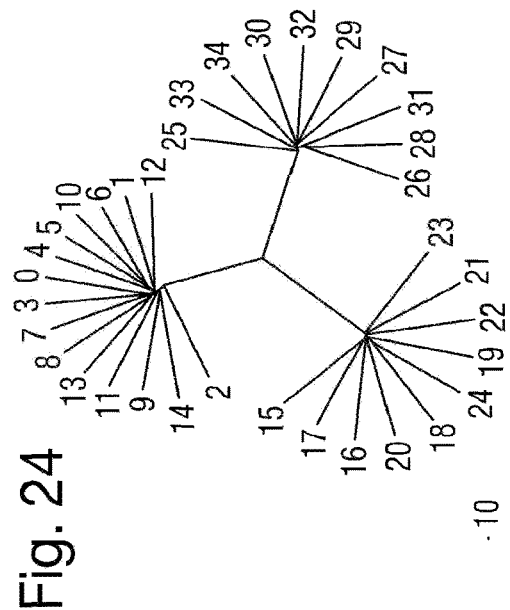
FIG. 22 is a plot of position-resolved differences in candidate molecules 51-60 at approximately position 337 in Example 4.

Performing the same analysis as for Example 3 one can see the SNP usually identified in molecules 51-60, as shown in FIG. 22.

Example 5 concerns identification of a number of populations, generation of a library and a relative count.

Figure 23:
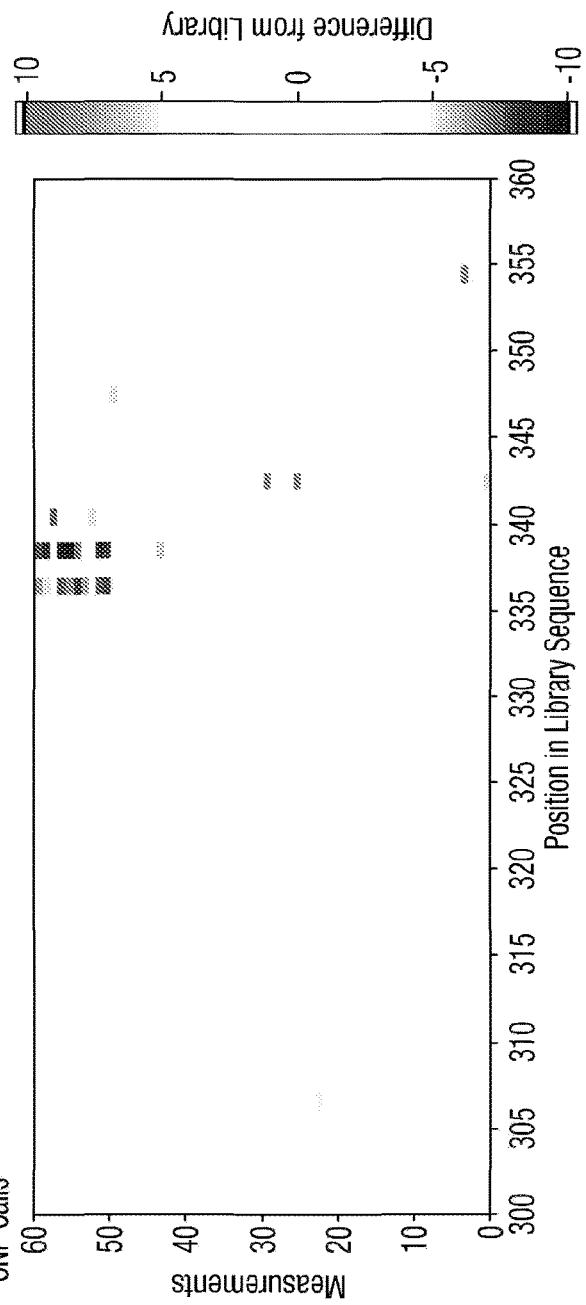
FIGS. 23 and 24 are diagrams of trees formed by neighbour joining on alignment similarity scores for a two cluster and a three cluster dataset respectively, in Example 5 of the method.
Figure 24:
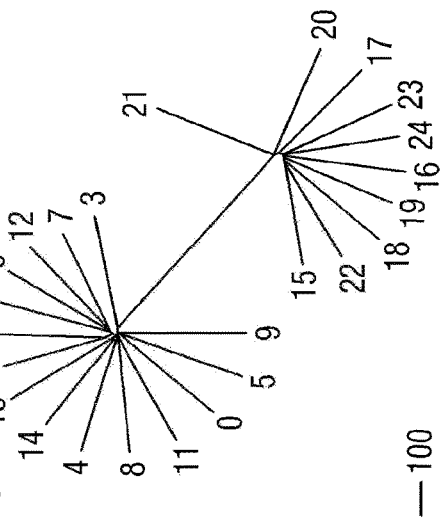

Two cases are considered, firstly where there are two species present, and secondly where there are three species. Data are simulated using the sequences from ANA ID NO 13, 9 and 5 from Example 2. However for this example no sequence or model information is utilised, other than for simulation of the initial dataset. Using the pairwise alignment scores as measures of similarity a tree is constructed by neighbour joining as is known in the art. As shown in FIGS. 23 and 24, these datasets cluster well into two and three populations respectively. It is also clear that a threshold could be defined (length of lines represents similarity) to separate these clusters.

Figure 25:
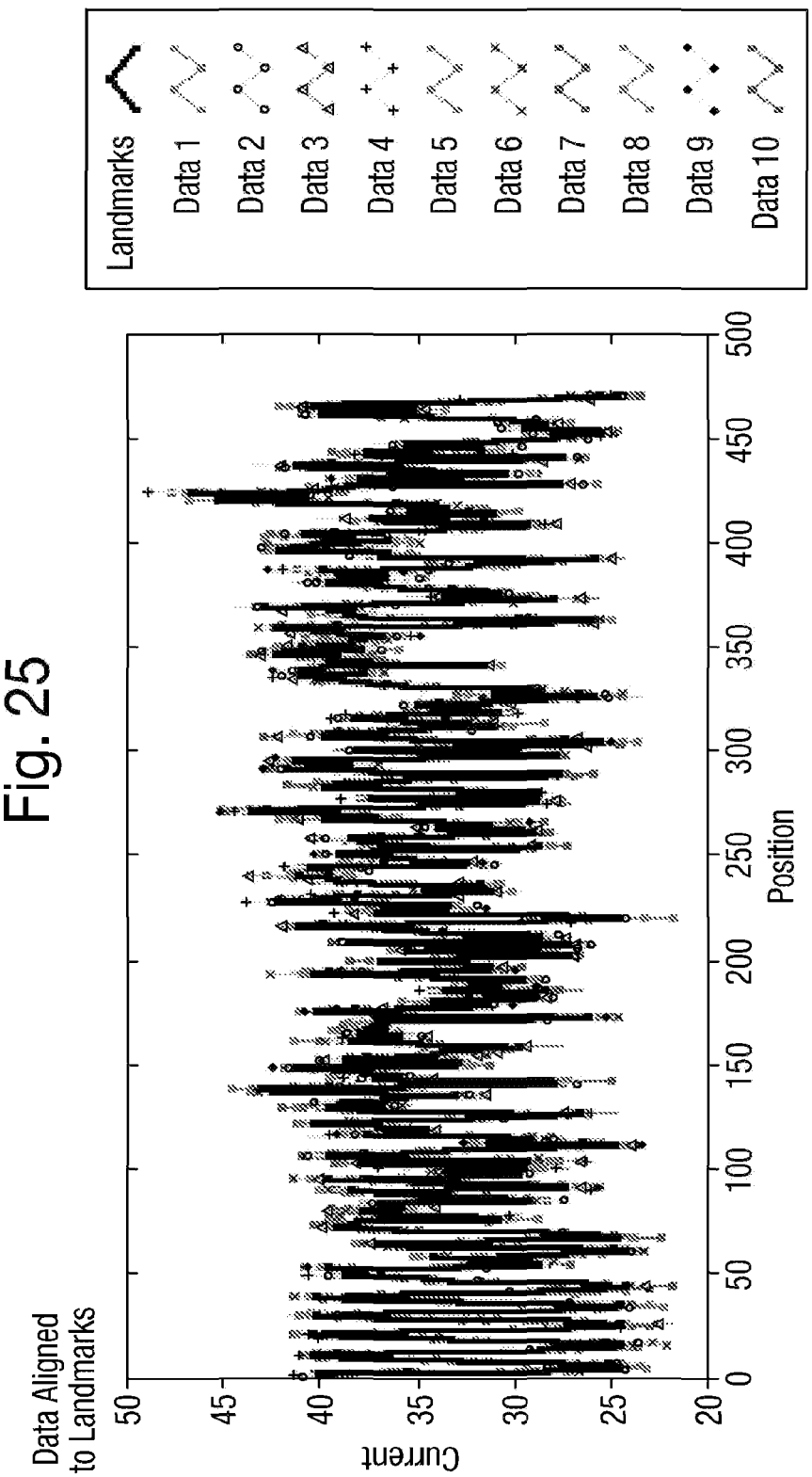
FIGS. 25 to 27 are graphs of landmark consensus with final alignment of data for each identified cluster in Example 5.
Figure 26:
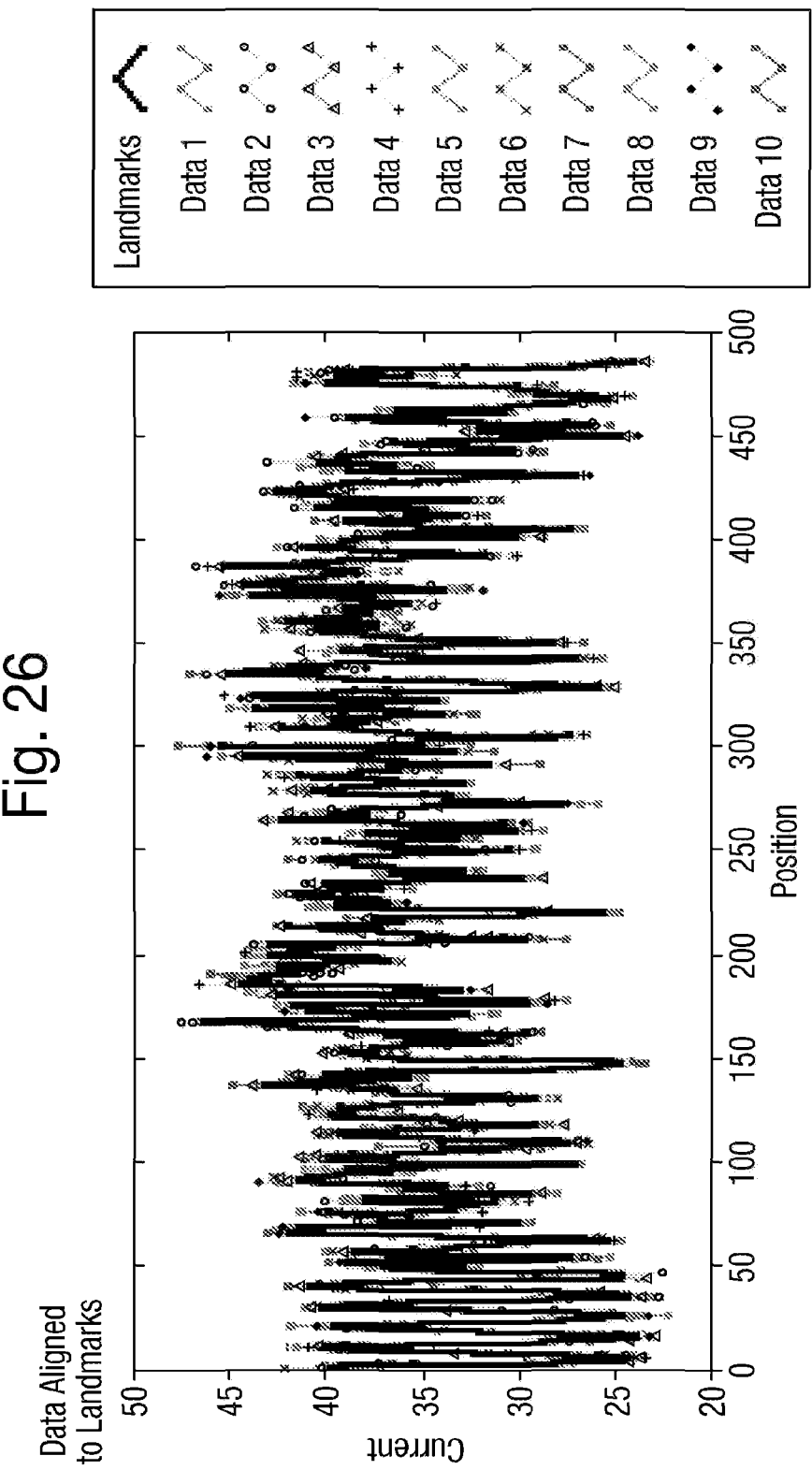
Figure 27:
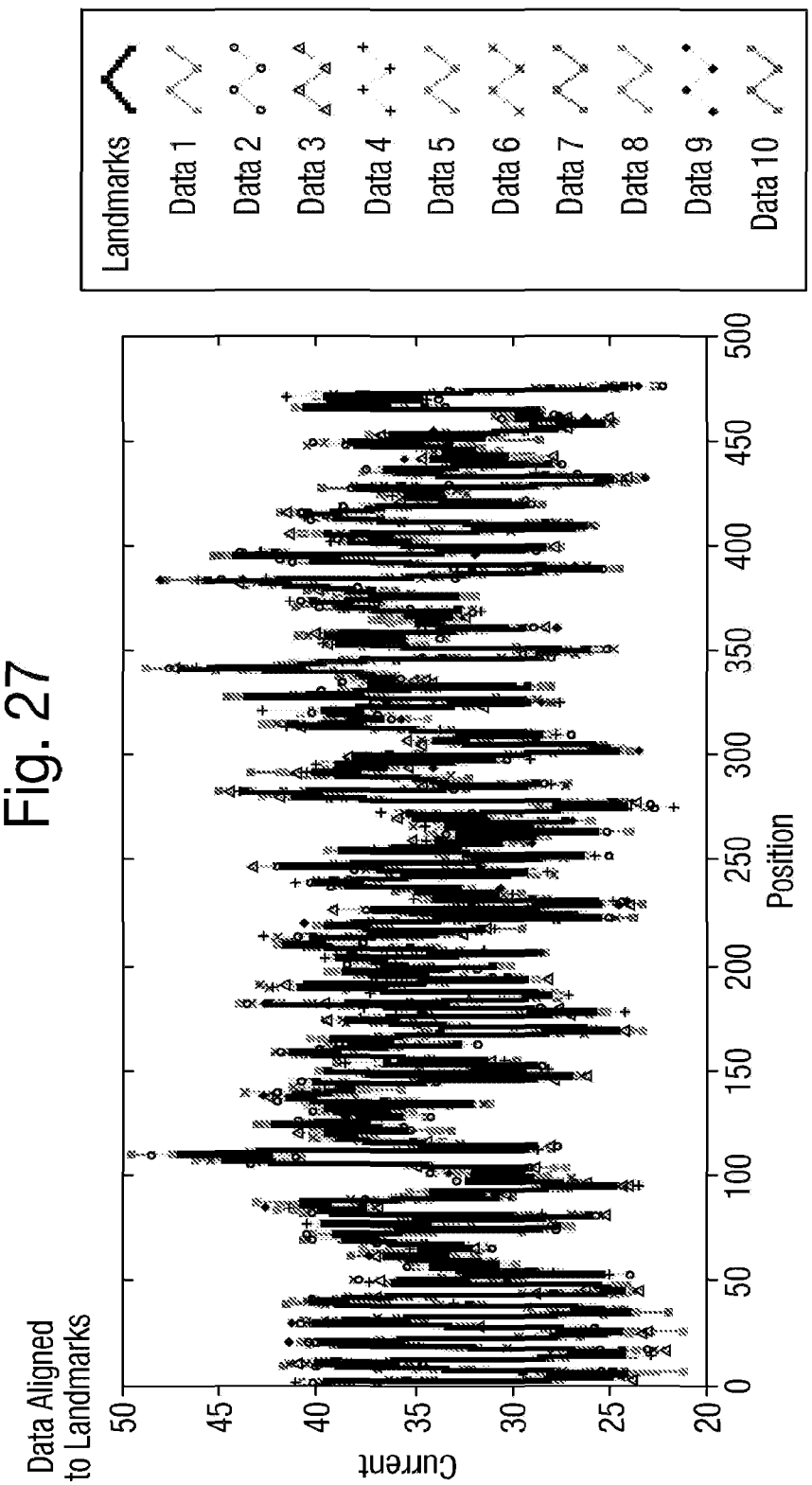

In the case of the three cluster experiment a landmark consensus for each cluster was built. The results of this are shown in FIGS. 25 to 27.

Figure 28:
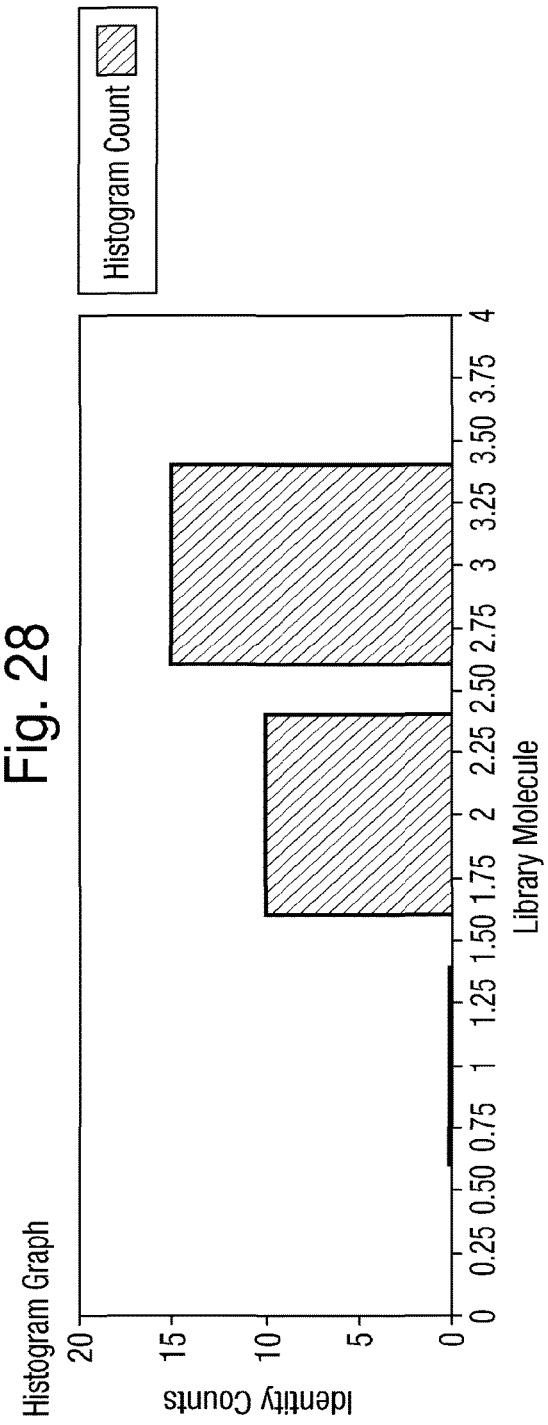
FIGS. 28 and 29 are histograms of classifications for the two cluster and three cluster experiment respectively in Example 5.
Figure 29:
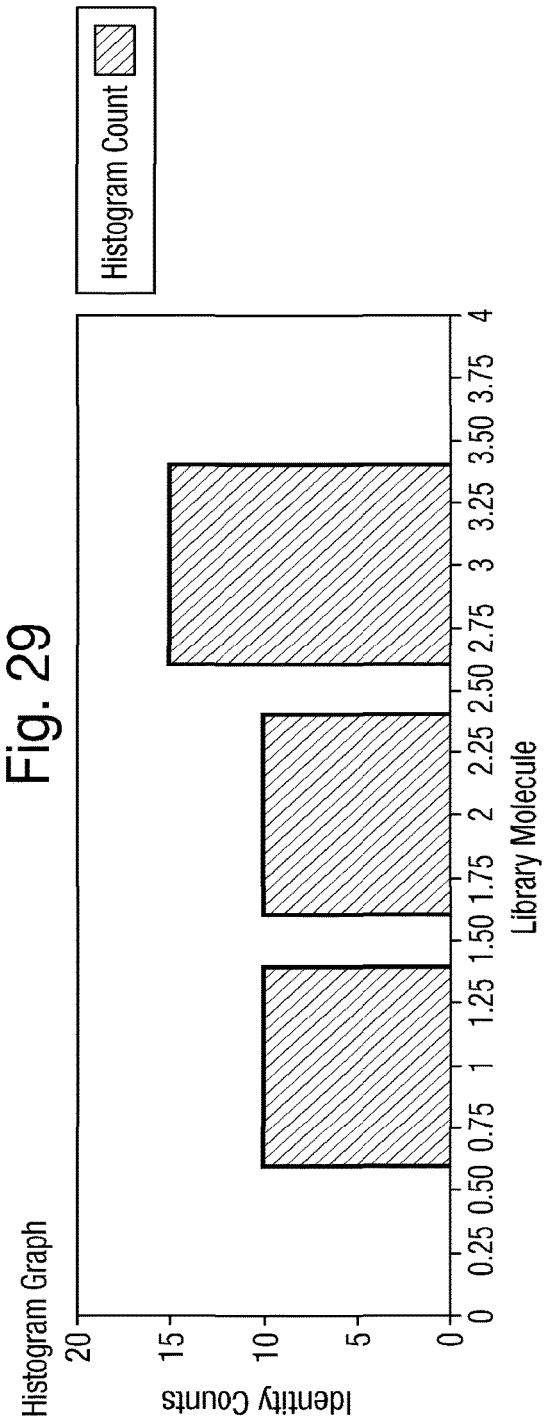

The identification as for Example 2 was run for both experiments. FIGS. 28 and 29 show the counts against the three clusters for the two cluster and three cluster experiment. We see we have correctly quantified the mixtures in each experiment.

Example 6 concerns assembly of a larger library feature vector from smaller feature vectors.

This example uses simulated data from the overlapping sequences S1-S18 as described above. However, to illustrate the assembly process we remove the sequences at the start and end, common to all sequences (as described in Example 2) such that the sequences overlap without any mis-matched regions (as was shown in FIG. 12). Since the sequences are guaranteed to be overlapping a relatively simple method can be used. Were this not the case one could use more complex assembly algorithms adapted from those known in the art as described above.

Figure 30:
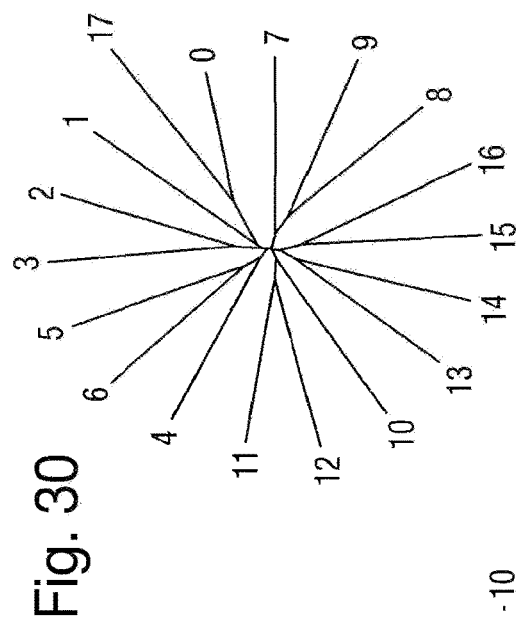
FIG. 30 is a diagram of a tree formed by neighbour joining on alignment similarity scores in Example 6 of the method.

A tree by neighbour joining on pairwise alignment scores was constructed, similar to Example 5. However since relatively large non-similar regions were expected, there was used a scoring function that does not penalise gaps at the beginning or end of the alignment as strongly as those within the alignment. The tree is shown in FIG. 30. Here it can be seen that all the sequences have similar relation to two other sequences, representing the ~100 base overlap each sequence shares with the sequences either side.

Figure 31:
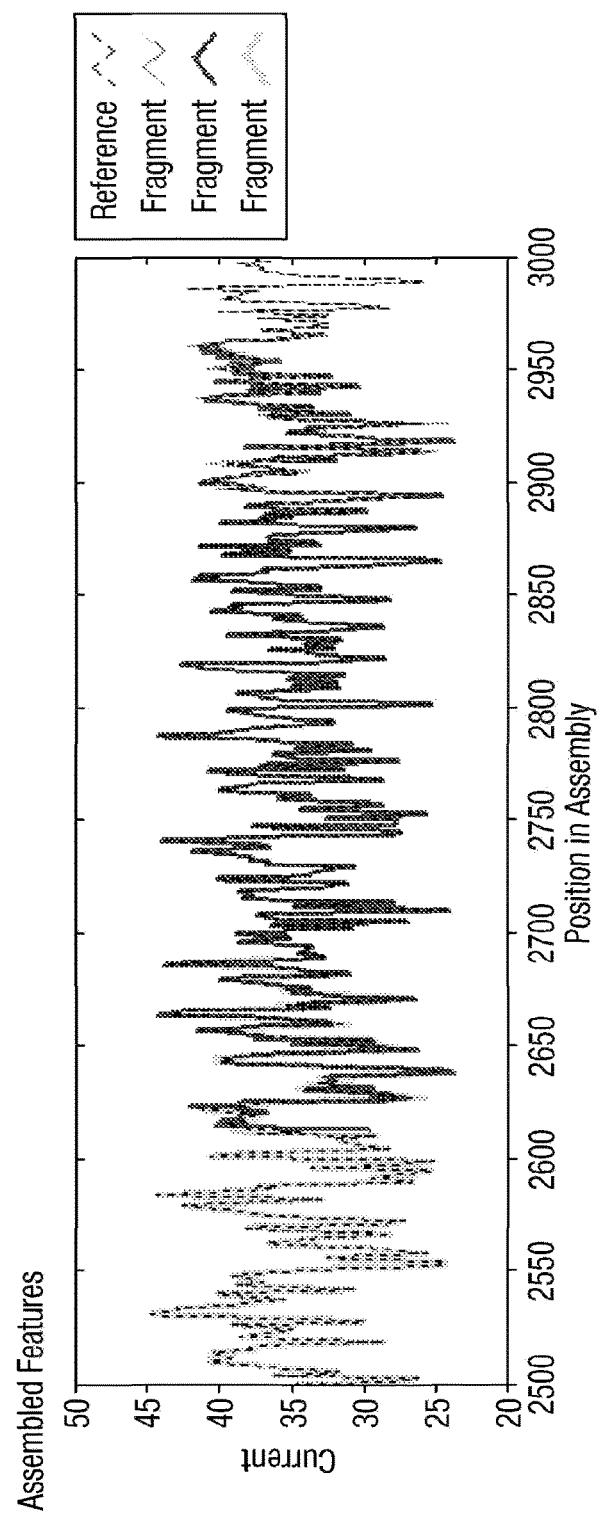
FIG. 31 is a graph of landmark consensus with final alignment of data for each of three fragments in Example 6.

Progressing through the tree in order of relatedness, consensus landmarks for the aligned sequences are constructed with the output landmarks from a pair of sequences acting as the feature vector where that pair is joined to another sequence. The output of the process is a fully assembled feature vector. The original data was aligned to the assembled features for illustration. Alignments for three fragments are shown in FIG. 31, wherein the overlaps can be clearly seen.

The invention claimed is:

1. A method of estimating an identity of a target polymer, the method comprising:
making electrical measurements of a polymer during translocation of the polymer through a nanopore to generate a time-ordered series of electrical measurements, wherein the polymer is a polynucleotide comprising at least 1,000 nucleotide pairs, wherein the translocation is controlled by an enzyme molecular motor and wherein each of the electrical measurements is an electrical measurement of respective k polymer units of the polymer, where k is 3 or greater;

deriving, from the time-ordered series of electrical measurements and using at least one processor, a feature vector of time-ordered features representing characteristics of the time-ordered series of electrical measurements, wherein the features comprise: an average of the electrical measurements, a period of the electrical measurements, a variance of the electrical measurements, asymmetry information, confidence information of the electrical measurements, and a distribution of the electrical measurements, wherein the feature vector comprises at least 1000 sets of time-ordered features;

analyzing, using the at least one processor, the feature vector that comprises the at least 1000 sets of time-ordered features and at least one other feature vector indicative of the target polymer by using an alignment algorithm or a machine learning algorithm; and estimating, using the at least one processor, the identity of the target polymer using results of analyzing the feature vector comprising the at least 1000 sets of time-ordered features and the at least one other feature vector indicative of the target polymer.

2. The method according to claim 1, wherein the at least one other feature vector is at least one other feature vector stored in a memory in respect of at least one class.

3. The method according to claim 2, further comprising selecting the at least one other feature vector stored in the memory based on the polymer.

4. The method according to claim 2, wherein the at least one other feature vector stored in the memory comprises an overall feature vector of a common polymer constructed from the feature vectors of fragments.

5. The method according to claim 2, wherein the analyzing comprises determining similarity between an entirety or part of the derived feature vector and an entirety of the at least one other feature vector stored in the memory.

6. The method according to claim 2, wherein the analyzing comprises determining similarity between an entirety or part of the derived feature vector between the derived feature vector and a part of the at least one other feature vector stored in the memory.

7. The method according to claim 2, further comprising classifying the polymer from which the derived feature vector is derived as belonging to a said class on a basis of the results of the analyzing.

8. The method according to claim 7, further comprising counting numbers of feature vectors belonging to different classes.

9. The method according to claim 7, further comprising identifying localized regions where the derived feature vector is dissimilar to a feature vector in respect of the class in which the polymer is classified as belonging.

10. The method according to claim 1, wherein the at least one other feature vector is a feature vector derived using a same method.

11. The method according to claim 10, wherein the at least one other feature vector is plural other feature vectors derived using the same method, and the method further comprises identifying features vectors that are derived from polymers that are fragments of a common polymer on basis of similarity in overlapping parts of the feature vectors.

12. The method according to claim 10, further comprising constructing an overall feature vector of a common polymer from feature vectors of identified fragments.

13. The method according to claim 10, wherein the at least one other feature vector is plural other feature vectors derived using the same method, and the method further comprises identifying clusters of similar feature vectors as a class and classifying the polymers from which the feature vectors are derived as belonging to an identified class.

14. The method according to claim 1, wherein the at least one other feature vector comprises a feature vector stored in a memory and the analyzing comprises determining localized regions where the feature vector is dissimilar to the at least one other feature vector stored in the memory.

15. The method according to claim 1, wherein groups of consecutive measurements are dependent on a respective k-mer that is different for each group, and deriving the feature vector comprises identifying groups of consecutive measurements, and, in respect of each group, deriving values of one or more features that represent characteristics of the measurements of the group.

16. The method according to claim 1, wherein the polymer units are nucleotides.

17. The method according to claim 1, wherein the nanopore is a biological pore.

18. The method according to claim 1, wherein said translocation of the polymer through the nanopore is performed in a ratcheted manner in which successive k-mers are registered with the nanopore.

19. The method according to claim 1, wherein the translocation of the polymer is controlled by a molecular ratchet that is a polymer binding protein.

20. At least one non-transitory computer readable medium storing instructions that, when executed by at least one processor, perform the method according to claim 1.

21. The method according to claim 1, wherein the machine learning algorithm utilizes a Hidden Markov Model (HMM).

22. The method of claim 1, wherein making the electrical measurements of the polymer during translocation of the polymer through the nanopore comprises generating the time-ordered series of measurements of the polymer during cis to trans translocation of the polymer through the nanopore.

23. An analysis device, comprising:
means to make electrical measurements of a polymer during translocation of a polymer through a nanopore to generate a time-ordered series of electrical measurements, wherein the polymer is a polynucleotide comprising at least 1,000 nucleotide pairs, wherein the translocation is controlled by an enzyme molecular motor and wherein each electrical measurement is an electrical measurement of respective k polymer units of the polymer, where k is 3 or greater;

means for deriving, from the time-ordered series of electrical measurements, a feature vector of time-ordered features representing characteristics of the time-ordered series of electrical measurements, wherein the features comprise: an average of the electrical measurements, a period of the electrical measurements, a variance of the electrical measurements, asymmetry information, confidence information of the electrical measurements, and a distribution of the electrical measurements, wherein the feature vector comprises at least 1000 sets of time-ordered features; and means for analyzing, using at least one processor, the feature vector that comprises the at least 1000 sets of time-ordered features and at least one other feature vector indicative of the target polymer by using an alignment algorithm or a machine learning algorithm;

means for estimating an identity of the target polymer using results of analyzing the feature vector comprising the at least 1000 sets of time-ordered features and the at least one other feature vector indicative of the target polymer.

24. A diagnostic device comprising:
an analysis device according to claim 23; and
a measurement system comprising a nanopore through which a polymer is capable of being translocated, the measurement system being arranged to make a continuous series of measurements of the polymer during translocation.

25. An analysis device, comprising:
a measurement system configured to make electrical measurements of a polymer during translocation of a polymer through a nanopore to generate a time-ordered series of electrical measurements, wherein the polymer is a polynucleotide comprising at least 1,000 nucleotide pairs, wherein the translocation is controlled by an enzyme molecular motor and wherein each of the electrical measurements is an electrical measurement of respective k polymer units of the polymer, where k is 3 or greater;

at least one processor configured to perform:
deriving, from the time-ordered series of electrical measurements, a feature vector of time-ordered features representing characteristics of the time-ordered series of electrical measurements, wherein the features comprise: an average of the electrical measurements, a period of the electrical measurements, a variance of the electrical measurements, asymmetry information, confidence information of the electrical measurements, and a distribution of the electrical measurements, wherein the feature vector comprises at least 1000 sets of time-ordered features;
analyzing the feature vector that comprises the at least 1000 sets of time-ordered features and at least one other feature vector indicative of a target polymer by using an alignment algorithm or a machine learning technique; and
estimating an identity of the target polymer using results of analyzing the feature vector comprising the at least 1000 sets of time-ordered features and the at least one other feature vector indicative of the target polymer.

* * * * *

```
                       SEQUENCE LISTING

<160> NUMBER OF SEQ ID NOS: 36

<210> SEQ ID NO 1
<211> LENGTH: 558
<212> TYPE: DNA
<213> ORGANISM: Artificial Sequence
<220> FEATURE:
<223> OTHER INFORMATION: MS-B1

<400> SEQUENCE: 1
atgggtctgg ataatgaact gagcctggtg gacggtcaag atcgtaccct gacggtgcaa        60
caatgggata cctttctgaa tggcgttttt ccgctggatc gtaatcgcct gacccgtgaa       120
tggtttcatt ccggtcgcgc aaaatatatc gtcgcaggcc cgggtgctga cgaattcgaa       180
ggcacgctgg aactgggtta tcagattggc tttccgtggt cactgggcgt tggtatcaac       240
ttctcgtaca ccacgccgaa tattctgatc aacaatggta acattaccgc accgccgttt       300
ggcctgaaca gcgtgattac gccgaacctg tttccggggtg ttagcatctc tgcccgtctg       360
ggcaatggtc cgggcattca agaagtggca acctttagtg tgcgcgtttc cggcgctaaa       420
ggcggtgtcg cggtgtctaa cgcccacggt accgttacgg gcgcggccgg cggtgtcctg       480
ctgcgtccgt tcgcgcgcct gattgcctct accggcgaca gcgttacgac ctatggcgaa       540
ccgtggaata tgaactaa                                                    558

<210> SEQ ID NO 2
<211> LENGTH: 184
<212> TYPE: PRT
<213> ORGANISM: Artificial Sequence
<220> FEATURE:
<223> OTHER INFORMATION: MS-B1

<400> SEQUENCE: 2

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60
```

-continued

```
Gly Tyr Gln Ile Gly Phe Pro Trp Ser Leu Gly Val Gly Ile Asn Phe
 65                  70                  75                  80

Ser Tyr Thr Thr Pro Asn Ile Leu Ile Asn Asn Gly Asn Ile Thr Ala
                 85                  90                  95

Pro Pro Phe Gly Leu Asn Ser Val Ile Thr Pro Asn Leu Phe Pro Gly
            100                 105                 110

Val Ser Ile Ser Ala Arg Leu Gly Asn Gly Pro Gly Ile Gln Glu Val
        115                 120                 125

Ala Thr Phe Ser Val Arg Val Ser Gly Ala Lys Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180
```

<210> SEQ ID NO 3
<211> LENGTH: 885
<212> TYPE: DNA
<213> ORGANISM: Artificial Sequence
<220> FEATURE:
<223> OTHER INFORMATION: alpha-HL-NN

<400> SEQUENCE: 3

```
atggcagatt ctgatattaa tattaaaacc ggtactacag atattggaag caatactaca      60
gtaaaaacag gtgatttagt cacttatgat aaagaaaatg gcatgcacaa aaaagtattt     120
tatagtttta tcgatgataa aaatcacaat aaaaaactgc tagttattag aacaaaaggt     180
accattgctg gtcaatatag agtttatagc gaagaaggtg ctaacaaaag tggtttagcc     240
tggccttcag cctttaaggt acagttgcaa ctacctgata tgaagtagc tcaaatatct      300
gattactatc caagaaattc gattgataca aaaaactata tgagtacttt aacttatgga     360
ttcaacggta atgttactgg tgatgataca ggaaaaattg gcggccttat tggtgcaaat     420
gtttcgattg tcatacact gaactatgtt caacctgatt tcaaaacaat tttagagagc      480
ccaactgata aaaagtagg ctggaaagtg atatttaaca atatggtgaa tcaaaattgg      540
ggaccatacg atcgagattc ttggaacccg tatatggca atcaactttt catgaaaact      600
agaaatggtt ctatgaaagc agcagataac ttccttgatc taacaaagc aagttctcta     660
ttatcttcag ggttttcacc agacttcgct acagttatta ctatggatag aaaagcatcc     720
aaacaacaaa caaatataga tgtaatatac gaacgagttc gtgatgatta ccaattgcat     780
tggacttcaa caaattggaa aggtaccaat actaaagata atggacaga tcgttcttca     840
gaaagatata aaatcgattg ggaaaaagaa gaaatgacaa attaa                     885
```

<210> SEQ ID NO 4
<211> LENGTH: 293
<212> TYPE: PRT
<213> ORGANISM: Artificial Sequence
<220> FEATURE:
<223> OTHER INFORMATION: alpha HL-NN

<400> SEQUENCE: 4

```
Ala Asp Ser Asp Ile Asn Ile Lys Thr Gly Thr Thr Asp Ile Gly Ser
  1               5                  10                  15

Asn Thr Thr Val Lys Thr Gly Asp Leu Val Thr Tyr Asp Lys Glu Asn
                 20                  25                  30
```

```
Gly Met His Lys Lys Val Phe Tyr Ser Phe Ile Asp Asp Lys Asn His
            35                  40                  45
Asn Lys Lys Leu Leu Val Ile Arg Thr Lys Gly Thr Ile Ala Gly Gln
 50                  55                  60
Tyr Arg Val Tyr Ser Glu Glu Gly Ala Asn Lys Ser Gly Leu Ala Trp
 65                  70                  75                  80
Pro Ser Ala Phe Lys Val Gln Leu Gln Leu Pro Asp Asn Glu Val Ala
                85                  90                  95
Gln Ile Ser Asp Tyr Tyr Pro Arg Asn Ser Ile Asp Thr Lys Asn Tyr
            100                 105                 110
Met Ser Thr Leu Thr Tyr Gly Phe Asn Gly Asn Val Thr Gly Asp Asp
            115                 120                 125
Thr Gly Lys Ile Gly Gly Leu Ile Gly Ala Asn Val Ser Ile Gly His
130                 135                 140
Thr Leu Asn Tyr Val Gln Pro Asp Phe Lys Thr Ile Leu Glu Ser Pro
145                 150                 155                 160
Thr Asp Lys Lys Val Gly Trp Lys Val Ile Phe Asn Asn Met Val Asn
                165                 170                 175
Gln Asn Trp Gly Pro Tyr Asp Arg Asp Ser Trp Asn Pro Val Tyr Gly
            180                 185                 190
Asn Gln Leu Phe Met Lys Thr Arg Asn Gly Ser Met Lys Ala Ala Asp
            195                 200                 205
Asn Phe Leu Asp Pro Asn Lys Ala Ser Ser Leu Leu Ser Ser Gly Phe
            210                 215                 220
Ser Pro Asp Phe Ala Thr Val Ile Thr Met Asp Arg Lys Ala Ser Lys
225                 230                 235                 240
Gln Gln Thr Asn Ile Asp Val Ile Tyr Glu Arg Val Arg Asp Asp Tyr
                245                 250                 255
Gln Leu His Trp Thr Ser Thr Asn Trp Lys Gly Thr Asn Thr Lys Asp
            260                 265                 270
Lys Trp Thr Asp Arg Ser Ser Glu Arg Tyr Lys Ile Asp Trp Glu Lys
            275                 280                 285
Glu Glu Met Thr Asn
            290

<210> SEQ ID NO 5
<211> LENGTH: 1830
<212> TYPE: DNA
<213> ORGANISM: Artificial Sequence
<220> FEATURE:
<223> OTHER INFORMATION: Phi29 DNA polymerase

<400> SEQUENCE: 5
atgaaacaca tgccgcgtaa aatgtatagc tgcgcgtttg aaaccacgac caaagtggaa        60
gattgtcgcg tttgggccta tggctacatg aacatcgaag atcattctga atacaaaatc       120
ggtaacagtc tggatgaatt tatggcatgg gtgctgaaag ttcaggcgga tctgtacttc       180
cacaacctga atttgatgg cgcattcatt atcaactggc tggaacgtaa tggctttaaa        240
tggagcgcgg atggtctgcc gaacacgtat aataccatta tctctcgtat gggccagtgg       300
tatatgattg atatctgcct gggctacaaa ggtaaacgca aaattcatac cgtgatctat       360
gatagcctga aaaactgccg gtttccggtg aagaaaattg cgaaagattt caaactgacg       420
gttctgaaag cgatattga ttatcacaaa gaacgtccgg ttggttacaa aatcaccccg       480
gaagaatacg catacatcaa aaacgatatc cagatcatcg cagaagcgct gctgattcag       540
```

-continued

```
tttaaacagg gcctggatcg catgaccgcg ggcagtgata gcctgaaagg tttcaaagat      600
atcatcacga ccaaaaaatt caaaaaagtg ttcccgacgc tgagcctggg tctggataaa      660
gaagttcgtt atgcctaccg cggcggtttt acctggctga cgatcgtttt caaagaaaaa      720
gaaattggcg agggtatggt gtttgatgtt aatagtctgt atccggcaca gatgtacagc      780
cgcctgctgc gtatggcga accgatcgtg ttcgaggta atatgtttg ggatgaagat        840
tacccgctgc atattcagca catccgttgt gaatttgaac tgaaagaagg ctatattccg      900
accattcaga tcaaacgtag tcgcttctat aagggtaacg aatacctgaa aagctctggc      960
ggtgaaatcg cggatctgtg gctgagtaac gtggatctgg aactgatgaa agaacactac     1020
gatctgtaca cgttgaata catcagcggc ctgaaattta agccacgac cggtctgttc      1080
aaagatttca tcgataaatg gacctacatc aaaacgacct ctgaaggcgc gattaaacag     1140
ctggccaaac tgatgctgaa cagcctgtat ggcaaattcg cctctaatcc ggatgtgacc     1200
ggtaaagttc cgtacctgaa agaaaatggc gcactgggtt ttcgcctggg cgaagaagaa     1260
acgaaagatc cggtgtatac cccgatgggt gttttcatta cggcctgggc acgttacacg     1320
accatcaccg cggcccaggc atgctatgat cgcattatct actgtgatac cgattctatt     1380
catctgacgg gcaccgaaat cccggatgtg attaaagata tcgttgatcc gaaaaaactg     1440
ggttattggg cccacgaaag tacgtttaaa cgtgcaaaat acctgcgcca gaaaacctac     1500
atccaggata tctacatgaa agaagtggat ggcaaactgg ttgaaggttc tccggatgat     1560
tacaccgata tcaaattcag tgtgaaatgc gccggcatga cggataaaat caaaaaagaa     1620
gtgaccttcg aaaacttcaa agttggttc agccgcaaaa tgaaaccgaa accggtgcag     1680
gttccgggcg gtgtggttct ggtggatgat acgtttacca ttaaatctgg cggtagtgcg     1740
tggagccatc cgcagttcga aaaggcggt ggctctggtg gcggttctgg cggtagtgcc     1800
tggagccacc cgcagtttga aaataataa                                       1830
```

<210> SEQ ID NO 6
<211> LENGTH: 608
<212> TYPE: PRT
<213> ORGANISM: Artificial Sequence
<220> FEATURE:
<223> OTHER INFORMATION: Phi29 DNA polymerase

<400> SEQUENCE: 6

```
Met Lys His Met Pro Arg Lys Met Tyr Ser Cys Ala Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125
```

```
Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
530                 535                 540

Asn Phe Lys Val Gly Phe Ser Arg Lys Met Lys Pro Lys Pro Val Gln
```

```
                545                 550                 555                 560
Val Pro Gly Gly Val Val Leu Val Asp Asp Thr Phe Thr Ile Lys Ser
                    565                 570                 575
Gly Gly Ser Ala Trp Ser His Pro Gln Phe Glu Lys Gly Gly Ser
                580                 585                 590
Gly Gly Ser Gly Gly Ser Ala Trp Ser His Pro Gln Phe Glu Lys
        595                 600                 605

<210> SEQ ID NO 7
<211> LENGTH: 1458
<212> TYPE: DNA
<213> ORGANISM: Escherichia coli
<220> FEATURE:
<221> NAME/KEY: misc_feature
<223> OTHER INFORMATION: EcoExo I

<400> SEQUENCE: 7
atgatgaacg atggcaaaca gcagagcacc ttcctgtttc atgattatga aaccttcggt      60
acccatccgg ccctggatcg tccggcgcag tttgcggcca ttcgcaccga tagcgaattc     120
aatgtgattg gcgaaccgga agtgttttat tgcaaaccgg ccgatgatta tctgccgcag     180
ccgggtgcgg tgctgattac cggtattacc ccgcaggaag cgcgcgcgaa aggtgaaaac     240
gaagcggcgt tgccgcgcg cattcatagc ctgtttaccg tgccgaaaac ctgcattctg     300
ggctataaca atgtgcgctt cgatgatgaa gttacccgta atatctttta tcgtaacttt     360
tatgatccgt atgcgtggag ctggcagcat gataacagcc gttgggatct gctggatgtg     420
atgcgcgcgt gctatgcgct cgcccggaa ggcattaatt ggccggaaaa cgatgatggc     480
ctgccgagct ttcgtctgga acatctgacc aaagccaacg gcattgaaca tagcaatgcc     540
catgatgcga tggccgatgt ttatgcgacc attgcgatgg cgaaactggt taaaacccgt     600
cagccgcgcc tgtttgatta tctgtttacc caccgtaaca acacaaaact gatggcgctg     660
attgatgttc gcagatgaa accgctggtg catgtgagcg gcatgtttgg cgcctggcgc     720
ggcaacacca gctgggtggc cccgctggcc tggcacccgg aaaatcgtaa cgccgtgatt     780
atggttgatc tggccggtga tattagcccg ctgctggaac tggatagcga tacccctgcgt     840
gaacgcctgt ataccgccaa aaccgatctg ggcgataatg ccgccgtgcc ggtgaaactg     900
gttcacatta caaatgccc ggtgctggcc caggcgaaca ccctgcgccc ggaagatgcg     960
gatcgtctgg gtattaatcg ccagcattgt ctggataatc tgaaaatcct gcgtgaaaac    1020
ccgcaggtgc gtgaaaaagt ggtggcgatc ttcgcggaag cggaaccgtt cacccccgagc    1080
gataacgtgg atgcgcagct gtataacggc ttctttagcg atgccgatcg cgcggcgatg    1140
aaaatcgttc tggaaaccga accgcgcaat ctgccggcgc tggatattac ctttgttgat    1200
aaacgtattg aaaaactgct gtttaattat cgtgcgcgca attttccggg taccctggat    1260
tatgccgaac agcagcgttg gctggaacat cgtcgtcagg ttttcacccc ggaatttctg    1320
cagggttatg cggatgaact gcagatgctg gttcagcagt atgccgatga taaagaaaaa    1380
gtggcgctgc tgaaagcgct gtggcagtat gcggaagaaa tcgtttctgg ctctggtcac    1440
catcatcatc accactaa                                                  1458

<210> SEQ ID NO 8
<211> LENGTH: 485
<212> TYPE: PRT
<213> ORGANISM: Escherichia coli
<220> FEATURE:
<221> NAME/KEY: MISC_FEATURE
```

<222> LOCATION: (1)..(485)
<223> OTHER INFORMATION: EcoExo I

<400> SEQUENCE: 8

```
Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Cys Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Cys Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Cys
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
        195                 200                 205

Phe Thr His Arg Asn Lys His Lys Leu Met Ala Leu Ile Asp Val Pro
    210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255

Asn Ala Val Ile Met Val Asp Leu Ala Gly Asp Ile Ser Pro Leu Leu
            260                 265                 270

Glu Leu Asp Ser Asp Thr Leu Arg Glu Arg Leu Tyr Thr Ala Lys Thr
        275                 280                 285

Asp Leu Gly Asp Asn Ala Ala Val Pro Val Lys Leu Val His Ile Asn
    290                 295                 300

Lys Cys Pro Val Leu Ala Gln Ala Asn Thr Leu Arg Pro Glu Asp Ala
305                 310                 315                 320

Asp Arg Leu Gly Ile Asn Arg Gln His Cys Leu Asp Asn Leu Lys Ile
                325                 330                 335

Leu Arg Glu Asn Pro Gln Val Arg Glu Lys Val Val Ala Ile Phe Ala
            340                 345                 350

Glu Ala Glu Pro Phe Thr Pro Ser Asp Asn Val Asp Ala Gln Leu Tyr
        355                 360                 365

Asn Gly Phe Phe Ser Asp Ala Asp Arg Ala Ala Met Lys Ile Val Leu
    370                 375                 380

Glu Thr Glu Pro Arg Asn Leu Pro Ala Leu Asp Ile Thr Phe Val Asp
385                 390                 395                 400
```

```
Lys Arg Ile Glu Lys Leu Leu Phe Asn Tyr Arg Ala Arg Asn Phe Pro
            405                 410                 415

Gly Thr Leu Asp Tyr Ala Glu Gln Gln Arg Trp Leu Glu His Arg Arg
        420                 425                 430

Gln Val Phe Thr Pro Glu Phe Leu Gln Gly Tyr Ala Asp Glu Leu Gln
    435                 440                 445

Met Leu Val Gln Gln Tyr Ala Asp Asp Lys Glu Lys Val Ala Leu Leu
450                 455                 460

Lys Ala Leu Trp Gln Tyr Ala Glu Glu Ile Val Ser Gly Ser Gly His
465                 470                 475                 480

His His His His His
            485

<210> SEQ ID NO 9
<211> LENGTH: 804
<212> TYPE: DNA
<213> ORGANISM: Escherichia coli
<220> FEATURE:
<221> NAME/KEY: misc_feature
<222> LOCATION: (1)..(804)
<223> OTHER INFORMATION: Exonuclease III

<400> SEQUENCE: 9
atgaaatttg ttagcttcaa tatcaacggc ctgcgcgcgc gcccgcatca gctggaagcg      60
attgtggaaa acatcagcc ggatgttatt ggtctgcagg aaaccaaagt tcacgatgat     120
atgtttccgc tggaagaagt ggcgaaactg gctataacg tgttttatca tggccagaaa      180
ggtcattatg gcgtggccct gctgaccaaa gaaaccccga tcgcggttcg tcgtggtttt      240
ccgggtgatg atgaagaagc gcagcgtcgt attattatgg cggaaattcc gagcctgctg      300
ggcaatgtga ccgttattaa cggctatttt ccgcagggcg aaagccgtga tcatccgatt      360
aaatttccgg ccaaagcgca gttctatcag aacctgcaga actatctgga aaccgaactg      420
aaacgtgata atccggtgct gatcatgggc gatatgaaca ttagcccgac cgatctggat      480
attggcattg gcgaagaaaa ccgtaaacgc tggctgcgta ccggtaaatg cagctttctg      540
ccggaagaac gtgaatggat ggatcgcctg atgagctggg gcctggtgga tacctttcgt      600
catgcgaacc gcagaccgc cgatcgcttt agctggtttg attatcgcag caaaggtttt      660
gatgataacc gtggcctgcg cattgatctg ctgctggcga ccagccgct ggcggaatgc      720 tgcgttgaaa ccggtattga ttatgaaatt cgcagcatgg aaaaaccgag cgatcacgcc      780
ccggtgtggg cgacctttcg ccgc                                              804

<210> SEQ ID NO 10
<211> LENGTH: 268
<212> TYPE: PRT
<213> ORGANISM: Escherichia coli
<220> FEATURE:
<221> NAME/KEY: MISC_FEATURE
<222> LOCATION: (1)..(268)
<223> OTHER INFORMATION: Exonuclease III

<400> SEQUENCE: 10

Met Lys Phe Val Ser Phe Asn Ile Asn Gly Leu Arg Ala Arg Pro His
1               5                   10                  15

Gln Leu Glu Ala Ile Val Glu Lys His Gln Pro Asp Val Ile Gly Leu
            20                  25                  30

Gln Glu Thr Lys Val His Asp Asp Met Phe Pro Leu Glu Glu Val Ala
        35                  40                  45
```

-continued

Lys Leu Gly Tyr Asn Val Phe Tyr His Gly Gln Lys Gly His Tyr Gly
        50                  55                  60

Val Ala Leu Leu Thr Lys Glu Thr Pro Ile Ala Val Arg Arg Gly Phe
 65                  70                  75                  80

Pro Gly Asp Asp Glu Glu Ala Gln Arg Arg Ile Ile Met Ala Glu Ile
                    85                  90                  95

Pro Ser Leu Leu Gly Asn Val Thr Val Ile Asn Gly Tyr Phe Pro Gln
                    100                 105                 110

Gly Glu Ser Arg Asp His Pro Ile Lys Phe Pro Ala Lys Ala Gln Phe
                    115                 120                 125

Tyr Gln Asn Leu Gln Asn Tyr Leu Glu Thr Glu Leu Lys Arg Asp Asn
            130                 135                 140

Pro Val Leu Ile Met Gly Asp Met Asn Ile Ser Pro Thr Asp Leu Asp
145                 150                 155                 160

Ile Gly Ile Gly Glu Glu Asn Arg Lys Arg Trp Leu Arg Thr Gly Lys
                    165                 170                 175

Cys Ser Phe Leu Pro Glu Glu Arg Glu Trp Met Asp Arg Leu Met Ser
                    180                 185                 190

Trp Gly Leu Val Asp Thr Phe Arg His Ala Asn Pro Gln Thr Ala Asp
            195                 200                 205

Arg Phe Ser Trp Phe Asp Tyr Arg Ser Lys Gly Phe Asp Asp Asn Arg
210                 215                 220

Gly Leu Arg Ile Asp Leu Leu Leu Ala Ser Gln Pro Leu Ala Glu Cys
225                 230                 235                 240

Cys Val Glu Thr Gly Ile Asp Tyr Glu Ile Arg Ser Met Glu Lys Pro
                    245                 250                 255

Ser Asp His Ala Pro Val Trp Ala Thr Phe Arg Arg
            260                 265

<210> SEQ ID NO 11
<211> LENGTH: 2000
<212> TYPE: DNA
<213> ORGANISM: Thermus thermophilus
<220> FEATURE:
<221> NAME/KEY: misc_feature
<222> LOCATION: (1)..(2000)
<223> OTHER INFORMATION: RecJ

<400> SEQUENCE: 11
atgcgtgatc gtgtccgctg gcgtgttctg tccctgccgc cgctggctca atggcgtgaa      60
gttatggctg ccctggaagt gggtccggaa gcggccctgg catattggca ccgcggtttt     120
cgtcgcaaag aagatctgga cccgccgctg gccctgctgc cgctgaaagg cctgcgcgaa     180
gcagctgcgc tgctggaaga agccctgcgt cagggtaaac gtattcgcgt tcatggcgat     240
tatgacgccg atggcctgac cgtaccgca attctggtcc gtggtctggc ggcactgggt      300
gccgatgtgc atccgtttat ccgcaccgc ctggaagaag ctacggtgt gctgatggaa      360 cgtgttccgg aacacctgga agcgagcgac ctgttcctga cggtggattg cggtatcacc     420
aaccatgccg aactgcgtga actgctggaa aatggcgttg aagtcattgt gaccgatcat     480 cacacccgg gtaaaacccc gtctccgggc ctggtggttc acccggcgct gacgccggat     540
ctgaaagaaa aaccgaccgg cgctggtgtc gtgtttctgc tgctgtgggc actgcacgaa     600
cgtctgggtc tgccgccgcc gctggaatat gccgacctgg ctgccgttgg taccattgcc     660
gatgttgccc cgctgtgggg ttggaaccgt gcactggtga agaaggcct ggcacgtatt     720

-continued

```
ccggctagct cttgggttgg tctgcgtctg ctggccgaag cagtcggcta caccggtaaa    780
gcggttgaag tcgccttccg tattgcaccg cgcatcaacg ccgcatcacg cctgggtgaa    840
gcagaaaaag ctctgcgtct gctgctgacg gatgacgctg cggaagctca ggcgctggtt    900
ggcgaactgc accgcctgaa tgctcgtcgc cagaccctgg aagaagcgat gctgcgtaaa    960
ctgctgccgc aagcggaccc ggaagccaaa gcaatcgtgc tgctggatcc ggaaggccat   1020
ccgggtgtta tgggcattgt cgcttcacgc atcctggaag cgacgctgcg tccggtcttt   1080
ctggtggcgc agggtaaagg taccgtgcgc agcctggcac cgatttctgc cgttgaagcc   1140
ctgcgtagcg ccgaagacct gctgctgcgt tatggcggtc acaaagaagc cgcaggcttt   1200
gctatggatg aagcgctgtt tccggcattc aaagctcgcg ttgaagccta cgctgcccgt   1260
ttcccggacc cggttcgtga agtcgcactg ctggatctgc tgccggaacc gggtctgctg   1320
ccgcaggtgt ttcgtgaact ggcgctgctg aaccgtatg gcgaaggtaa tccggaaccg   1380
ctgtttctgc tgtttggtgc accggaagaa gcacgtcgcc tgggtgaagg tcgtcacctg   1440
gcattccgcc tgaaaggtgt gcgtgttctg gcttggaaac agggtgatct ggccctgccg   1500
ccggaagttg aagtggcagg tctgctgtcc gaaaacgcat ggaatggcca tctggcctat   1560
gaagtgcaag cagttgatct gcgtaaaccg gaagcgctgg aaggcggtat tgccccgttt   1620
gcatatccgc tgccgctgct ggaagctctg gcccgtgccc gcctgggcga aggtgtttat   1680
gtcccggaag acaaccccgga aggtctggat tacgcacgca agctggctt ccgtctgctg   1740
ccgccggaag aagcgggtct gtggctgggt ctgccgccgc gcccggtgct gggtcgtcgc   1800
gtggaagttg cactgggccg tgaagcacgt gctcgcctga gtgcaccgcc ggttctgcat   1860
acccccggaag ctcgcctgaa agcgctggtg caccgtcgcc tgctgtttgc ctatgaacgt   1920
cgccatccgg gtctgttctc cgaagcgctg ctggcctact gggaagtcaa tcgtgttcag   1980
gaaccggcgg gtagtcctaa                                               2000
```

<210> SEQ ID NO 12
<211> LENGTH: 666
<212> TYPE: PRT
<213> ORGANISM: Thermus thermophilus
<220> FEATURE:
<221> NAME/KEY: MISC_FEATURE
<222> LOCATION: (1)..(666)
<223> OTHER INFORMATION: RecJ

<400> SEQUENCE: 12

```
Met Arg Asp Arg Val Arg Trp Arg Val Leu Ser Leu Pro Pro Leu Ala
1               5                   10                  15

Gln Trp Arg Glu Val Met Ala Ala Leu Glu Val Gly Pro Glu Ala Ala
            20                  25                  30

Leu Ala Tyr Trp His Arg Gly Phe Arg Arg Lys Glu Asp Leu Asp Pro
        35                  40                  45

Pro Leu Ala Leu Leu Pro Leu Lys Gly Leu Arg Glu Ala Ala Ala Leu
    50                  55                  60

Leu Glu Glu Ala Leu Arg Gln Gly Lys Arg Ile Arg Val His Gly Asp
65                  70                  75                  80

Tyr Asp Ala Asp Gly Leu Thr Gly Thr Ala Ile Leu Val Arg Gly Leu
                85                  90                  95

Ala Ala Leu Gly Ala Asp Val His Pro Phe Ile Pro His Arg Leu Glu
            100                 105                 110

Glu Gly Tyr Gly Val Leu Met Glu Arg Val Pro Glu His Leu Glu Ala
        115                 120                 125
```

```
Ser Asp Leu Phe Leu Thr Val Asp Cys Gly Ile Thr Asn His Ala Glu
    130                 135                 140
Leu Arg Glu Leu Leu Glu Asn Gly Val Glu Val Ile Val Thr Asp His
145                 150                 155                 160
His Thr Pro Gly Lys Thr Pro Ser Pro Gly Leu Val His Pro Ala
                165                 170                 175
Leu Thr Pro Asp Leu Lys Glu Lys Pro Thr Gly Ala Gly Val Val Phe
            180                 185                 190
Leu Leu Leu Trp Ala Leu His Glu Arg Leu Gly Leu Pro Pro Leu
        195                 200                 205
Glu Tyr Ala Asp Leu Ala Ala Val Gly Thr Ile Ala Asp Val Ala Pro
    210                 215                 220
Leu Trp Gly Trp Asn Arg Ala Leu Val Lys Glu Gly Leu Ala Arg Ile
225                 230                 235                 240
Pro Ala Ser Ser Trp Val Gly Leu Arg Leu Leu Ala Glu Ala Val Gly
                245                 250                 255
Tyr Thr Gly Lys Ala Val Glu Val Ala Phe Arg Ile Ala Pro Arg Ile
            260                 265                 270
Asn Ala Ala Ser Arg Leu Gly Glu Ala Glu Lys Ala Leu Arg Leu Leu
275                 280                 285
Leu Thr Asp Asp Ala Ala Glu Ala Gln Ala Leu Val Gly Glu Leu His
    290                 295                 300
Arg Leu Asn Ala Arg Arg Gln Thr Leu Glu Glu Ala Met Leu Arg Lys
305                 310                 315                 320
Leu Leu Pro Gln Ala Asp Pro Glu Ala Lys Ala Ile Val Leu Leu Asp
                325                 330                 335
Pro Glu Gly His Pro Gly Val Met Gly Ile Val Ala Ser Arg Ile Leu
            340                 345                 350
Glu Ala Thr Leu Arg Pro Val Phe Leu Val Ala Gln Gly Lys Gly Thr
                355                 360                 365
Val Arg Ser Leu Ala Pro Ile Ser Ala Val Glu Ala Leu Arg Ser Ala
370                 375                 380
Glu Asp Leu Leu Leu Arg Tyr Gly Gly His Lys Glu Ala Ala Gly Phe
385                 390                 395                 400
Ala Met Asp Glu Ala Leu Phe Pro Ala Phe Lys Ala Arg Val Glu Ala
                405                 410                 415
Tyr Ala Ala Arg Phe Pro Asp Pro Val Arg Glu Val Ala Leu Leu Asp
            420                 425                 430
Leu Leu Pro Glu Pro Gly Leu Leu Pro Gln Val Phe Arg Glu Leu Ala
        435                 440                 445
Leu Leu Glu Pro Tyr Gly Glu Gly Asn Pro Glu Pro Leu Phe Leu Leu
    450                 455                 460
Phe Gly Ala Pro Glu Glu Ala Arg Arg Leu Gly Glu Gly Arg His Leu
465                 470                 475                 480
Ala Phe Arg Leu Lys Gly Val Arg Val Leu Ala Trp Lys Gln Gly Asp
                485                 490                 495
Leu Ala Leu Pro Pro Glu Val Glu Val Ala Gly Leu Leu Ser Glu Asn
            500                 505                 510
Ala Trp Asn Gly His Leu Ala Tyr Glu Val Gln Ala Val Asp Leu Arg
        515                 520                 525
Lys Pro Glu Ala Leu Glu Gly Gly Ile Ala Pro Phe Ala Tyr Pro Leu
    530                 535                 540
```

-continued

Pro Leu Leu Glu Ala Leu Ala Arg Ala Arg Leu Gly Glu Gly Val Tyr
545                 550                 555                 560

Val Pro Glu Asp Asn Pro Glu Gly Leu Asp Tyr Ala Arg Lys Ala Gly
                565                 570                 575

Phe Arg Leu Leu Pro Pro Glu Glu Ala Gly Leu Trp Leu Gly Leu Pro
            580                 585                 590

Pro Arg Pro Val Leu Gly Arg Arg Val Glu Val Ala Leu Gly Arg Glu
        595                 600                 605

Ala Arg Ala Arg Leu Ser Ala Pro Pro Val Leu His Thr Pro Glu Ala
    610                 615                 620

Arg Leu Lys Ala Leu Val His Arg Arg Leu Leu Phe Ala Tyr Glu Arg
625                 630                 635                 640

Arg His Pro Gly Leu Phe Ser Glu Ala Leu Leu Ala Tyr Trp Glu Val
                645                 650                 655

Asn Arg Val Gln Glu Pro Ala Gly Ser Pro
            660                 665

<210> SEQ ID NO 13
<211> LENGTH: 681
<212> TYPE: DNA
<213> ORGANISM: Artificial Sequence
<220> FEATURE:
<223> OTHER INFORMATION: Lambda Exonuclease

<400> SEQUENCE: 13
atgacaccgg acattatcct gcagcgtacc gggatcgatg tgagagctgt cgaacagggg      60
gatgatgcgt ggcacaaatt acggctcggc gtcatcaccg cttcagaagt tcacaacgtg     120
atagcaaaac cccgctccgg aaagaagtgg cctgacatga aaatgtccta cttccacacc     180
ctgcttgctg aggtttgcac cggtgtggct ccggaagtta acgctaaagc actggcctgg     240
ggaaaacagt acgagaacga cgccagaacc ctgtttgaat tcacttccgg cgtgaatgtt     300
actgaatccc cgatcatcta tcgcgacgaa agtatgcgta ccgcctgctc tcccgatggt     360
ttatgcagtg acggcaacgg ccttgaactg aaatgcccgt ttacctcccg ggatttcatg     420
aagttccggc tcggtggttt cgaggccata aagtcagctt acatggccca ggtgcagtac     480
agcatgtggg tgacgcgaaa aaatgcctgg tactttgcca actatgaccc gcgtatgaag     540
cgtgaaggcc tgcattatgt cgtgattgag cgggatgaaa agtacatggc gagttttgac     600
gagatcgtgc cggagttcat cgaaaaaatg gacgaggcac tggctgaaat tggttttgta     660
tttggggagc aatggcgata a                                               681

<210> SEQ ID NO 14
<211> LENGTH: 226
<212> TYPE: PRT
<213> ORGANISM: Artificial Sequence
<220> FEATURE:
<223> OTHER INFORMATION: Lambda Exonuclease

<400> SEQUENCE: 14

Met Thr Pro Asp Ile Ile Leu Gln Arg Thr Gly Ile Asp Val Arg Ala
1               5                   10                  15

Val Glu Gln Gly Asp Asp Ala Trp His Lys Leu Arg Leu Gly Val Ile
            20                  25                  30

Thr Ala Ser Glu Val His Asn Val Ile Ala Lys Pro Arg Ser Gly Lys
        35                  40                  45

Lys Trp Pro Asp Met Lys Met Ser Tyr Phe His Thr Leu Leu Ala Glu
    50                  55                  60

```
Val Cys Thr Gly Val Ala Pro Glu Val Asn Ala Lys Ala Leu Ala Trp
 65                  70                  75                  80

Gly Lys Gln Tyr Glu Asn Asp Ala Arg Thr Leu Phe Glu Phe Thr Ser
                 85                  90                  95

Gly Val Asn Val Thr Glu Ser Pro Ile Ile Tyr Arg Asp Glu Ser Met
            100                 105                 110

Arg Thr Ala Cys Ser Pro Asp Gly Leu Cys Ser Asp Gly Asn Gly Leu
            115                 120                 125

Glu Leu Lys Cys Pro Phe Thr Ser Arg Asp Phe Met Lys Phe Arg Leu
130                 135                 140

Gly Gly Phe Glu Ala Ile Lys Ser Ala Tyr Met Ala Gln Val Gln Tyr
145                 150                 155                 160

Ser Met Trp Val Thr Arg Lys Asn Ala Trp Tyr Phe Ala Asn Tyr Asp
                165                 170                 175

Pro Arg Met Lys Arg Glu Gly Leu His Tyr Val Val Ile Glu Arg Asp
            180                 185                 190

Glu Lys Tyr Met Ala Ser Phe Asp Glu Ile Val Pro Glu Phe Ile Glu
            195                 200                 205

Lys Met Asp Glu Ala Leu Ala Glu Ile Gly Phe Val Phe Gly Glu Gln
210                 215                 220

Trp Arg
225

<210> SEQ ID NO 15
<211> LENGTH: 184
<212> TYPE: PRT
<213> ORGANISM: Artificial Sequence
<220> FEATURE:
<223> OTHER INFORMATION: MspB

<400> SEQUENCE: 15

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Asp Leu Gly Asn Gly Pro Gly Ile Gln Glu Val
            115                 120                 125

Ala Thr Phe Ser Val Asp Val Ser Gly Pro Ala Gly Gly Val Ala Val
130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180
```

```
<210> SEQ ID NO 16
<211> LENGTH: 184
<212> TYPE: PRT
<213> ORGANISM: Artificial Sequence
<220> FEATURE:
<223> OTHER INFORMATION: MspC

<400> SEQUENCE: 16

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Gly
                85                  90                  95

Pro Pro Phe Gly Leu Glu Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 17
<211> LENGTH: 183
<212> TYPE: PRT
<213> ORGANISM: Artificial Sequence
<220> FEATURE:
<223> OTHER INFORMATION: MspD

<400> SEQUENCE: 17

Val Asp Asn Gln Leu Ser Val Val Asp Gly Gln Gly Arg Thr Leu Thr
1               5                   10                  15

Val Gln Gln Ala Glu Thr Phe Leu Asn Gly Val Phe Pro Leu Asp Arg
            20                  25                  30

Asn Arg Leu Thr Arg Glu Trp Phe His Ser Gly Arg Ala Thr Tyr His
        35                  40                  45

Val Ala Gly Pro Gly Ala Asp Glu Phe Glu Gly Thr Leu Glu Leu Gly
    50                  55                  60

Tyr Gln Val Gly Phe Pro Trp Ser Leu Gly Val Gly Ile Asn Phe Ser
65                  70                  75                  80

Tyr Thr Thr Pro Asn Ile Leu Ile Asp Gly Gly Asp Ile Thr Gln Pro
                85                  90                  95

Pro Phe Gly Leu Asp Thr Ile Ile Thr Pro Asn Leu Phe Pro Gly Val
            100                 105                 110

Ser Ile Ser Ala Asp Leu Gly Asn Gly Pro Gly Ile Gln Glu Val Ala
```

```
            115                 120                 125
Thr Phe Ser Val Asp Val Lys Gly Ala Lys Gly Ala Val Ala Val Ser
    130                 135                 140

Asn Ala His Gly Thr Val Thr Gly Ala Ala Gly Gly Val Leu Leu Arg
145                 150                 155                 160

Pro Phe Ala Arg Leu Ile Ala Ser Thr Gly Asp Ser Val Thr Thr Tyr
                165                 170                 175

Gly Glu Pro Trp Asn Met Asn
            180
```

<210> SEQ ID NO 18
<211> LENGTH: 482
<212> TYPE: DNA
<213> ORGANISM: Artificial Sequence
<220> FEATURE:
<223> OTHER INFORMATION: ANA ID NO: 1 (PhiX Fragment Sense 1)

<400> SEQUENCE: 18

```
ttttgccat cagattgtgt tgttagtcg ctggttgttt ctgttggtgc tgatattgct    60
tttgatgccg accctaaatt ttttgcctgt ttggttcgct ttgagtcttc ttcggttccg   120
actaccctcc cgactgccta tgatgttat cctttggatg tcgccatga tggtggttat   180
tataccgtca aggactgtgt gactattgac gtccttcccc gtacgccggg caataatgtt   240
tatgttggtt tcatggtttg gtctaacttt accgctacta atgccgcgg attggtttcg   300
ctgaatcagg ttattaaaga gattatttgt ctccagccac ttaagtgagg tgatttatgt   360
ttggtgctat tgctggcggt attgcttctg ctcttgctgg tggcgccatg tctaaattgt   420
ttggaggcgg tctttttccc cctttttccc cctttttccc ccttttttccc cctttttccc   480
cc                                                                   482
```

<210> SEQ ID NO 19
<211> LENGTH: 486
<212> TYPE: DNA
<213> ORGANISM: Artificial Sequence
<220> FEATURE:
<223> OTHER INFORMATION: ANA ID NO: 2 (PhiX Fragment Sense 2)

<400> SEQUENCE: 19

```
ttttgccat cagattgtgt tgttagtcg ctgtctccag ccacttaagt gaggtgattt    60
atgtttggtg ctattgctgg cggtattgct tctgctcttg ctggtggcgc catgtctaaa   120
ttgtttggag gcggtcaaaa agccgcctcc ggtggcattc aaggtgatgt gcttgctacc   180
gataacaata ctgtaggcat gggtgatgct ggtattaaat ctgccattca aggctctaat   240
gttcctaacc ctgatgaggc cgtccctagt tttgttctg gtgctatggc taaagctggt   300
aaaggactt ttgaaggtac gttgcaggct ggcacttctg ccgtttctga taagttgctt   360
gatttggttg gacttggtgg caagtctgcc gctgataaag gaaaggatac tcgtgattat   420
cttgctgctg catttctttt tccccctttt tccccctttt tccccctttt tccccctttt   480
tccccc                                                             486
```

<210> SEQ ID NO 20
<211> LENGTH: 481
<212> TYPE: DNA
<213> ORGANISM: Artificial Sequence
<220> FEATURE:
<223> OTHER INFORMATION: ANA ID NO: 3 (PhiX Fragment Sense 3)

<400> SEQUENCE: 20

```
tttttgccat cagattgtgt tgttagtcg ctctgccgtt tctgataagt tgcttgattt    60
ggttggactt ggtggcaagt ctgccgctga taaaggaaag gatactcgtg attatcttgc   120
tgctgcattt cctgagctta atgcttggga gcgtgctggt gctgatgctt cctctgctgg   180
tatggttgac gccggatttg agaatcaaaa agagcttact aaaatgcaac tggacaatca   240
gaaagagatt gccgagatgc aaaatgagac tcaaaaagag attgctggca ttcagtcggc   300
gacttcacgc cagaatacga agaccaggt atatgcacaa aatgagatgc ttgcttatca    360
acagaaggag tctactgctc gcgttgcgtc tattatggaa aacaccaatc tttccaagca   420
acagcaggtt tttttccccc cttttttccc ctttttcccc cttttttccc cttttttccc   480
c                                                                  481

<210> SEQ ID NO 21
<211> LENGTH: 482
<212> TYPE: DNA
<213> ORGANISM: Artificial Sequence
<220> FEATURE:
<223> OTHER INFORMATION: ANA ID NO: 4 (PhiX Fragment Sense 4)

<400> SEQUENCE: 21
tttttgccat cagattgtgt tgttagtcg cttatgcaca aaatgagatg cttgcttatc    60
aacagaagga gtctactgct cgcgttgcgt ctattatgga aaacaccaat ctttccaagc   120
aacagcaggt ttccgagatt atgcgccaaa tgcttactca agctcaaacg ctggtcagt   180 attttaccaa tgaccaaatc aaagaaatga ctcgcaaggt tagtgctgag gttgacttag   240
ttcatcagca aacgcagaat cagcggtatg gctcttctca tattggcgct actgcaaagg   300
atatttctaa tgtcgtcact gatgctgctt ctggtgtggt tgatatttt catggtattg    360 ataaagctgt tgccgatact tggaacaatt tctggaaaga cggtaaagct gatggtattg   420
gctctaattt gttttttccc ctttttccc cttttttccc cttttttccc ctttttccc   480 cc                                                                 482

<210> SEQ ID NO 22
<211> LENGTH: 482
<212> TYPE: DNA
<213> ORGANISM: Artificial Sequence
<220> FEATURE:
<223> OTHER INFORMATION: ANA ID NO: 5 (PhiX Fragment Sense 5)

<400> SEQUENCE: 22
tttttgccat cagattgtgt tgttagtcg ctggtgtggt tgatatttt catggtattg     60 ataaagctgt tgccgatact tggaacaatt tctggaaaga cggtaaagct gatggtattg   120
gctctaattt gtctaggaaa taaccgtcag gattgacacc ctcccaattg tatgttttca   180
tgcctccaaa tcttggaggc ttttttatgg ttcgttctta ttacccttct gaatgtcacg   240
ctgattattt tgactttgag cgtatcgagg ctcttaaacc tgctattgag gcttgtggca   300
tttctactct ttctcaatcc ccaatgcttg gcttccataa gcagatggat aaccgcatca   360
agctcttgga agagattctg tcttttcgta tgcagggcgt tgagttcgat aatggtgata   420
tgtatgttga cgttttccc cttttttccc ctttttccc cttttttccc ctttttccc    480 cc                                                                 482

<210> SEQ ID NO 23
<211> LENGTH: 480
<212> TYPE: DNA
```

<213> ORGANISM: Artificial Sequence
<220> FEATURE:
<223> OTHER INFORMATION: ANA ID NO: 6 (PhiX Fragment Sense 6)

<400> SEQUENCE: 23

```
tttttgccat cagattgtgt tgttagtcg ctccataagc agatggataa ccgcatcaag      60
ctcttggaag agattctgtc ttttcgtatg cagggcgttg agttcgataa tggtgatatg    120
tatgttgacg gccataaggc tgcttctgac gttcgtgatg agtttgtatc tgttactgag    180
aagttaatgg atgaattggc acaatgctac aatgtgctcc cccaacttga tattaataac    240
actatagacc accgcccga aggggacgaa aaatggtttt tagagaacga gaagacggtt    300
acgcagtttt gccgcaagct ggctgctgaa cgccctctta aggatattcg cgatgagtat    360
aattacccca aaagaaagg tattaaggat gagtgttcaa gattgctgga ggcctccact    420
atgaaatcgc ttttccccc ttttccccc ttttccccc ttttccccc                  480
```

<210> SEQ ID NO 24
<211> LENGTH: 482
<212> TYPE: DNA
<213> ORGANISM: Artificial Sequence
<220> FEATURE:
<223> OTHER INFORMATION: ANA ID NO: 7 (PhiX Fragment Sense 7)

<400> SEQUENCE: 24

```
tttttgccat cagattgtgt tgttagtcg ctcgccctct aaggatatt cgcgatgagt      60
ataattaccc caaaagaaa ggtattaagg atgagtgttc aagattgctg gaggcctcca    120
ctatgaaatc gcgtagaggc tttgctattc agcgtttgat gaatgcaatg cgacaggctc    180
atgctgatgg ttggtttatc gttttgaca ctctcacgtt ggctgacgac cgattagagg    240
cgttttatga taatcccaat gctttgcgtg actatttcg tgatattggt cgtatggttc    300
ttgctgccga gggtcgcaag gctaatgatt cacacgccga ctgctatcag tattttgtg    360
tgcctgagta tggtacagct aatggccgtc ttcatttcca tgcggtgcac tttatgcgga    420
cacttcctac agttttccc cttttcccc cttttcccc cttttcccc cttttcccc        480
cc                                                                   482
```

<210> SEQ ID NO 25
<211> LENGTH: 482
<212> TYPE: DNA
<213> ORGANISM: Artificial Sequence
<220> FEATURE:
<223> OTHER INFORMATION: ANA ID NO: 8 (PhiX Fragment Sense 8)

<400> SEQUENCE: 25

```
tttttgccat cagattgtgt tgttagtcg ctcacgccga ctgctatcag tattttgtg      60
tgcctgagta tggtacagct aatggccgtc ttcatttcca tgcggtgcac tttatgcgga    120
cacttcctac aggtagcgtt gaccctaatt tggtcgtcg ggtacgcaat cgccgccagt    180
taaatagctt gcaaaatacg tggccttatg gttacagtat gcccatcgca gttcgctaca    240
cgcaggacgc ttttcacgt tctggttggt tgtggcctgt tgatgctaaa ggtgagccgc    300
ttaaagctac cagttatatg gctgttggtt tctatgtggc taaatacgtt aacaaaaagt    360
cagatatgga ccttgctgct aaaggtctag agctaaaga atggaacaac tcactaaaaa    420
ccaagctgtc gcttttccc ccttttccc ccttttccc ccttttccc ccttttccc        480
cc                                                                   482
```

<210> SEQ ID NO 26
<211> LENGTH: 491
<212> TYPE: DNA
<213> ORGANISM: Artificial Sequence
<220> FEATURE:
<223> OTHER INFORMATION: ANA ID NO: 9 (PhiX Fragment Sense 9)

<400> SEQUENCE: 26

```
tttttgccat cagattgtgt tgttagtcg ctgttggttt ctatgtggct aaatacgtta      60
acaaaaagtc agatatggac cttgctgcta aggtctagg agctaaagaa tggaacaact    120
cactaaaaac caagctgtcg ctacttccca agaagctgtt cagaatcaga atgagccgca    180
acttcgggat gaaaatgctc acaatgacaa atctgtccac ggagtgctta atccaactta    240
ccaagctggg ttacgacgcg acgccgttca accagatatt gaagcagaac gcaaaaagag    300
agatgagatt gaggctggga aaagttactg tagccgacgt tttggcggcg caacctgtga    360
cgacaaatct gctcaaattt atgcgcgctt cgataaaaat gattggcgta tccaacctgc    420
agagttttat cgcttccatg attttttccccc cttttttcccc cttttttcccc cttttttcccc    480
ctttttcccc c                                                           491
```

<210> SEQ ID NO 27
<211> LENGTH: 498
<212> TYPE: DNA
<213> ORGANISM: Artificial Sequence
<220> FEATURE:
<223> OTHER INFORMATION: ANA ID NO: 10 (PhiX Fragment Sense 10)

<400> SEQUENCE: 27

```
tttttgccat cagattgtgt tgttagtcg ctctgtagcc gacgttttgg cggcgcaacc      60
tgtgacgaca atctgctcca aatttatgcg cgcttcgata aaaatgattg gcgtatccaa    120
cctgcagagt tttatcgctt ccatgacgca gaagttaaca ctttcggata tttctgatga    180
gtcgaaaaat tatcttgata aagcaggaat tactactgct tgtttacgaa ttaaatcgaa    240
gtggactgct ggcggaaaat gagaaaattc gacctatcct tgcgcagctc gagaagctct    300
tactttgcga cctttcgcca tcaactaacg attctgtcaa aaactgacgc gttggatgag    360
gagaagtggc ttaatatgct tggcacgttc gtcaaggact ggtttagata tgagtcacat    420
tttgttcatg gtagagattc tcttgttgtt tttccccctt tttcccccctt tttcccccctt    480
tttcccccctt tttcccccc                                                  498
```

<210> SEQ ID NO 28
<211> LENGTH: 482
<212> TYPE: DNA
<213> ORGANISM: Artificial Sequence
<220> FEATURE:
<223> OTHER INFORMATION: ANA ID NO: 11 (PhiX Fragment Sense 11)

<400> SEQUENCE: 28

```
tttttgccat cagattgtgt tgttagtcg ctacgcgttg gatgaggaga agtggcttaa      60
tatgcttggc acgttcgtca aggactggtt tagatatgag tcacattttg ttcatggtag    120
agattctctt gttgacattt taaaagagcg tggattacta tctgagtccg atgctgttca    180
accactaata ggtaagaaat catgagtcaa gttactgaac aatccgtacg tttccagacc    240
gctttggcct ctattaagct cattcaggct tctgccgttt tggatttaac cgaagatgat    300
ttcgattttc tgacgagtaa caaagtttgg attgctactg accgctctcg tgctcgtcgc    360
tgcgttgagg cttgcgttta tggtacgctg gactttgtag gataccctcg ctttcctgct    420
```

```
cctgttgagt tttttttccc ccttttttccc ccttttttccc ccttttttccc ccttttttccc    480
cc                                                                      482

<210> SEQ ID NO 29
<211> LENGTH: 482
<212> TYPE: DNA
<213> ORGANISM: Artificial Sequence
<220> FEATURE:
<223> OTHER INFORMATION: ANA ID NO: 12 (PhiX Fragment Sense 12)

<400> SEQUENCE: 29
tttttgccat cagattgtgt tgttagtcg cttgctactg accgctctcg tgctcgtcgc         60
tgcgttgagg cttgcgttta tggtacgctg gactttgtag gataccctcg ctttcctgct      120
cctgttgagt ttattgctgc cgtcattgct tattatgttc atcccgtcaa cattcaaacg      180
gcctgtctca tcatggaagg cgctgaattt acggaaaaca ttattaatgg cgtcgagcgt      240
ccggttaaag ccgctgaatt gttcgcgttt accttgcgtg tacgcgcagg aaacactgac      300
gttcttactg acgcagaaga aaacgtgcgt caaaaattac gtgcagaagg agtgatgtaa      360
tgtctaaagg taaaaaacgt tctggcgctc gccctggtcg tccgcagccg ttgcgaggta      420
ctaaaggcaa gcttttttccc ccttttttccc ccttttttccc ccttttttccc ccttttttccc      480 cc                                                                     482

<210> SEQ ID NO 30
<211> LENGTH: 489
<212> TYPE: DNA
<213> ORGANISM: Artificial Sequence
<220> FEATURE:
<223> OTHER INFORMATION: ANA ID NO: 13 (PhiX Fragment Sense 13)

<400> SEQUENCE: 30
tttttgccat cagattgtgt tgttagtcg ctgtcaaaaa ttacgtgcgg aaggagtgat         60
gtaatgtcta aggtaaaaa acgttctggc gctcgccctg tcgtccgca gccgttgcga       120 ggtactaaag gcaagcgtaa aggcgctcgt ctttggtatg taggtggtca acaattttaa      180
ttgcaggggc ttcggcccct tacttgagga taaattatgt ctaatattca aactggcgcc      240
gagcgtatgc cgcatgacct ttcccatctt ggcttccttg ctggtcagat tggtcgtctt      300
attaccattt caactactcc ggttatcgct ggcgactcct tcgagatgga cgccgttggc      360
gctctccgtc tttctccatt gcgtcgtggc cttgctattg actctactgt agacattttt      420 acttttatg tccctcatct tttttcccct ttttcccct ttttcccct tttcccct              480 tttccccc                                                              489

<210> SEQ ID NO 31
<211> LENGTH: 482
<212> TYPE: DNA
<213> ORGANISM: Artificial Sequence
<220> FEATURE:
<223> OTHER INFORMATION: ANA ID NO: 14 (PhiX Fragment Sense 14)

<400> SEQUENCE: 31
tttttgccat cagattgtgt tgttagtcg cttccttcga gatggacgcc gttggcgctc         60
tccgtctttc tccattgcgt cgtggccttg ctattgactc tactgtagac attttttactt      120 tttatgtccc tcatcgtcac gtttatggtg aacagtggat taagttcatg aaggatggtg      180
ttaatgccac tcctctcccg actgttaaca ctactggtta tattgaccat gccgcttttc      240
ttggcacgat taaccctgat accaataaaa tccctaagca tttgtttcag ggttatttga      300
```

| | |
|---|---|
| atatctataa caactatttt aaagcgccgt ggatgcctga ccgtaccgag gctaacccta | 360 |
| atgagcttaa tcaagatgat gctcgttatg gtttccgttg ctgccatctc aaaaacattt | 420 |
| ggactgctcc gctttttccc cctttttccc cctttttccc cctttttccc cctttttccc | 480 |
| cc | 482 |

<210> SEQ ID NO 32
<211> LENGTH: 482
<212> TYPE: DNA
<213> ORGANISM: Artificial Sequence
<220> FEATURE:
<223> OTHER INFORMATION: ANA ID NO: 15 (PhiX Fragment Sense 15)

<400> SEQUENCE: 32

| | |
|---|---|
| tttttgccat cagattgtgt tgttagtcg ctatgcctga ccgtaccgag gctaacccta | 60 |
| atgagcttaa tcaagatgat gctcgttatg gtttccgttg ctgccatctc aaaaacattt | 120 |
| ggactgctcc gcttcctcct gagactgagc tttctcgcca aatgacgact tctaccacat | 180 |
| ctattgacat tatgggtctg caagctgctt atgctaattt gcatactgac caagaacgtg | 240 |
| attacttcat gcagcgttac catgatgtta tttcttcatt tggaggtaaa acctcttatg | 300 |
| acgctgacaa ccgtccttta cttgtcatgc gctctaatct ctgggcatct ggctatgatg | 360 |
| ttgatggaac tgaccaaacg tcgttaggcc agttttctgg tcgtgttcaa cagacctata | 420 |
| aacattctgt gctttttccc cctttttccc cctttttccc cctttttccc cctttttccc | 480 |
| cc | 482 |

<210> SEQ ID NO 33
<211> LENGTH: 482
<212> TYPE: DNA
<213> ORGANISM: Artificial Sequence
<220> FEATURE:
<223> OTHER INFORMATION: ANA ID NO: 16 (PhiX Fragment Sense 16)

<400> SEQUENCE: 33

| | |
|---|---|
| tttttgccat cagattgtgt tgttagtcg cttctaatct ctgggcatct ggctatgatg | 60 |
| ttgatggaac tgaccaaacg tcgttaggcc agttttctgg tcgtgttcaa cagacctata | 120 |
| aacattctgt gccgcgtttc tttgttcctg agcatggcac tatgtttact cttgcgcttg | 180 |
| ttcgttttcc gcctactgcg actaaagaga ttcagtacct aacgctaaa ggtgctttga | 240 |
| cttataccga tattgctggc gaccctgttt tgtatggcaa cttgccgccg cgtgaaattt | 300 |
| ctatgaagga tgttttccgt tctggtgatt cgtctaagaa gtttaagatt gctgagggtc | 360 |
| agtggtatcg ttatgcgcct tcgtatgttt ctcctgctta tcaccttctt gaaggcttcc | 420 |
| cattcattca ggttttccc cctttttccc cctttttccc cctttttccc cctttttccc | 480 |
| cc | 482 |

<210> SEQ ID NO 34
<211> LENGTH: 482
<212> TYPE: DNA
<213> ORGANISM: Artificial Sequence
<220> FEATURE:
<223> OTHER INFORMATION: ANA ID NO: 17 (PhiX Fragment Sense 17)

<400> SEQUENCE: 34

| | |
|---|---|
| tttttgccat cagattgtgt tgttagtcg cttctaagaa gtttaagatt gctgagggtc | 60 |
| agtggtatcg ttatgcgcct tcgtatgttt ctcctgctta tcaccttctt gaaggcttcc | 120 |

```
cattcattca ggaaccgcct tctggtgatt tgcaagaacg cgtacttatt cgccaccatg    180
attatgacca gtgtttccag tccgttcagt tgttgcagtg gaatagtcag gttaaattta    240
atgtgaccgt ttatcgcaat ctgccgacca ctcgcgattc aatcatgact tcgtgataaa    300
agattgagtg tgaggttata acgccgaagc ggtaaaaatt ttaatttttg ccgctgaggg    360
gttgaccaag cgaagcgcgg taggttttct gcttaggagt ttaatcatgt ttcagacttt    420
tatttctcgc catttttccc ccttttttccc ccttttttccc ccttttttccc ccttttttccc    480 cc                                                                   482
```

```
<210> SEQ ID NO 35
<211> LENGTH: 571
<212> TYPE: DNA
<213> ORGANISM: Artificial Sequence
<220> FEATURE:
<223> OTHER INFORMATION: ANA ID NO: 18 (PhiX Fragment Sense 18)

<400> SEQUENCE: 35 ttttttgccat cagattgtgt tgttagtcg ctgttataac gccgaagcgg taaaaatttt    60
aatttttgcc gctgaggggt tgaccaagcg aagcgcggta ggttttctgc ttaggagttt    120
aatcatgttt cagactttta tttctcgcca taattcaaac tttttttctg ataagctggt    180
tctcacttct gttactccag cttcttcggc acctgtttta cagacaccta aagctacatc    240
gtcaacgtta tattttgata gtttgacggt taatgctggt aatggtggtt ttcttcattg    300
cattcagatg gatacatctg tcaacgccgc taatcaggtt gtttctgttg gtgctgatat    360
tgcttttgat gccgacccta aatttttttgc ctgtttggtt cgctttgagt cttcttcggt    420
tccgactacc ctcccgactg cctatgatgt ttatcctttg gatggtcgcc atgatggtgg    480
ttattatacc gtcaaggact gtgtgactat tgacgtcctt ccttttttcccc ccttttttcccc    540 ccttttttcccc ccttttttcccc ccttttttcccc c                              571
```

```
<210> SEQ ID NO 36
<211> LENGTH: 489
<212> TYPE: DNA
<213> ORGANISM: Artificial Sequence
<220> FEATURE:
<223> OTHER INFORMATION: ANA ID NO: 19 (PhiX Fragment Sense 13-T335A-
      G357T-C385A)

<400> SEQUENCE: 36 ttttttgccat cagattgtgt tgttagtcg ctgtcaaaaa ttacgtgcgg aaggagtgat    60
gtaatgtcta aaggtaaaaa acgttctggc gctcgccctg gtagtccgca gccgttgcga    120
ggtactaaag tcaagcgtaa aggcgctcgt ctatggtatg taggtggtca acaattttaa    180 ttgcagggggc ttcggcccct tacttgagga taaattatgt ctaatattca aactggcgcc    240
gagcgtatgc cgcatgacct ttcccatctt ggcttccttg ctggtcagat tggtcgtctt    300
attaccattt caactactcc ggttatcgct ggcgactcct tcgagatgga cgccgttggc    360
gctctccgtc tttctccatt gcgtcgtggc cttgctattg actctactgt agacattttt    420 acttttttatg tccctcatct ttttccccct ttttccccct ttttccccct ttttccccct    480
ttttccccc                                                            489
```